US009840545B2

(12) United States Patent
Sharma et al.

(10) Patent No.: US 9,840,545 B2
(45) Date of Patent: Dec. 12, 2017

(54) FUSION PROTEIN COMPRISING INTERLEUKIN-2 AND INTERLEUKIN-33

(71) Applicant: University of Virginia Patent Foundation, Charlottesville, VA (US)

(72) Inventors: Rahul Sharma, Charlottesville, VA (US); Mark D. Okusa, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/026,927

(22) PCT Filed: Sep. 22, 2014

(86) PCT No.: PCT/US2014/056767
§ 371 (c)(1),
(2) Date: Apr. 1, 2016

(87) PCT Pub. No.: WO2015/042521
PCT Pub. Date: Mar. 26, 2015

(65) Prior Publication Data
US 2016/0304574 A1 Oct. 20, 2016

Related U.S. Application Data

(60) Provisional application No. 61/880,257, filed on Sep. 20, 2013.

(51) Int. Cl.
| | |
|---|---|
| *C07K 14/54* | (2006.01) |
| *A61K 38/20* | (2006.01) |
| *C07K 14/55* | (2006.01) |
| *A61K 38/00* | (2006.01) |

(52) U.S. Cl.
CPC .............. *C07K 14/55* (2013.01); *C07K 14/54* (2013.01); *A61K 38/00* (2013.01); *C07K 2319/74* (2013.01)

(58) Field of Classification Search
CPC ..... C07K 2319/00; C07K 14/55; C07K 14/54
See application file for complete search history.

(56) References Cited

U.S. PATENT DOCUMENTS

| 5,496,924 A | 3/1996 | Habermann et al. |
| 2005/0063945 A1 | 3/2005 | Paul |
| 2005/0203046 A1 | 9/2005 | Schmitz et al. |
| 2008/0003199 A1 | 1/2008 | Lee |
| 2011/0250170 A1 | 10/2011 | Pedretti et al. |

FOREIGN PATENT DOCUMENTS

| WO | WO 03/035105 A2 | 5/2003 |
| WO | WO 2005/014642 A2 | 2/2005 |

OTHER PUBLICATIONS

Jiang, H.R., et al., "IL-33 attenuates EAE by suppressing IL-17 and IFN-β production and inducing alternatively activated macrophages," Eur. J. Immunol. Jun. 12, 2012 (Jun. 12, 2012), vol. 42, No. 7, pp. 1804-1814.
Cote-Sierra, et al., "Interleukin 2 plays a central role in TH2 differentiation," Proc. Natl. Acad. Sci., Mar. 5, 2004 (Mar. 5, 2004), vol. 101, No. 11, pp. 3880-3885.
Boyman O, Sprent J. 2012. "The role of interleukin-2 during homeostasis and activation of the immune system", Nat Rev Immunol 12: 180-90.
Tang Q, Bluestone JA, Kang SM. 2012. "CD4(+)Foxp3(+) regulatory T cell therapy in transplantation", J Mol Cell Biol 4: 11-21.
Shevach EM. 2011. "Biological functions of regulatory T cells", Adv Immunol 112: 137-76.
Duan L, Chen J, Zhang H, Yang H, Zhu P, Xiong A, Xia Q, Zheng F, Tan Z, Gong F, Fang M. 2012. "Interleukin-33 Ameliorates Experimental Colitis through Promoting Th2/Foxp3(+) Regulatory T-Cell Responses in Mice", Mol Med 18:753-61.
Sharma R, Sung SS, Gaskin F, Fu SM, Ju ST. 2012. "A novel function of IL-2: chemokine/chemoattractant/retention receptor genes induction in Th subsets for skin and lung inflammation", J Autoimmun 38: 322-31.
Sharma R, Fu SM, Ju ST. 2011. "IL-2: a two-faced master regulator of autoimmunity", J Autoimmun 36: 91-7.
Sharma R, Sharma PR, Kim YC, Leitinger N, Lee JK, Fu SM, Ju ST. 2011. "IL-2-controlled expression of multiple T cell trafficking genes and Th2 cytokines in the regulatory T cell-deficient scurfy mice: implication to multiorgan inflammation and control of skin and lung inflammation", J Immunol 186: 1268-78.
Turnquist HR, Zhao Z, Rosborough BR, Liu Q, Castellaneta A, Isse K, Wang Z, Lang M, Stolz DB, Zheng XX, Demetris AJ, Liew FY, Wood KJ, Thomson AW. 2011. "IL-33 expands suppressive CD11b+ Gr-1(int) and regulatory T cells, including ST2L+ Foxp3+ cells, and mediates regulatory T cell-dependent promotion of cardiac allograft survival", J Immunol 187: 4598-610.
Mjosberg JM, Trifari S, Crellin NK, Peters CP, van Drunen CM, Piet B, Fokkens WJ, Cupedo T, Spits FL 2011. "Human IL-25- and IL-33-responsive type 2 innate lymphoid cells are defined by expression of CRTH2 and CD161", Nat Immunol 12: 1055-62.
Yasuda K, Muto T, Kawagoe T, Matsumoto M, Sasaki Y, Matsushita K, Taki Y, Futatsugi-Yumikura 5, Tsutsui H, Ishii KJ, Yoshimoto T, Akira S, Nakanishi K. 2012. "Contribution of IL-33-activated type II innate lymphoid cells to pulmonary eosinophilia in intestinal nematode-infected mice", Proc Natl Acad Sci U S A 109: 3451-6.
Bartemes KR, Iijima K, Kobayashi T, Kephart GM, McKenzie AN, Kita H. 2012. "IL-33-responsive lineage—CD25+ CD44(hi) lymphoid cells mediate innate type 2 immunity and allergic inflammation in the lungs", J Immunol 188: 1503-13.

(Continued)

*Primary Examiner* — Prema Mertz
(74) *Attorney, Agent, or Firm* — Rodney L. Sparks

(57) ABSTRACT

The present application discloses a novel fusion peptide of IL-2 and IL-33 and its use. It comprises a biologically active domain of Interleukin-2 (IL-2) or a biologically active fragment or homolog thereof, and a biologically active domain of Interleukin-33 (IL-33) or a biologically active fragment or homolog thereof. The two portions can be linked by a linker sequence. The application discloses that combination therapies using IL-2 and IL-33 or a therapy using the IL233 fusion protein are effective in preventing or treating diseases and disorders such as autoimmune diseases and disorders, inflammation, etc. Depending on the subject's disease or disorder, the compositions of the invention are useful for preventing certain symptoms, treating the disease, and alleviating at least some of the symptoms.

8 Claims, 28 Drawing Sheets
(12 of 28 Drawing Sheet(s) Filed in Color)

(56) References Cited

OTHER PUBLICATIONS

Besnard AG, Togbe D, Guillou N, Erard F, Quesniaux V, Ryffel B. 2011. "IL-33-activated dendritic cells are critical for allergic airway inflammation", Eur J Immunol 41: 1675-86.

Miller AM, Asquith DL, Hueber AJ, Anderson LA, Holmes WM, McKenzie AN, Xu D, Sattar N, McInnes IB, Liew FY. 2010. "Interleukin-33 induces protective effects in adipose tissue inflammation during obesity in mice", Circ Res 107: 650-8.

Sharma R, Sharma PR, Kim YC, Leitinger N, Lee JK, Fu SM, Ju ST. 2011. Correction: "IL-2-controlled expression of multiple T cell trafficking genes and Th2 cytokines in the regulatory T cell-deficient scurfy mice: implication to multiorgan inflammation and control of skin and lung inflammation", J Immunol 186/8/5012.

Rock, F. et al., "Overexpression and structure-function analysis of a bioengineered IL-2/IL-6 chimeric lymphokine", Protein Engineering, Oxford University Press, Surrey, GB, vol. 5, No. 6, Sep. 1, 1992 (Sep. 1, 1992), pp. 583-591, XP000983961, ISSN: 0269-2139.

M. G. Von Herrath, et al., "Focal Expression of Interleukin-2 Does Not Break Unresponsiveness to "Self" (Viral) Antigen Expressed in β Cells but Enhances Development of Autoimmune Disease (Diabetes) after Initiation of an Anti-Self Immune Response", Journal of Clinical Investigation, vol. 95, No. 2, Feb. 1, 1995 (Feb. 1, 1995), pp. 477-485, XP055355172, US ISSN: 0021-9738, DOI: 10.1172/JCI117688.

Ashley M. Miller, "Role of IL-33 in inflammation and disease", Journal of Inflammation, Biomed Central, London, GB, vol. 8, No. 1, Aug. 26, 2011 (Aug. 26, 2011), 12 pages, XP021109127, ISSN: 1476-9255, DOI: 10.1186/1476-9255-8-22.

Palmer, Gaby et al., "Interleukin-33 biology with potential insights into human diseases", Nature Reviews, Rheumatology, Nature Publ. Group, USA, vol. 7, No. 6, Jun. 1, 2011 (Jun. 1, 2011), pp. 321-329, XP009178467, ISSN: 1759-4804, DOI: 10.1038/NRRHEUM.2011.53.

Jie Wu, Aini Xie, and Wenhao Chen, "Cytokine regulation of immune tolerance", Burns & Trauma, vol. 2, No. 1, Jan. 1, 2014 (Jan. 1, 2014), pp. 11-17, XP055354744, ISSN: 2321-3868, DOI: 10.4103/2321-3868.124771.

IL-2 regulates inflammation in the Pancreas of mice independent of Tregs.

IL-2 regulates inflammation in the Pancreas of mice independent of Tregs.

IL-2 regulates inflammation in the Pancreas of mice independent of Tregs.

| Table 2. The CD4+ T-cells from LN of Sf.Il2−/− mice displayed high expression of TfH genes compared to B6 & Sf mice | | |
|---|---|---|
| Gene | vs B6 | vs Sf |
| Cxcr5 | 8.0 | 3.6 |
| Pdcd1 (PD-1) | 9.7 | 2.5 |
| Il21 | 9.0 | 1.5 |
| Batf | 6.1 | 1.7 |
| c-Maf | 5.5 | 1.1 |
| Icos | 5.0 | 1.6 |
| Sh2d1a (Sap) | 2.9 | 2.2 |
| Bcl6 | 1.9 | 1.7 |
| Il22 | 13.5 | 6.8 |
| Il10 | 7.9 | -1.9 |
| Il4 | 13.7 | -1.4 |

IL-2 is a negative regulator of T follicular helper (TfH) differentiation.

The natural Tregs (nTr) express IL-33 receptor (IL1RL1)

Treatment with IL233 increases natural Tregs (Foxp3+Helios+) in mice.

Treatment of mice with IL233 protects non-obese diabetic (NOD) mice from type-1 diabetes like disease.

Treatment of mice with IL233 protects non-obese diabetic (NOD) mice from type-1 diabetes like disease.

Treatment with IL233 expands Treg cells especially in the pancreatic Lymph nodes.

Treatment with IL233 or mixture of IL-2 and IL-33 protects C57BL/6 mice from renal ischemia reperfusion injury (IRI).

Treatment with IL233 or mixture of IL-2 and IL-33 protects C57BL/6 mice from renal ischemia reperfusion injury (IRI).

Treatment with IL233 or mixture of IL-2 and IL-33 protects C57BL/6 mice from renal ischemia reperfusion injury (IRI).

Treatment with IL233 protects lupus prone NZM2328 mice from lupus glomerulonephritis (GN).

Treatment with IL233 protects lupus prone NZM2328 mice from lupus glomerulonephritis (GN).

Treatment with IL233 as well as the IL-2 and IL-33 combination is more effective than either cytokine alone to protect lupus prone NZM2328 mice from GN.

Treatment with IL233 as well as the IL-2 and IL-33 combination is more effective than either cytokine alone to protect lupus prone NZM2328 mice from GN.

Treatment with IL233 as well as the IL-2 and IL-33 combination is more effective than either cytokine alone to protect lupus prone NZM2328 mice from GN.

Treatment with IL233 as well as the IL-2 and IL-33 combination is more effective than either cytokine alone to protect lupus prone NZM2328 mice from GN.

Treatment with IL233 inhibits progression of obesity, type-2 diabetes (T2D) and diabetic nephropathy in mice genetically predisposed for obesity.

Treatment with IL233 inhibits progression of obesity, type-2 diabetes (T2D) and diabetic nephropathy in mice genetically predisposed for obesity.

$*\ p < 0.05$

Treatment with IL233 inhibits progression of obesity, type-2 diabetes (T2D) and diabetic nephropathy in mice genetically predisposed for obesity.

Treatment with IL233 inhibits progression of obesity, type-2 diabetes (T2D) and diabetic nephropathy in mice genetically predisposed for obesity.

Sequence (SEQ ID NO:1) of the synthetic gene for the expression of human IL233 fusion protein:

GAATTCGAGAACTACTTCCAGGGTGCTCCGACCCTCTCTTCTACCAAGAAAACCCAG
CTGCAGCTGGAACACCTGCTGCTGGACCTGCAGATGATCCTGAACGGTATCAATAACTAC
AAGAACCCGAAACTGACCCGTATGCTGACCTTCAAATTCTACATGCCGAAGAAAGCTACC
GAACTGAAACACCTGCAGTGCCTGGAAGAGGAACTTGAAAACCTGGAAGAAGTTCTGAAC
CTGGCTCAGTCTAAGAACTTCCACCTCCGCGTTCCGATCTCTAACATCAACGTT
ATCGTTCTGGAACTGAAAGGTTCCGAACCCGTTGGATCCACTTTCATGTGCGAATACGCTGACGAAAACC
GCTACCATCGTTGAGTTCCTGAACCGTTGGATCACCTTCTCCCAGTCTATCATCTCTACC
CTGACCGGTGGTGGCGGTTCTGGCGGTGGTGGGGTTCTGGCGGTGGATCCAGCATCACC
GGCATCAGCGGCGTGACCGACTACGAGATCTACGAGAACGTGAGCACCGAGATCCACAGC
ACCTTCGCCCTGCTGAGAGATCTCTACTACGAGGACCACTGCGAGACCCTGAAGAAGCGGC
AAGAAGGACAAGGTGCTGCTGAGCTACTGATGTGGAGCTGCACAGCAGCAAGGACCCCCACCC
GACGGCGTGGACAAGGAGCACAGCAGCGGTGCAACATGCAAGCTGCGAGAAGCCCGAC
CACGCCAACAAGAGCGTGCACAACATGCGCGTGAAGCAACAACCACAACCGCCCTGCCCGAC
CAGGCCTTCTTCGCTGTCATCGGCGTGAAGAACAACATCCCTGTTCAAGCTGAGCCCTGATCAAGACC
GACCCGGCGTGTTCACCGAGAACATCCCTGTTCAAGCTGAGCGAGACCTAACTCGAG
AGCGAGAACCTGTGCACCGAGAACTACTTCCAGGGCTGAGCGAGACCTAACTCGAG

FIG. 11A

Amino-acid sequence (SEQ ID NO:2) of the human IL233 fusion protein:

GAPTSSSTKKTQLQLEHLLLDLQMILNGINNYKNPKLTRMLTFKFYMPKK
ATELKHLQCLEEELKPLEEVLNLAQSKNFHLRPRDLISNINVIVLELKGS
ETTFMCEYADETATIVEFLNRWITFCQSIISTLTGGGGSGGGGSGGGGSS
ITGISPITEYLASLSTYNDQSITFALEDESYEIYVEDLKKDKVLLS
YYESQHPSNESGDVDGKMLMVTLSPTKDFWLHANNKEHSVELHKCEKPL
PDQAFFVLHNMHSNCVSFECKTDPGVFIGVKDNHLALIKVDSSENLCTEN
ILFKLSET

FIG. 11B

Sequence (SEQ ID NO:10) of the synthetic gene for the expression of murine IL233 fusion protein:

GAATTCGAGAACCTGTACTTCCAGGGTGCACCCACTTCAAGCTCCACTTCAAGCTCTACA
GCGGAAGCACAGCAGCAGCAGCAGCAGCAGCAGCAGCAGCAGCAGCAGCCTGGAGCAGCTG
TTCATCGACTACACAGGACTCCTGAGCAGCAGGATGGAGAATTACAGAACCTGAAACTCCCC
ACGATGCTCACCTCAAATTTTACTTGCCCAAGCAGCCCACAGAATTGAAAGATCTTCAG
TGCCTAGAAGATGAACTTGGACCCTTCTGCGGCATGTTCTGGATTTGACTCAAAGCAAAAGC
TTTCAATTGAAGATGCTGAGAATTTCATTGAGTGCCAATTCAGATAACTGTGTAAAACTA
AAGGGCTCTGACAACACATTTGAGTGCCAATTTGAGCCTGTGTCAAGAACTCTCAACAAGCCCCTCAAGGTGGT
TTTCTCAGGAGAGATGGATAGCCTTCCTCTGTGGTGGCCGGTGATCCTCTATCCAGGTACTTCTCTG
GGCGGTCTGGCGGTGGCGGCTTCCCGGCTCTACCTGCGGCGGTGATCCTCTATCCAGGTACTTCTCTG
CTGACCCAGTCTCCGGCTCTACGTTGCTGCTACCAGTCTCGTGTTTCTTTCGTTCTG
GAAAACGGTTACTACTGCAACGGTATCAACGACGACTCTGGTAAGACCAGGAACCAGGACCAG
GTTCTGCTGCGTGTACTACGAATCTCCGGCTTTCTCAGTCTGGTGACGGTGTTGAC
GGTAAGAAGTTATGGTTAACATGTTAACACCGACATCTGGCTGCACGCT
AACGACAAAGACTACTCTGTTGACAAAGAAATCTTCGACTTCGTTTCTTTCTGAATGCAAGAACCTGCCG
TTCTTCGTTCTGCACAAGAAAATCTTCGACTTCGTTTCTTTCTGAATGCAAGAACCTGCCG
GGTACTTACATCGGTTAAAGAACAACCAGCTCGCTGGTTGAAGAGAAAGACGAATCT
TGCCAACAACATCATGTTCAAACTGTTCAAATCTAACTCCAG

FIG. 11C

Amino-acid sequence (SEQ ID NO:11) of the murine IL233 fusion protein:

GAPTSSTSSSTAEAQQQQQQQQQQQQQHLEQLLMDLQELLSRMENYRNLK
LPRMLTFKFYLPKQATELKDLQCLEDELGPLRHVLDLTQSKSFQLEDAEN
FISNIRVTVVKLKGSDNTFECQFDDESATVDFLRRWIAFCQSIISTSPQ
GGGSGGGGSGGGGSIQGTSLLTQSPASLSTYNDQSVSFVLENGCVIN
VDDSGKDQEQDQVLLRYESPCPASQSGDVDGKKVMVNMSPIKDTDIWL
HANDKDYSVELQRGDVSPPEQAFFVLHKKSSDFVSFECKNLPGTYLGVKD
NQLALVEEKDESCNNIMFKLSKI

FIG. 11D

SEQUENCE LISTING

```
<160> NUMBER OF SEQ ID NOS: 11

<210> SEQ ID NO 1
<211> LENGTH: 957
<212> TYPE: DNA
<213> ORGANISM: homo sapiens

<400> SEQUENCE: 1
gaattcgaga acctgtactt ccagggtgct ccgacctctt cttctaccaa gaaaacccag      60
ctgcagctgg aacacctgtt gctggacctg cagatgatcc tgaacggtat caataactac     120
aagaacccga aactgacccg tatgctgacc ttcaaattct acatgccgaa gaaagctacc     180
gaactgaaac acctgcagtg cctggaagag gaactgaaac cgctggaaga agttctgaac     240
ctggctcagt ctaagaactt ccacctgcgt ccgcgtgacc tgatctctaa catcaacgtt     300
atcgttctgg aactgaaagg ttctgaaacc accttcatgt gcgaatacgc tgacgaaacc     360
gctaccatcg ttgagttcct gaaccgttgg atcaccttct gccagtctat catctctacc     420
ctgaccggtg gtggcggttc tggcggtggc ggttctggtg gcggtggatc cagcatcacc     480
ggcatcagcc ccatcaccga gtacctggcc agcctgagca cctacaacga ccagagcatc     540
accttcgccc tggaggacga gagctacgag atctacgtgg aggacctgaa gaaggacgag     600
aagaaggaca aggtgctgct gagctactac gagagccagc accccagcaa cgagagcggc     660
gacggcgtgg acggcaagat gctgatggtg accctgagcc ccaccaagga cttctggctg     720
cacgccaaca acaaggagca cagcgtggag ctgcacaagt gcgagaagcc cctgcccgac     780
caggccttct tcgtgctgca caacatgcac agcaactgcg tgagcttcga gtgcaagacc     840
gaccccggcg tgttcatcgg cgtgaaggac aaccacctgg ccctgatcaa ggtggacagc     900
agcgagaacc tgtgcaccga gaacatcctg ttcaagctga gcgagaccta actcgag       957

<210> SEQ ID NO 2
<211> LENGTH: 308
<212> TYPE: PRT
<213> ORGANISM: homo sapiens

<400> SEQUENCE: 2

Gly Ala Pro Thr Ser Ser Ser Thr Lys Lys Thr Gln Leu Gln Leu Glu
```

```
 1               5                   10                  15
His Leu Leu Leu Asp Leu Gln Met Ile Leu Asn Gly Ile Asn Asn Tyr
                20                  25                  30

Lys Asn Pro Lys Leu Thr Arg Met Leu Thr Phe Lys Phe Tyr Met Pro
                35                  40                  45

Lys Lys Ala Thr Glu Leu Lys His Leu Gln Cys Leu Glu Glu Glu Leu
                50                  55                  60

Lys Pro Leu Glu Glu Val Leu Asn Leu Ala Gln Ser Lys Asn Phe His
 65                 70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
                100                 105                 110

Ala Thr Ile Val Glu Phe Leu Asn Arg Trp Ile Thr Phe Cys Gln Ser
                115                 120                 125

Ile Ile Ser Thr Leu Thr Gly Gly Gly Ser Gly Gly Gly Gly Ser
                130                 135                 140

Gly Gly Gly Gly Ser Ser Ile Thr Gly Ile Ser Pro Ile Thr Glu Tyr
145                 150                 155                 160

Leu Ala Ser Leu Ser Thr Tyr Asn Asp Gln Ser Ile Thr Phe Ala Leu
                165                 170                 175

Glu Asp Glu Ser Tyr Glu Ile Tyr Val Glu Asp Leu Lys Lys Asp Glu
                180                 185                 190

Lys Lys Asp Lys Val Leu Leu Ser Tyr Tyr Glu Ser Gln His Pro Ser
                195                 200                 205

Asn Glu Ser Gly Asp Gly Val Asp Gly Lys Met Leu Met Val Thr Leu
                210                 215                 220

Ser Pro Thr Lys Asp Phe Trp Leu His Ala Asn Asn Lys Glu His Ser
225                 230                 235                 240

Val Glu Leu His Lys Cys Glu Lys Pro Leu Pro Asp Gln Ala Phe Phe
                245                 250                 255

Val Leu His Asn Met His Ser Asn Cys Val Ser Phe Glu Cys Lys Thr
                260                 265                 270

Asp Pro Gly Val Phe Ile Gly Val Lys Asp Asn His Leu Ala Leu Ile
                275                 280                 285

Lys Val Asp Ser Ser Glu Asn Leu Cys Thr Glu Asn Ile Leu Phe Lys
                290                 295                 300

Leu Ser Glu Thr
305

<210> SEQ ID NO 3
<211> LENGTH: 134
<212> TYPE: PRT
<213> ORGANISM: homo sapiens

<400> SEQUENCE: 3

Gly Ala Pro Thr Ser Ser Ser Thr Lys Lys Thr Gln Leu Gln Leu Glu
 1               5                   10                  15

His Leu Leu Leu Asp Leu Gln Met Ile Leu Asn Gly Ile Asn Asn Tyr
                20                  25                  30

Lys Asn Pro Lys Leu Thr Arg Met Leu Thr Phe Lys Phe Tyr Met Pro
                35                  40                  45

Lys Lys Ala Thr Glu Leu Lys His Leu Gln Cys Leu Glu Glu Glu Leu
                50                  55                  60
```

```
Lys Pro Leu Glu Glu Val Leu Asn Leu Ala Gln Ser Lys Asn Phe His
 65                  70                  75                  80

Leu Arg Pro Arg Asp Leu Ile Ser Asn Ile Asn Val Ile Val Leu Glu
                 85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130
```

<210> SEQ ID NO 4
<211> LENGTH: 159
<212> TYPE: PRT
<213> ORGANISM: homo sapiens

<400> SEQUENCE: 4

```
Ser Ile Thr Gly Ile Ser Pro Ile Thr Glu Tyr Leu Ala Ser Leu Ser
  1               5                  10                  15

Thr Tyr Asn Asp Gln Ser Ile Thr Phe Ala Leu Glu Asp Glu Ser Tyr
             20                  25                  30

Glu Ile Tyr Val Glu Asp Leu Lys Lys Asp Glu Lys Lys Asp Lys Val
         35                  40                  45

Leu Leu Ser Tyr Tyr Glu Ser Gln His Pro Ser Asn Glu Ser Gly Asp
     50                  55                  60

Gly Val Asp Gly Lys Met Leu Met Val Thr Leu Ser Pro Thr Lys Asp
 65                  70                  75                  80

Phe Trp Leu His Ala Asn Asn Lys Glu His Ser Val Glu Leu His Lys
                 85                  90                  95

Cys Glu Lys Pro Leu Pro Asp Gln Ala Phe Phe Val Leu His Asn Met
            100                 105                 110

His Ser Asn Cys Val Ser Phe Glu Cys Lys Thr Asp Pro Gly Val Phe
        115                 120                 125

Ile Gly Val Lys Asp Asn His Leu Ala Leu Ile Lys Val Asp Ser Ser
    130                 135                 140

Glu Asn Leu Cys Thr Glu Asn Ile Leu Phe Lys Leu Ser Glu Thr
145                 150                 155
```

<210> SEQ ID NO 5
<211> LENGTH: 15
<212> TYPE: PRT
<213> ORGANISM: homo sapiens

<400> SEQUENCE: 5

```
Gly Gly Gly Gly Ser Gly Gly Gly Gly Ser Gly Gly Gly Gly Ser
  1               5                  10                  15
```

<210> SEQ ID NO 6
<211> LENGTH: 153
<212> TYPE: PRT
<213> ORGANISM: homo sapiens

<400> SEQUENCE: 6

```
Met Tyr Arg Met Gln Leu Leu Ser Cys Ile Ala Leu Ser Leu Ala Leu
  1               5                  10                  15

Val Thr Asn Ser Ala Pro Thr Ser Ser Ser Thr Lys Lys Thr Gln Leu
             20                  25                  30

Gln Leu Glu His Leu Leu Leu Asp Leu Gln Met Ile Leu Asn Gly Ile
```

```
            35                  40                  45
Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
 65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr
145                 150

<210> SEQ ID NO 7
<211> LENGTH: 270
<212> TYPE: PRT
<213> ORGANISM: homo sapiens

<400> SEQUENCE: 7

Met Lys Pro Lys Met Lys Tyr Ser Thr Asn Lys Ile Ser Thr Ala Lys
 1               5                  10                  15

Trp Lys Asn Thr Ala Ser Lys Ala Leu Cys Phe Lys Leu Gly Lys Ser
                20                  25                  30

Gln Gln Lys Ala Lys Glu Val Cys Pro Met Tyr Phe Lys Leu Leu Arg
            35                  40                  45

Ser Gly Leu Met Ile Lys Lys Glu Ala Cys Tyr Phe Arg Arg Glu Thr
        50                  55                  60

Thr Lys Arg Pro Ser Leu Lys Thr Gly Arg Lys His Lys Arg His Leu
 65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255
```

```
Asn Leu Cys Thr Glu Asn Ile Leu Phe Lys Leu Ser Glu Thr
            260                 265                 270

<210> SEQ ID NO 8
<211> LENGTH: 169
<212> TYPE: PRT
<213> ORGANISM: mus musculus

<400> SEQUENCE: 8

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln
                165

<210> SEQ ID NO 9
<211> LENGTH: 266
<212> TYPE: PRT
<213> ORGANISM: Mus musculus

<400> SEQUENCE: 9

Met Arg Pro Arg Met Lys Tyr Ser Asn Ser Lys Ile Ser Pro Ala Lys
1               5                   10                  15

Phe Ser Ser Thr Ala Gly Glu Ala Leu Val Pro Pro Cys Lys Ile Arg
            20                  25                  30

Arg Ser Gln Gln Lys Thr Lys Glu Phe Cys His Val Tyr Cys Met Arg
        35                  40                  45

Leu Arg Ser Gly Leu Thr Ile Arg Lys Glu Thr Ser Tyr Phe Arg Lys
50                  55                  60

Glu Pro Thr Lys Arg Tyr Ser Leu Lys Ser Gly Thr Lys His Glu Glu
65                  70                  75                  80

Asn Phe Ser Ala Tyr Pro Arg Asp Ser Arg Lys Arg Ser Leu Leu Gly
                85                  90                  95

Ser Ile Gln Ala Phe Ala Ala Ser Val Asp Thr Leu Ser Ile Gln Gly
            100                 105                 110

Thr Ser Leu Leu Thr Gln Ser Pro Ala Ser Leu Ser Thr Tyr Asn Asp
        115                 120                 125

Gln Ser Val Ser Phe Val Leu Glu Asn Gly Cys Tyr Val Ile Asn Val
130                 135                 140
```

```
Asp Asp Ser Gly Lys Asp Gln Glu Gln Asp Gln Val Leu Leu Arg Tyr
145                 150                 155                 160

Tyr Glu Ser Pro Cys Pro Ala Ser Gln Ser Gly Asp Gly Val Asp Gly
                165                 170                 175

Lys Lys Leu Met Val Asn Met Ser Pro Ile Lys Asp Thr Asp Ile Trp
            180                 185                 190

Leu His Ala Asn Asp Lys Asp Tyr Ser Val Glu Leu Gln Arg Gly Asp
        195                 200                 205

Val Ser Pro Pro Glu Gln Ala Phe Phe Val Leu His Lys Lys Ser Ser
    210                 215                 220

Asp Phe Val Ser Phe Glu Cys Lys Asn Leu Pro Gly Thr Tyr Ile Gly
225                 230                 235                 240

Val Lys Asp Asn Gln Leu Ala Leu Val Glu Glu Lys Asp Glu Ser Cys
                245                 250                 255

Asn Asn Ile Met Phe Lys Leu Ser Lys Ile
                260                 265

<210> SEQ ID NO 10
<211> LENGTH: 1002
<212> TYPE: DNA
<213> ORGANISM: Mus musculus

<400> SEQUENCE: 10
gaattcgaga acctgtactt ccagggtgca cccacttcaa gctccacttc aagctctaca      60
gcggaagcac agcagcagca gcagcagcag cagcagcagc agcagcacct ggagcagctg     120
ttgatggacc tacaggagct cctgagcagg atggagaatt acaggaacct gaaactcccc     180
aggatgctca ccttcaaatt ttacttgccc aagcaggcca cagaattgaa agatcttcag     240
tgcctagaag atgaacttgg acctctgcgg catgttctgg atttgactca aagcaaaagc     300
tttcaattgg aagatgctga gaatttcatc agcaatatca gagtaactgt tgtaaaacta     360
aagggctctg acaacacatt tgagtgccaa ttcgatgatg agtcagcaac tgtggtggac     420
tttctgagga gatggatagc cttctgtcaa agcatcatct caacaagccc tcaaggtggt     480
ggcggttctg gcggtggcgg ttctggtggc ggtggatcct ctatccaggg tacttctctg     540
ctgacccagt ctccggcttc tctgtctacc tacaacgacc agtctgtttc tttcgttctg     600
gaaaacggtt gctacgttat caacgttgac gactctggta agaccaggaa acaggaccag     660
gttctgctgc gttactacga atctccgtgc ccggcttctc agtctggtga cggtgttgac     720
ggtaagaaag ttatggttaa catgtctccg atcaaagaca ccgacatctg gctgcacgct     780
aacgacaaag actactctgt tgaactgcaa cgtggtgacg tttctccgcc ggaacaggct     840
ttcttcgttc tgcacaagaa atcttctgac ttcgtttctt tcgaatgcaa gaacctgccg     900
ggtacttaca tcggtgttaa agacaaccag ctcgctctgg ttgaagagaa agacgaatct     960
tgcaacaaca tcatgttcaa actgtccaaa atctaactcg ag                       1002

<210> SEQ ID NO 11
<211> LENGTH: 323
<212> TYPE: PRT
<213> ORGANISM: Mus musculus

<400> SEQUENCE: 11

Gly Ala Pro Thr Ser Ser Thr Ser Ser Ser Thr Ala Glu Ala Gln
1               5                   10                  15

Gln Gln Gln Gln Gln Gln Gln Gln Gln Gln Gln His Leu Glu Gln Leu
                20                  25                  30
```

-continued

```
Leu Met Asp Leu Gln Glu Leu Leu Ser Arg Met Glu Asn Tyr Arg Asn
        35                  40                  45
Leu Lys Leu Pro Arg Met Leu Thr Phe Lys Phe Tyr Leu Pro Lys Gln
    50                  55                  60
Ala Thr Glu Leu Lys Asp Leu Gln Cys Leu Glu Asp Glu Leu Gly Pro
65                  70                  75                  80
Leu Arg His Val Leu Asp Leu Thr Gln Ser Lys Ser Phe Gln Leu Glu
                85                  90                  95
Asp Ala Glu Asn Phe Ile Ser Asn Ile Arg Val Thr Val Val Lys Leu
            100                 105                 110

Lys Gly Ser Asp Asn Thr Phe Glu Cys Gln Phe Asp Asp Glu Ser Ala
        115                 120                 125

Thr Val Val Asp Phe Leu Arg Arg Trp Ile Ala Phe Cys Gln Ser Ile
    130                 135                 140

Ile Ser Thr Ser Pro Gln Gly Gly Gly Gly Ser Gly Gly Gly Gly Ser
145                 150                 155                 160
Gly Gly Gly Gly Ser Ser Ile Gln Gly Thr Ser Leu Leu Thr Gln Ser
                165                 170                 175
Pro Ala Ser Leu Ser Thr Tyr Asn Asp Gln Ser Val Ser Phe Val Leu
            180                 185                 190
Glu Asn Gly Cys Tyr Val Ile Asn Val Asp Asp Ser Gly Lys Asp Gln
        195                 200                 205
Glu Gln Asp Gln Val Leu Leu Arg Tyr Tyr Glu Ser Pro Cys Pro Ala
    210                 215                 220
Ser Gln Ser Gly Asp Gly Val Asp Gly Lys Lys Val Met Val Asn Met
225                 230                 235                 240
Ser Pro Ile Lys Asp Thr Asp Ile Trp Leu His Ala Asn Asp Lys Asp
                245                 250                 255
Tyr Ser Val Glu Leu Gln Arg Gly Asp Val Ser Pro Pro Glu Gln Ala
            260                 265                 270
Phe Phe Val Leu His Lys Lys Ser Ser Asp Phe Val Ser Phe Glu Cys
        275                 280                 285
Lys Asn Leu Pro Gly Thr Tyr Ile Gly Val Lys Asp Asn Gln Leu Ala
    290                 295                 300
Leu Val Glu Glu Lys Asp Glu Ser Cys Asn Asn Ile Met Phe Lys Leu
305                 310                 315                 320
Ser Lys Ile
```

FUSION PROTEIN COMPRISING INTERLEUKIN-2 AND INTERLEUKIN-33

CROSS REFERENCE TO RELATED APPLICATIONS

This application is a national stage filing of International Application No. PCT/US2014/056767, filed Sep. 22, 2014, which claims benefit of priority pursuant to 35 U.S.C. §119(e) to U.S. provisional patent application No. 61/880,257, filed on Sep. 20, 2013. The entire disclosures of the afore-mentioned patent applications are incorporated herein by reference.

BACKGROUND

Although, IL-2 was discovered more than three decades ago, novel functions of this pleiotropic cytokine are still being discovered (1). These include the role of IL-2 in maintenance of immune tolerance and regulation of T-helper cell (Th) function for organ-specificity of inflammation (14-18). The current invention pertains to the utilization of IL-2 in conjunction with a recently described cytokine IL-33.

Regulatory T-Cells and IL-2:

The Foxp3$^+$CD4$^+$ Regulatory T-cells (Treg) are important for peripheral tolerance and the deficiency of Treg cells has been demonstrated to be an underlying factor for several autoimmune and inflammatory diseases (3-5). The differentiation, survival and the function of the Treg cells is critically dependent on Interleukin-2 (IL-2) (19-22). Mice that are deficient in IL-2 have reduced proportions and numbers of Treg cells. Consequently, there is uncontrolled activation of immune cells leading to a lymphoproliferative disorder, multi-organ inflammation and death between 1 to 4 months of life compared to the normal mice (14-16, 18).

IL2 and Th2 Cells:

IL-2 is produced by the immune cells (mainly T-cells) and supports the homeostasis and function of another important cell-type of the immune system known as Th2 cells. IL-2 regulates the development and function of the Th2 cells in vivo (14, 16). The primary function of the Th2 cells is to fight parasitic infections and boost the production of anti-parasitic antibodies by the B-cells. However, they have also been known to suppress organ-specific inflammation during autoimmunity, observed in type 1 diabetes (T1D; also referred to as diabetes mellitus type 1) and multiple sclerosis (MS) (23-26). The Th2 cells have also been recognized as potent suppressors of Th1 cells and cytolytic T-cells that induce organ rejection during transplantation (27-31).

Treg Independent Anti-Inflammatory Functions of IL-2:

IL-2 has been shown to be important negative regulator of inflammation via regulating Treg homeostasis and function. Recent studies demonstrated the important function of IL-2 in preventing organ-specific inflammation independent of its role in Treg cells, via regulating the phenotype and function of the Th cells, which in-turn regulates the B-cell responses. The IL2-/- (IL2 knock-out (KO)) mice have much reduced Tregs that leads to spontaneous inflammation in pancreas, salivary glands, and liver (14-16). However, the Scurfy (Sf) mice, which are completely deficient in Tregs due to mutation in Foxp3 (the lineage regulator of Tregs), are resistant to inflammation in the pancreas, salivary glands, liver etc, although they develop multi-organ inflammation in the skin, lungs and stomach (14-16).

Deleting the IL-2 gene from the scurfy mice (the Sf.Il2-/- double mutant mice) induced pancreatitis, sialoadenitis, and hepato-cholangitis, suggesting that IL-2 suppresses inflammation in these organs independent of Tregs (14-16). However, deficiency of other suppressive cells (such as Th2) due to loss of IL-2 may further exacerbate the disease.

The involvement of the organs is reminiscent of an increasing number of patients who have autoimmune pancreatitis (AIP). These patients also have parallel or subsequent inflammation in salivary glands, hepato-biliary tree, and several other organs (Khosroshahi & Stone, A clinical overview of IgG4-related systemic disease Curr. Opin. Rheumatol., 2011, 23(1):57-66). The diseases has now been identified as a spectrum disorder, known as IgG4-related systemic disease (IgG4-RSD). These patients have elevated levels of IgG4 systemically as well as in the inflamed organs. The production of IgG4 during autoimmunity and IgE during allergic diseases is a result of increased TfH cell activity, which induces class-switching and somatic hypermutation in the B-cells. Our data implies that IL-2 is a negative regulator of several genes associated with the T-follicular helper cells (TfH), which are critical for the maturation of B-cells and for production of high-affinity antibodies (manuscript in preparation). Recent data from other groups also showed that IL-2 via STAT5 is a negative regulator of TfH cell differentiation (32, 33).

A strong correlation comes from Lupus patients, whose T-cells produce less IL-2, and show an increase in the TfH-mediated germinal center formation and increased production of autoantibodies (34). Data from T1D patients as well as non-obese diabetic (NOD) mouse models show strong correlations of hypomorphic variations in the IL-2 and IL-2 receptor (CD25) alleles (35). Similarly, in multiple sclerosis (MS), one of the strongest genetic correlations has been linked to the hypomorphic alleles of IL-2R (36, 37). The pro-inflammatory cytokine—IFN-γ produced by Th1 cells, is increased systemically as well as locally at the sites of inflammation in all these diseases.

Interestingly, a strong Th2 response was associated with lower incidence and well as resolution of T1D and MS in the human patients as well as mouse models (23-26). Treatment of mice with conditions that promote the Th2 immunity was found to be beneficial in several mouse models (23, 38-40).

IL-2 and Innate Lymphoid Cells (ILC):

A new subset of lymphocytes has been identified recently by several independent groups and has been named ILC, Nuocytes, and natural helper cells (9, 12, 13, 41). These cells do not express the characteristic cell surface markers of T- and B-lymphocytes and mainly reside at the mucosal surfaces and offer first line of defense against parasites. However, they express several cell surface molecules, such as CD90, c-Kit and IL-7Ra, indicative of their lymphoid origin. They also express high levels of CD25 (IL-2Ra) and T1/ST2 (IL-33R) (42-44). Stimulation of lung ILCs with IL-33 in combination with IL-2 and IL-7 resulted in production of IL-5 and IL-13, demonstrating that the ILC population in the lung resembles Type 2 ILCs that express Th2-associated cytokines (45, 46).

IL-33, ILC, and Th2 Cells:

IL-33 was discovered recently and is synthesized as a 270 amino acid protein that contains a nuclear localization signal (NLS) at the N-terminus and a C-terminal region with structural homology to IL-1 family cytokines (47-49). Full length IL-33 localizes to the nucleus where it associates with heterochromatin and mitotic chromosomes and may function as a transcriptional repressor (47-49). The intracellular apoptosis related protease Caspase-1 cleaves IL-33 to an 18 kDa C-terminal fragment, which has structure and functions similar to the IL-1 family cytokines. IL-33 expression was found upregulated in innate immune and epithelial cells in response to parasitic infections (50, 51).

The receptor for IL-33, IL1RL1 (also known as ST2), was identified long before the discovery of IL-33 and was considered an orphan receptor present on the surface of Th2 cells until the discovery of IL-33 (52, 53). IL-33 induces hetero-dimerization of IL1RL1 with IL-1RAcP, the co-receptor for IL-1 and IL-18. IL-33 is also considered an alarmin, which is released by cells undergoing apoptosis to induce clearance of the dying cells (52).

The ILC/Nuocytes, as well as Th2 cells, when stimulated with IL-33 upregulate the expression of IL-4, IL-5, and IL-13, the critical cytokines for the effector function of these cells against parasitic infections. Recent studies show that IL-33 promotes the function of ILC/Nuocytes as a first line of defense, before the adaptive immunity matures (12, 45, 54). Recent data also suggests that IL-33 production by the dendritic cells in response to allergens may be one of the mechanisms to initiate a Th2 response (55-57).

Anti-Inflammatory Role of IL-33:

Although, the primary function of IL-33 has been adjudged to boost the immunity against parasitic infections, recent data has identified several anti-inflammatory properties of IL-33. Several of these studies indicate a skewing towards the Th2-type of response, which results in resolution of the pro-inflammatory Th1 and Th17 responses (10, 58). Besides being chemo-attractive for and promoting the secretion of Th2 cytokines (IL-5 and IL-13) by the differentiated Th2 cells, IL-33 can prime murine dendritic cells to induce polarization of naïve T cells towards a Th2 phenotype (55-57). Further, IL-33 has been shown to enhance production of IgM antibodies and IL-5 and IL-13 production from B1 B-cells in vivo (59).

The natural IgM secreted by the B1 B-cells is widely accepted as anti-inflammatory under various settings (60, 61). In experimental asthma in the ovalbumin-induced airway inflammation model, the IL-33 receptor-deficient mice were not protected (62). Interestingly, in another model adoptive transfer of IL1RL1-deficient Th2 cells into immuno-deficient Rag1 KO mice induced greater disease than the IL1RL1-sufficient control mice (63).

Several inflammatory diseases are driven by IL-12 and IFN-γ-induced Th1 immune response and infiltration of immune cells in the target organs such as atherosclerosis. IL-33 treatment reduced the inflammation both in terms of lesion size as well as in terms of reduction in the infiltrating cells in mouse models of atherosclerosis (64, 65). This was accompanied with a switch in the cytokine profile from INF-γ to IL-4, IL-5, and IL-13 along with an increase in the levels of protective anti-oxidized low-density lipoprotein (ox-LDL) IgM antibodies. On the other hand, blocking the signaling with the use of soluble IL1RL1 (sST2) worsened the disease with high IFN-γ levels (66).

IL-33 has been shown to have important functions in the central nervous system (CNS), as indicated by strong expression of its mRNA in the brain and spinal cord and the levels are further increased under experimental inflammatory conditions (67, 68). The microglial and astrocytes also express the IL-33 receptor as detected by flow-cytometry (69). LPS stimulation of cultured microglia and astrocytes induced the expression of IL-33 in glial and astrocyte cultures. IL-33 treatment not only induced proliferation of microglial cells, but also induced the phagocytosis and secretion of IL-10, IL-10, and TNF-α by these cells (69). Finally, a transcriptional analysis of brain tissue from patients with Alzheimer's disease revealed that IL-33 expression was decreased compared to control tissues, suggesting that IL-33 may play an important neuroprotective role during infections and inflammatory conditions (70).

IL-33/IL1RL1 axis has recently been shown to be protective in type-2 diabetes (T2D). In vitro culture of adipocytes with IL-33 induced production of Th2 cytokines leading to reduced lipid storage and decreased expression of several adipogenesis related genes (71). In vivo, treatment of genetically obese diabetic mice (ob/ob) with IL-33 led to protective metabolic effects with reduced adiposity, reduced fasting glucose, and improved glucose and insulin tolerance. Conversely, mice lacking IL1RL1 were more susceptible to T2D upon high fat diet feeding as compared to the controls. The protection offered by IL-33 signaling was accompanied via switch in phenotype of macrophages from M1 (Th1 associated pro-inflammatory) to M2 (Th2 associated anti-inflammatory) (71). Recent studies have also shown that IL-33 can induce the Fat-associated lymphoid cells (FALC) to secrete IL-4, IL-5 and IL-13, which may be serve a protective role against inflammation during obesity (72).

There is a long felt need in the art for compositions and methods useful for treating autoimmune diseases and disorders and inflammation. The present application satisfies these needs.

SUMMARY OF THE INVENTION

The invention encompassed by the present application was conceived based on the disclosure herein that the receptors for the cytokines IL-2 and IL-33 are co-expressed on subsets of immune cells that are important for boosting immunological tolerance. The present invention is useful in enhancing host immunity to parasitic infections. As disclosed herein, Treg, Th2, and the more recently discovered innate lymphoid cells, (ILC2), express high levels of the receptors for IL-2 and IL-33. Based on the data disclosed herein, the present invention encompasses a combination therapy with IL-2 and IL-33, or a therapy with a novel fusion protein comprising active fragments of IL-2 and IL-33, to simultaneously promote Treg and Th2 responses to offer long-term protection against autoimmunity and inflammation by suppressing the Th1 and Th17 responses, as well as inhibiting activation of several other pro-inflammatory immune cells. The novel cytokine/fusion protein disclosed herein has the activities of both IL-2 and IL-33 in one molecule. This strategy is designed to increase the specificity of the IL-2 and IL-33 activities by targeting them to cell-types that are simultaneously enriched for the receptors for both the cytokines and to increase the binding affinity of the novel cytokine through cooperativity. Interestingly, the ILC/Nuocytes are critically dependent on IL-2 because their numbers are drastically reduced in the IL-2 deficient mice (data not presented).

The present application discloses the combination of action of two pleiotropic cytokines, IL-2 and IL-33, wherein their use as a combination results in a robust and long-lasting modulation of the immune response to simultaneously boost multiple anti-inflammatory mechanisms, the most important being the expansion of the T-regulatory cell population, which is the major enforcer of peripheral immune tolerance. In one aspect, the combination is additive. In one aspect, the result seen with the combination is unexpectedly synergistic relative to the effect seen when either is used alone.

Without wishing to be bound by any particular theory, it is hypothesized herein that loss of adequate levels of IL-2 increases TfH differentiation and thereby induces generation of the IgG4-secreting plasma cells. Additionally, deficiency of IL-2 causes reduction in the Th2 cytokines IL-4, IL-5, and IL-13. The lack of Th2 cytokines coupled with the increase TfH further induces the class switching of antibodies towards more of IgG4 production. Thus, IL-2 plays important role in the organ-specific autoimmune diseases directly by regulating Treg, by regulating Th2 response and by regulating TfH induced autoantibody production.

This invention describes a novel therapeutic approach for the treatment of autoimmune and inflammatory diseases by using a combination of two cytokines that promote anti-inflammatory responses and immune-tolerance. This therapy can be employed for boosting multiple inherent protective mechanisms against autoimmune and inflammatory diseases. The combination therapy is designed to be more specific and with fewer side effects by combining the activities in one hybrid molecule.

Interleukin (IL)-2 is a pleiotropic cytokine, which is important for the survival and function of several subsets of Thelper (Th) cells (1). Two of these Th cell subsets, known as T-regulatory cells (Tregs) and Th2 cells are critical for the suppression of systemic and organ-specific inflammation associated with autoimmunity and infection (2-8). Both the Tregs and Th2 cells constitutively express the high-affinity receptor for IL-2, known as IL-2Ra (CD25) and are critically dependent on IL-2 for survival and function. Both T-cell subsets also express high-levels of IL1RL1 (data not presented)—the receptor for a newly described cytokine—IL-33, which is not only critical for the proliferation and adequate function of Th2 cells (9), but has recently been shown to support proliferation and function of Treg cells (10, 11). Although several cell types express CD25 and IL-33, the Treg and Th2 cells are especially enriched for the co-expression of receptors for both of these cytokines. Disclosed herein is the unexpected result of the synergy of IL-2 and IL-33 to protect against autoimmune and inflammatory disorders as opposed to the use of either cytokine alone.

To better utilize the multiple effects of IL-2 and IL-33, disclosed herein is a novel fusion protein (termed IL233) that has activities of both IL-2 and IL-33. The IL233 fusion protein can be used to expand the existing pool of Treg and Th2 cells to suppress inflammation mediated by the Th1 and Th17 cells for prevention or therapy of various inflammatory disorders that occur due to autoimmunity, transplantation, and Ischemia Reperfusion Injury (IRI) and infections. In one aspect, the IL233 fusion protein disclosed herein provides for better targeting of the activities of the proteins (by separating them with a linker sequence) to the Tregs and other anti-inflammatory cells. The anti-inflammatory mechanisms, thus invoked, can be used for therapy of a broad range of autoimmune and inflammatory diseases. Thus, the fusion peptide of the invention can bind to two receptors, resulting in a peptide with two separate activities based on the interaction with two different receptors. Further disclosed herein are the unexpected results of a synergistic effect of the combination of IL-2 and IL-33 in one fusion peptide.

The invention further encompasses different ways to join IL-2 and IL-33 and their activities. For example, IL-2 and IL-33 activities could also be linked to each other chemically by covalent or non-covalent methods, or by co-immobilization (absorption/adsorption) on a carrier, which could be a cell, a liposome, a nanoparticle or matrix.

The application further discloses not just effects of these molecules in vitro and mechanisms of action, but further tests the molecules in vivo. Combinations of the two cytokines and use of the novel fusion molecule demonstrate efficacy in autoimmune type-1 diabetes, acute kidney injury occurring due to ischemia reperfusion, autoimmune lupus glomerulonephritis, obesity-linked Type-2 diabetes, obesity, hyperglycemia, and diabetic nephropathy.

A recently identified subset of cells known as innate lymphoid cells (ILC) or Nuocytes has been recognized as the first line of defense against parasitic infections. Interestingly, the ILC/Nuocytes are also critically dependent on IL-2 and IL-33 for their survival and function (12, 13). The Nuocytes work in close collaboration with the Th2 cells to fight parasitic pathogens (13). One of ordinary skill in the art will appreciate that, based on the disclosure provide herein, IL233 can be used for multiple purposes, including but not limited to, boosting immunity against parasitic infections by promoting both Nuocytes and Th2 cells.

In one embodiment, the present invention provides a fusion protein consisting of an IL-2 fragment and an IL-33 fragment. In one aspect, the IL-2 fragment comprises residues 21-153 of human IL-2. In one aspect, the IL-33 fragment comprises residues 112-270 of human IL-33. In one aspect, the fusion protein comprises an IL-2 and an IL-33 fragment separated by a short linker sequence. In one aspect, the linker sequence is GGGGSGGGGSGGGGS (SEQ ID NO:5). The fusion protein is named IL233 and the human version as used is disclosed below and can be referred to as hIL233. A murine version (mIL233) is also provided below.

Summary of Sequences of the Invention

SEQ ID NO:1—Nucleic Acid Sequence for novel IL233 encoding the human fusion protein of SEQ ID NO:2

```
GAATTCGAGAACCTGTACTTCCAGGGTGCTCCGACCTCTTCTTCTACCAA
GAAAACCCAGCTGCAGCTGGAACACCTGTTGCTGGACCTGCAGATGATCC
TGAACGGTATCAATAACTACAAGAACCCGAAACTGACCCGTATGCTGACC
TTCAAATTCTACATGCCGAAGAAAGCTACCGAACTGAAACACCTGCAGTG
CCTGGAAGAGGAACTGAAACCGCTGGAAGAAGTTCTGAACCTGGCTCAGT
CTAAGAACTTCCACCTGCGTCCGCGTGACCTGATCTCTAACATCAACGTT
ATCGTTCTGGAACTGAAAGGTTCTGAAACCACCTTCATGTGCGAATACGC
TGACGAAACCGCTACCATCGTTGAGTTCCTGAACCGTTGGATCACCTTCT
GCCAGTCTATCATCTCTACCCTGACCGGTGGTGGCGGTTCTGGCGGTGGC
GGTTCTGGTGGCGGTGGATCCAGCATCACCGGCATCAGCCCCATCACCGA
GTACCTGGCCAGCCTGAGCACCTACAACGACCAGAGCATCACCTTCGCCC
TGGAGGACGAGAGCTACGAGATCTACGTGGAGGACCTGAAGAAGGACGAG
AAGAAGGACAAGGTGCTGCTGAGCTACTACGAGAGCCAGCACCCCAGCAA
CGAGAGCGGCGACGGCGTGGACGGCAAGATGCTGATGGTGACCCTGAGCC
CCACCAAGGACTTCTGGCTGCACGCCAACAACAAGGAGCACAGCGTGGAG
CTGCACAAGTGCGAGAAGCCCCTGCCCGACCAGGCCTTCTTCGTGCTGCA
CAACATGCACAGCAACTGCGTGAGCTTCGAGTGCAAGACCGACCCCGGCG
TGTTCATCGGCGTGAAGGACAACCACCTGGCCCTGATCAAGGTGGACAGC
AGCGAGAACCTGTGCACCGAGAACATCCTGTTCAAGCTGAGCGAGACCTA
ACTCGAG
```

SEQ ID NO:2—amino acid sequence (308 residues) of the human IL233 fusion protein (the underlined section denotes the sequence encoding the IL-2 fragment, the bold-face sequence denotes the linker segment and the remainder is the sequence encoding the IL-33 fragment)

GAPTSSSTKKTQLQLEHLLLDLQMILNGINNYKNPKLTRMLTFKFYMPKK
ATELKHLQCLEEELKPLEEVLNLAQSKNFHLRPRDLISNINVIVLELKGS
ETTFMCEYADETATIVEFLNRWITFCQSIISTLTGGGGSGGGGSGGGGS
ITGISPITEYLASLSTYNDQSITFALEDESYEIYVEDLKKDEKKDKVLLS
YYESQHPSNESGDGVDGKMLMVTLSPTKDFWLHANNKEHSVELHKCEKPL
PDQAFFVLHNMHSNCVSFECKTDPGVFIGVKDNHLALIKVDSSENLCTEN
ILFKLSET

SEQ ID NO:3—the 134 amino acid residue fragment of human IL-2 used in SEQ ID NO:2

GAPTSSSTKKTQLQLEHLLLDLQMILNGINNYKNPKLTRMLTFKFYMPKK
ATELKHLQCLEEELKPLEEVLNLAQSKNFHLRPRDLISNINVIVLELKGS
ETTFMCEYADETATIVEFLNRWITFCQSIISTLT

SEQ ID NO:4—the 159 amino acid residue fragment of human IL-33 used in SEQ ID NO:2

SITGISPITEYLASLSTYNDQSITFALEDESYEIYVEDLKKDEKKDKVLL
SYYESQHPSNESGDGVDGKMLMVTLSPTKDFWLHANNKEHSVELHKCEKP
LPDQAFFVLHNMHSNCVSFECKTDPGVFIGVKDNHLALIKVDSSENLCTE
NILFKLSET

SEQ ID NO:5—the 15 amino acid residue linker sequence used in SEQ ID NO:2

GGGGSGGGGSGGGGS

SEQ ID NO:6—full length human IL-2 protein, 153 a.a., GenBank accession number—P60568

MYRMQLLSCIALSLALVTNSAPTSSSTKKTQLQLEHLLLDLQMILNGINN
YKNPKLTRMLTFKFYMPKKATELKHLQCLEEELKPLEEVLNLAQSKNFHL
RPRDLISNINVIVLELKGSETTFMCEYADETATIVEFLNRWITFCQSIIS
TLT

SEQ ID NO:7—full length human IL-33 full length protein, 270 a.a., GenBank accession number O95760

MKPKMKYSTNKISTAKWKNTASKALCFKLGKSQQKAKEVCPMYFMKLRSG
LMIKKEACYFRRETTKRPSLKTGRKHKRHLVLAACQQQSTVECFAFGISG
VQKYTRALHDSSITGISPITEYLASLSTYNDQSITFALEDESYEIYVEDL
KKDEKKDKVLLSYYESQHPSNESGDGVDGKMLMVTLSPTKDFWLHANNKE
HSVELHKCEKPLPDQAFFVLHNMHSNCVSFECKTDPGVFIGVKDNHLALI
KVDSSENLCTENILFKLSET

SEQ ID NO:8—murine IL-2 full length protein, 169 a.a., GenBank accession number P04351

MYSMQLASCVTLTLVLLVNSAPTSSSTSSSTAEAQQQQQQQQQQQQHLEQ
LLMDLQELLSRMENYRNLKLPRMLTFKFYLPKQATELKDLQCLEDELGPL
RHVLDLTQSKSFQLEDAENFISNIRVTVVKLKGSDNTFECQFDDESATVV
DFLRRWIAFCQSIISTSPQ

SEQ ID NO:9—murine IL-33 full length protein, 266 a.a., GenBank accession number Q8BVZ5

MRPRMKYSNSKISPAKFSSTAGEALVPPCKIRRSQQKTKEFCHVYCMRLR
SGLTIRKETSYFRKEPTKRYSLKSGTKHEENFSAYPRDSRKRSLLGSIQA
FAASVDTLSIQGTSLLTQSPASLSTYNDQSVSFVLENGCYVINVDDSGKD
QEQDQVLLRYYESPCPASQSGDGVDGKKLMVNMSPIKDTDIWLHANDKDY
SVELQRGDVSPPEQAFFVLHKKSSDFVSFECKNLPGTYIGVKDNQLALVE
EKDESCNNIMFKLSKI

SEQ ID NO:10—murine fusion IL233 nucleic acid sequence encoding the murine IL233 fusion peptide of SEQ ID NO:11

GAATTCGAGAACCTGTACTTCCAGGGTGCACCCACTTCAAGCTCCACTTC
AAGCTCTACAGCGGAAGCACAGCAGCAGCAGCAGCAGCAGCAGCAGCAGC
AGCAGCACCTGGAGCAGCTGTTGATGGACCTACAGGAGCTCCTGAGCAGG
ATGGAGAATTACAGGAACCTGAAACTCCCCAGGATGCTCACCTTCAAATT
TTACTTGCCCAAGCAGGCCACAGAATTGAAAGATCTTCAGTGCCTAGAAG
ATGAACTTGGACCTCTGCGGCATGTTCTGGATTTGACTCAAAGCAAAAGC
TTTCAATTGGAAGATGCTGAGAATTTCATCAGCAATATCAGAGTAACTGT
TGTAAAACTAAAGGGCTCTGACAACACATTTGAGTGCCAATTCGATGATG
AGTCAGCAACTGTGGTGGACTTTCTGAGGAGATGGATAGCCTTCTGTCAA
AGCATCATCTCAACAAGCCCTCAAGGTGGTGGCGGTTCTGGCGGTGGCGG
TTCTGGTGGCGGTGGATCCTCTATCCAGGGTACTTCTCTGCTGACCCAGT
CTCCGGCTTCTCTGTCTACCTACAACGACCAGTCTGTTTCTTTCGTTCTG
GAAAACGGTTGCTACGTTATCAACGTTGACGACTCTGGTAAAGACCAGGA
ACAGGACCAGGTTCTGCTGCGTTACTACGAATCTCCGTGCCCGGCTTCTC
AGTCTGGTGACGGTGTTGACGGTAAGAAAGTTATGGTTAACATGTCTCCG
ATCAAAGACACCGACATCTGGCTGCACGCTAACGACAAAGACTACTCTGT
TGAACTGCAACGTGGTGACGTTTCTCCGCCGGAACAGGCTTTCTTCGTTC
TGCACAAGAAATCTTCTGACTTCGTTTCTTTCGAATGCAAGAACCTGCCG
GGTACTTACATCGGTGTTAAAGACAACCAGCTCGCTCTGGTTGAAGAGAA
AGACGAATCTTGCAACAACATCATGTTCAAACTGTCCAAAATCTAACTCG
AG

SEQ ID NO:11—murine IL233 (mIL233) fusion protein amino acid sequence (323 amino acid residues)

GAPTSSSTSSSTAEAQQQQQQQQQQQQHLEQLLMDLQELLSRMENYRNLK

LPRMLTFKFYLPKQATELKDLQCLEDELGPLRHVLDLTQSKSFQLEDAEN

FISNIRVTVVKLKGSDNTFECQFDDESATVVDFLRRWIAFCQSIISTSPQ

GGGGSGGGGSGGGGSSIQGTSLLTQSPASLSTYNDQSVSFVLENGCYVIN

VDDSGKDQEQDQVLLRYYESPCPASQSGDGVDGKKVMVNMSPIKDTDIWL

HANDKDYSVELQRGDVSPPEQAFFVLHKKSSDFVSFECKNLPGTYIGVKD

NQLALVEEKDESCNNIMFKLSKI

The invention provides an isolated protein comprising a IL-2/IL-33 fusion molecule. Preferably, the isolated polypeptide comprising a mammalian IL-2/IL-33 fusion molecule is at least about 30% homologous to a polypeptide having the amino acid sequence of at least one of SEQ ID NO:2, SEQ ID NO:4, SEQ ID NO:6, SEQ ID NO:8, and SEQ ID NO:11. Preferably, the isolated polypeptide is at least about 35% homologous, more preferably, about 40% homologous, more preferably, about 45% homologous, even more preferably, about 50% homologous, more preferably, about 55% homologous, preferably, about 60% homologous, more preferably, about 65% homologous, even more preferably, about 70% homologous, more preferably, about 75% homologous, even more preferably, about 80% homologous, preferably, about 85% homologous, more preferably, about 90% homologous, even more preferably, about 95% homologous, and most preferably, about 99% homologous to at least one of SEQ ID NO:2, SEQ ID NO:4, SEQ ID NO:6, SEQ ID NO:8, and SEQ ID NO:11.

In one aspect, the invention provides a fusion protein comprising a biologically active domain of Interleukin-2 (IL-2) or a biologically active fragment or homolog thereof, wherein the domain binds with the IL-2 receptor. Additionally, the fusion protein comprises a biologically active domain of Interleukin-33 (IL-33) or a biologically active fragment or homolog thereof, wherein the IL-33 domain binds with the IL-33 receptor. In one aspect, the IL-2 domain is linked to the IL-33 domain with a linker sequence. In one aspect, the linker comprises the sequence of SEQ ID NO:5 or a substantially homologous sequence.

In one aspect, the fusion protein comprises the amino acid sequence of SEQ ID NO:2 or SEQ ID NO:11 or a biologically active substantially homologous sequence.

In one aspect, the IL-2 portion of the fusion protein comprises the sequence of SEQ ID NO:6 or SEQ ID NO:8 and the IL-33 portion comprises the sequence of SEQ ID NO:7 or SEQ ID NO:9, or biologically active fragments or homologs thereof.

In one aspect, the IL-2 fragment comprises the sequence of SEQ ID NO:3, and the IL-33 fragment comprises the sequence of SEQ ID NO:4, or biologically active fragments or homologs thereof. In one aspect, the homolog of SEQ ID NO:3 is selected from a group comprising at least 75, 80, 85, 90, and 95% homology with SEQ ID NO:3 and the homolog of SEQ ID NO:4 is selected from a group comprising at least 75, 80, 85, 90, and 95% homology with SEQ ID NO:4.

In one aspect, the fusion protein is a synthetic protein.

The present invention encompasses an isolated nucleic acid encoding a protein, wherein the protein is a fusion of active full-length sequences, fragments, or homologs of IL-2 and IL-33. In one aspect, the IL-2 portion or fragment is the first portion of the protein (amino terminus). In one aspect, the IL-2 portion or fragment is second. In one aspect, there is a linking sequence between the IL-2 portion or fragment and the IL-33 portion or fragment. In one aspect, the protein is human.

The present invention includes an isolated nucleic acid encoding a mammalian fusion IL-2/IL-33 protein molecule, or a fragment thereof, wherein the nucleic acid shares at least about 30% identity with at least one nucleic acid having the sequence of SEQ ID NO:1 or SEQ ID NO:11. Preferably, the nucleic acid is at least about 35% homologous, more preferably, about 40% homologous, more preferably, about 45% homologous, even more preferably, about 50% homologous, more preferably, about 55% homologous, preferably, about 60% homologous, more preferably, about 65% homologous, even more preferably, about 70% homologous, more preferably, about 75% homologous, even more preferably, about 80% homologous, preferably, about 85% homologous, more preferably, about 90% homologous, even more preferably, about 95% homologous, and most preferably, about 99% homologous to SEQ ID NO:1 or 11 disclosed herein. Even more preferably, the nucleic acid is SEQ ID NO:1 or 11.

In one embodiment, the invention provides an isolated nucleic acid comprising a nucleic acid sequence encoding a fusion protein of the invention. In one aspect, the invention provides an isolated nucleic acid comprising a nucleic acid sequence encoding a fusion peptide having the sequence of SEQ ID NOs: 2 or 11, or biologically active fragments or homologs thereof.

In one embodiment, the isolated nucleic acid comprises the sequence of SEQ ID NOs:1 or 10.

The present invention further provides a vector comprising an isolated nucleic acid comprising a nucleic acid sequence encoding a fusion protein of the invention and optionally a promoter. In one aspect, the vector is selected from the group consisting of a bacterial vector, a viral vector, and a mammalian vector. In one aspect, the invention provides for administering the nucleic acid to a subject or to a cell. In one aspect, the isolated nucleic acid is useful for autologous cell therapy. The invention further provides a recombinant host cell comprising an isolated nucleic acid of the invention and a recombinant host cell comprising a vector the invention.

The present invention provides a fusion protein encoded by an isolated nucleic of the invention.

In one embodiment, the invention provides a transgenic non-human mammal comprising an isolated nucleic acid encoding an IL-2/IL-33 fusion protein or fragment or homolog thereof. In one aspect, the isolated nucleic acid comprises the sequence of SEQ ID NO:1 or 11.

In one embodiment, the present invention provides compositions and methods for promoting/activating and stimulating proliferation of cells. In one aspect, the present invention provides compositions and methods for stimulating proliferation of T-regulatory (Treg), Thelper2 (Th2), and innate lymphoid cells (ILC) cells. In one aspect, the present invention provides compositions and methods for activating Treg, Th2 and ILC cells. In one aspect, the method comprises contacting the cells with an effective amount of an IL233 fusion protein or a combination of Interleukin-2 (IL-2) and Interleukin-33 (IL-33) proteins, or biologically active fragments or homologs thereof. In one aspect, the invention provides for use of a pharmaceutical composition comprising a pharmaceutically acceptable carrier and an effective amount of an IL233 fusion protein or a combination of Interleukin-2 (IL-2) and Interleukin-33 (IL-33) proteins, or biologically active fragments or homologs thereof, and optionally an additional therapeutic agent, wherein the composition is used to contact cells or is administered at least once to a subject in need thereof. In one aspect, the IL233 fusion protein, or a biologically active homolog or fragment thereof, comprises a fragment of IL-2 that binds to an IL-2 receptor and a fragment of IL-33 that binds with the IL-33 receptor. In one aspect, the IL233 protein comprises the amino acid sequence of SEQ ID NO:2 or SEQ ID NO:11. In one aspect, the IL-2 portion of the protein comprises the sequence of SEQ ID NO:6 or SEQ ID NO:8, and the IL-33 portion comprises the sequence of SEQ ID NO:7 or SEQ ID NO:9, or biologically active fragments or homologs thereof.

The present invention further provides compositions and methods for treating diseases and disorders. In one aspect, the diseases and disorders are autoimmune. In one aspect, inflammation is associated with the disease or disorder being treated. In one aspect, the invention provides compositions and methods useful for treating a disease or disorder including, but not limited to, diabetic nephropathy, pancreatitis, type 1 diabetes, type 2 diabetes, insulitis, lupus, lupus glomerulonephritis, obesity, acute kidney injury, renal ischemia reperfusion injury, multiple sclerosis, diabetic retinopathy, ankylosing spondylitis, autoimmune cardiomyopathy, autoimmune hemolytic anemia, autoimmune hepatitis, autoimmune lymphoproliferative syndrome, autoimmune pancreatitis, autoimmune polyendocrine syndrome, autoimmune urticaria, autoimmune uveitis, Crohn's disease, dermatomyositis, graft versus host (GVH) disease, Hashimoto's thyroiditis, inflammatory demyelinating diseases, interstitial cystitis, juvenile idiopathic arthritis aka Juvenile rheumatoid arthritis, lupus erythematosus, multiple sclerosis, myasthenia gravis, microscopic colitis, polymyositis, primary biliary cirrhosis, primary sclerosing cholangitis, progressive inflammatory neuropathy, rheumatoid arthritis, Sjögren's syndrome, systemic lupus erythematosus, transplant rejection, ulcerative colitis (one of two types of idiopathic inflammatory bowel disease "IBD"), vasculitis, and Wegener's granulomatosis. In one aspect, the method treats inflammation associated with a disease or disorder of the invention.

In one embodiment, when the subject is being treated for obesity or for obesity-linked diabetes mellitus and related disorders, the method inhibits weight gain, inhibits hyperglycemia, inhibits proteinuria, and restores glucose tolerance.

In one embodiment, the method promotes anti-inflammatory M2 macrophages, inhibits DN-inducing M1 macrophages, and inhibits proteinuria. In another aspect, the method increases Treg levels in the subject.

In one embodiment, the invention provides compositions and methods useful for preventing or treating a disease or disorder of the invention. In one aspect, the method prevents or treats type 1 diabetes, renal ischemia reperfusion injury, or lupus glomerulonephritis.

In one embodiment, an IL233 fusion protein or a combination of Interleukin-2 (IL-2) and Interleukin-33 (IL-33) proteins is administered to a subject in need thereof at a dosage ranging from about 1.0 μg/kg body weight to about 1000 μg/kg body weight. In one aspect, the dosage is from about 10 μg/kg body weight to about 500 μg/kg body weight. In another aspect, the dosage is from about 20 μg/kg body weight to about 100 μg/kg body weight. In a further aspect, the dosage is from about 30 μg/kg body weight to about 50 μg/kg body weight. In one aspect, the dosage is 5.0, 15, 50, or 150 μg/kg of body weight. In one embodiment, the fusion protein can be administered with one or more of the cytokines IL-2 and IL-33. One of ordinary skill in the art can determine the dosage, number of doses, and timing of doses based on the age, sex, weight, and health of the subject.

The present invention further provides compositions and methods for making fusion peptides of the invention and for making isolated nucleic acids comprising sequences encoding the peptides.

In one aspect, a pharmaceutical composition comprising an effective amount of a fusion protein of the invention or a combination of IL-2 and IL-33 proteins, or fragments or homologs thereof, is administered at least twice. In another aspect, a pharmaceutical composition is administered at least five times. In yet another aspect, a pharmaceutical composition is administered at least 10 times. One of ordinary skill in the art can determine how often to administer the composition based on the particular disease or disorder or how the subject has responded to prior treatments.

The present invention further provides a pharmaceutical composition comprising a fusion protein of the invention. The composition optionally comprises a pharmaceutically acceptable carrier. The composition may also optionally comprise an additional therapeutic agent.

The present invention further provides kits. A kit may comprise one or more of the fusion proteins of the invention, an isolated nucleic acid comprising a sequence encoding a fusion protein of the invention, one or more cytokines (IL-2 and IL-33), and a pharmaceutical composition optionally comprising a pharmaceutically acceptable carrier. The kit may also comprise one or more containers, one or more syringes, one or more applicators, and an instructional material for the use thereof.

Various aspects and embodiments of the invention are described in further detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1A:
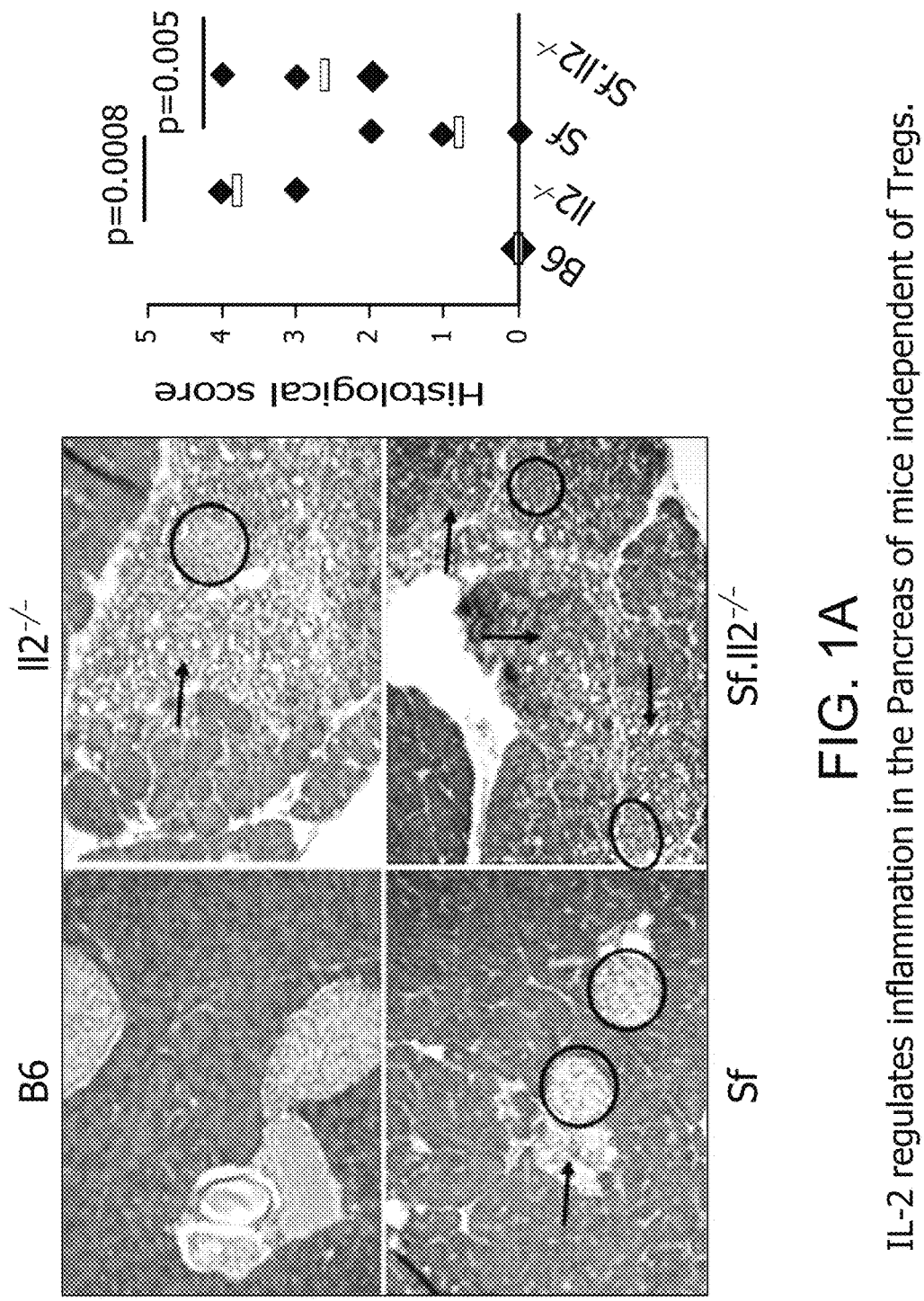
FIG. 1. IL-2 regulates inflammation in the Pancreas of mice independent of Tregs. (A) The Foxp3 mutant scurfy (Sf) mice are completely deficient in Treg cell, yet they are resistant to inflammation in the pancreas despite inflammation in several other organs. An additional deficiency of IL-2 in Sf mice (Sf.Il2$^{-/-}$) results in inflammation in pancreas. The IL-2 deficient mice with a partial Treg deficiency (Il2$^{-/-}$) also develop sever inflammation in pancreas. Islets are marked with ellipses and inflammation is shown with arrows. (B) The pancreas infiltrating cells produce mostly IFNγ and little IL-4 as measured by intracellular staining and flow cytometry on ex vivo restimulation with PMA and Ionomicin. (C) Further, deletion of Th2 response genes IL-4 (Sf.Il4$^{-/-}$) or STAT6 (Sf.Stat6$^{-/-}$), also leads to severe pancreatitis in Treg-deficient mice. Deficiency of IFNγ (Sf.Ifng$^{-/-}$) results in protection against such inflammation. Islets are marked with ellipses and inflammation is shown with arrows.

Non-obese diabetic mice with early diabetes (blood glucose 150±10 mg/dL) were injected daily for five (5.0) consecutive days with 1.0 µg IL-2 or IL-33 or combination of IL-2 and IL-33 or molar equivalent of IL233. The animals were followed over time. The control mice were injected with saline. Six weeks post-treatment, the mice that recovered from hyperglycemia or the mice that were severely diabetic (blood glucose of 600 mg/dL for two consecutive days) were euthanized and the spleen and pancreatic lymph nodes were analyzed for the CD4$^+$Foxp3$^+$ Treg cells. The numbers in the parenthesis show the number of mice analyzed. Please note that the molecular mass of IL233 is greater than that of IL-2 or IL-33 and is approximately the sum of the molecular masses of IL-2 and IL-33. Therefore, for equimolar comparisons two-fold higher quantity of IL233 is used, e.g. for each 1 µg of IL-2 and/or IL-33, 2 µg of IL233 is used.

FIG. 7. Treatment with IL233 or mixture of IL-2 and IL-33 protects C57BL/6 mice from renal ischemia reperfusion injury (IRI). C57BL/6 mice were treated daily for 5 consecutive days with doses of the indicated amounts (0.3, 1.0, or 3.0 µg per animal, i.e., 15, 50, or 150 µg/kg of body weight) of a combination of IL-2 and IL-33 or with molar equivalents (0.1, 0.3 or 1.0 µg, i.e., 5, 15, or 50 µg/kg) IL233 fusion cytokine starting at a one third lower amount than the combination of IL-2 and IL-33. On day 7, the renal pedicle was clamped for 26 minutes followed by 18 hours reperfusion. High plasma creatinine levels indicate loss of kidney function. The IL233 fusion was 3-fold more effective than the mixture of IL-2 and IL-33 in protecting mice against loss of renal function and inflammation as measure by Plasma creatinine levels (A) or Histological score. (B). The protection was accompanied with reduction of the activated CD4$^+$ T cells (C), CD8$^+$ T-cells (not shown) and activated B-cells (D) in the spleen. TNFα producing CD4 (E) and CD8 (F) T-cells and IFN-γ producing cells (not shown) were also reduced by the cytokine treatment as measured by flow cytometry of the cells isolated from the spleen. Please note that the molecular mass of IL233 is greater than that of IL-2 or IL-33 and is approximately the sum of the molecular mass of IL-2 and IL-33. Therefore for equimolar comparisons two-fold higher quantity of IL233 is used, e.g. for each 1 µg of IL-2 and/or IL-33, 2 µg of IL233 is used.

Figure 8A:
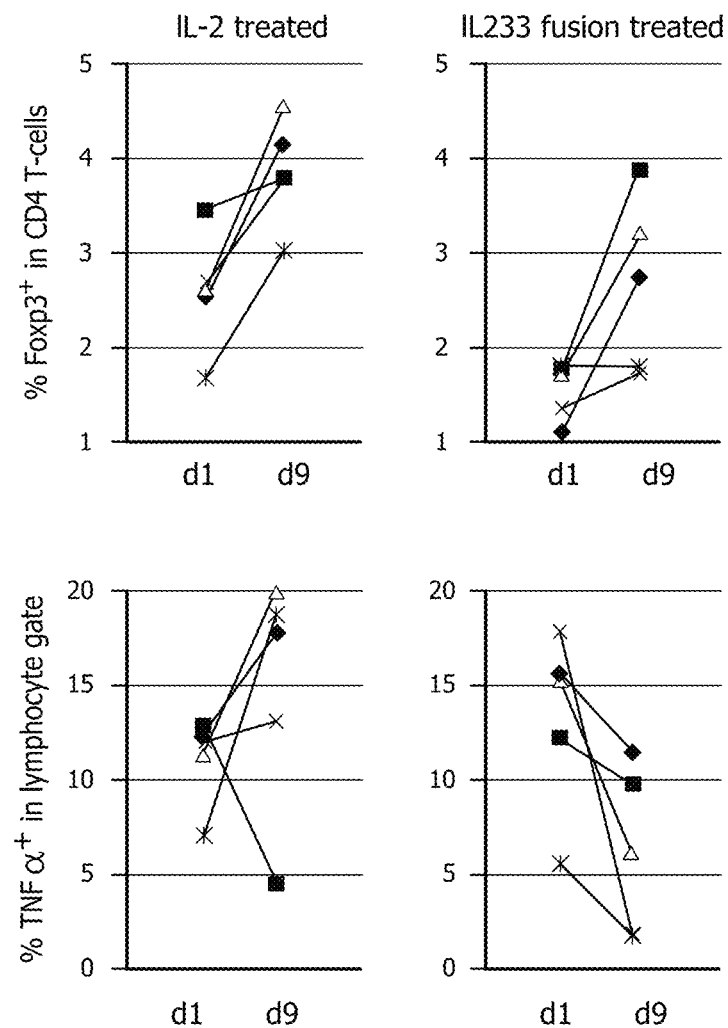
Figure 8B:
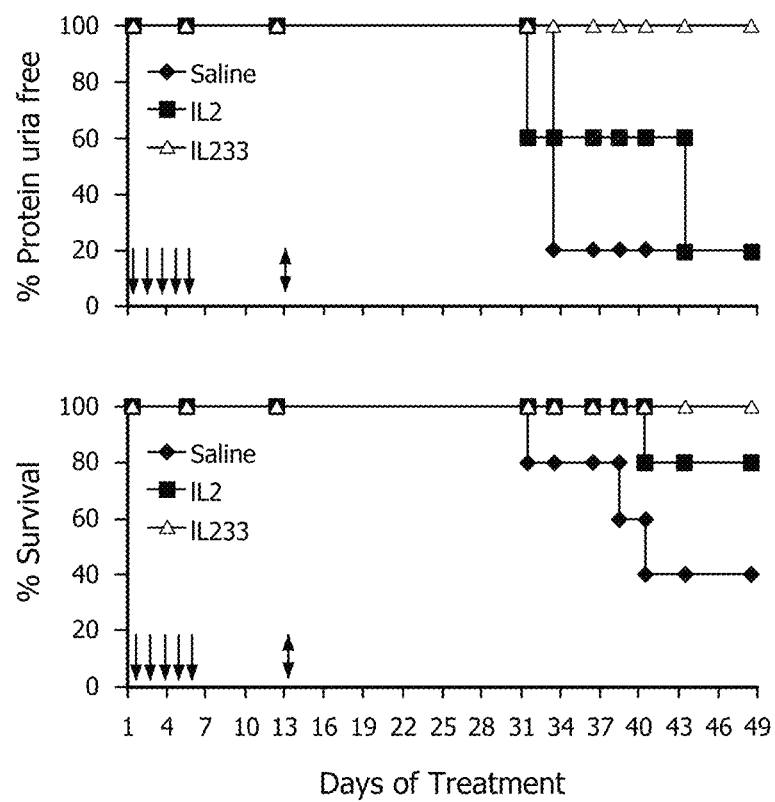
Figures 9A, 9B:
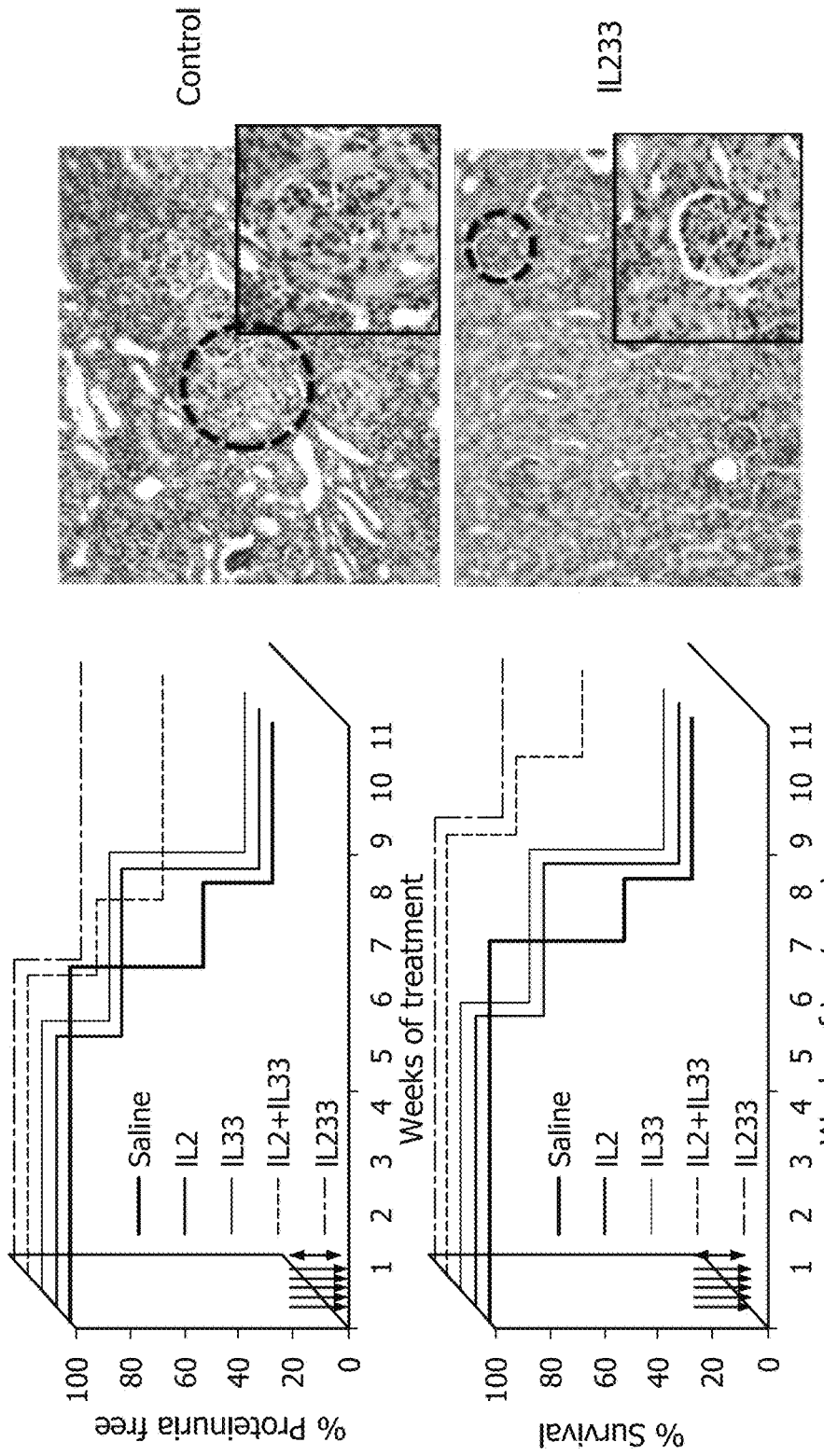
Figures 9C, 9D:
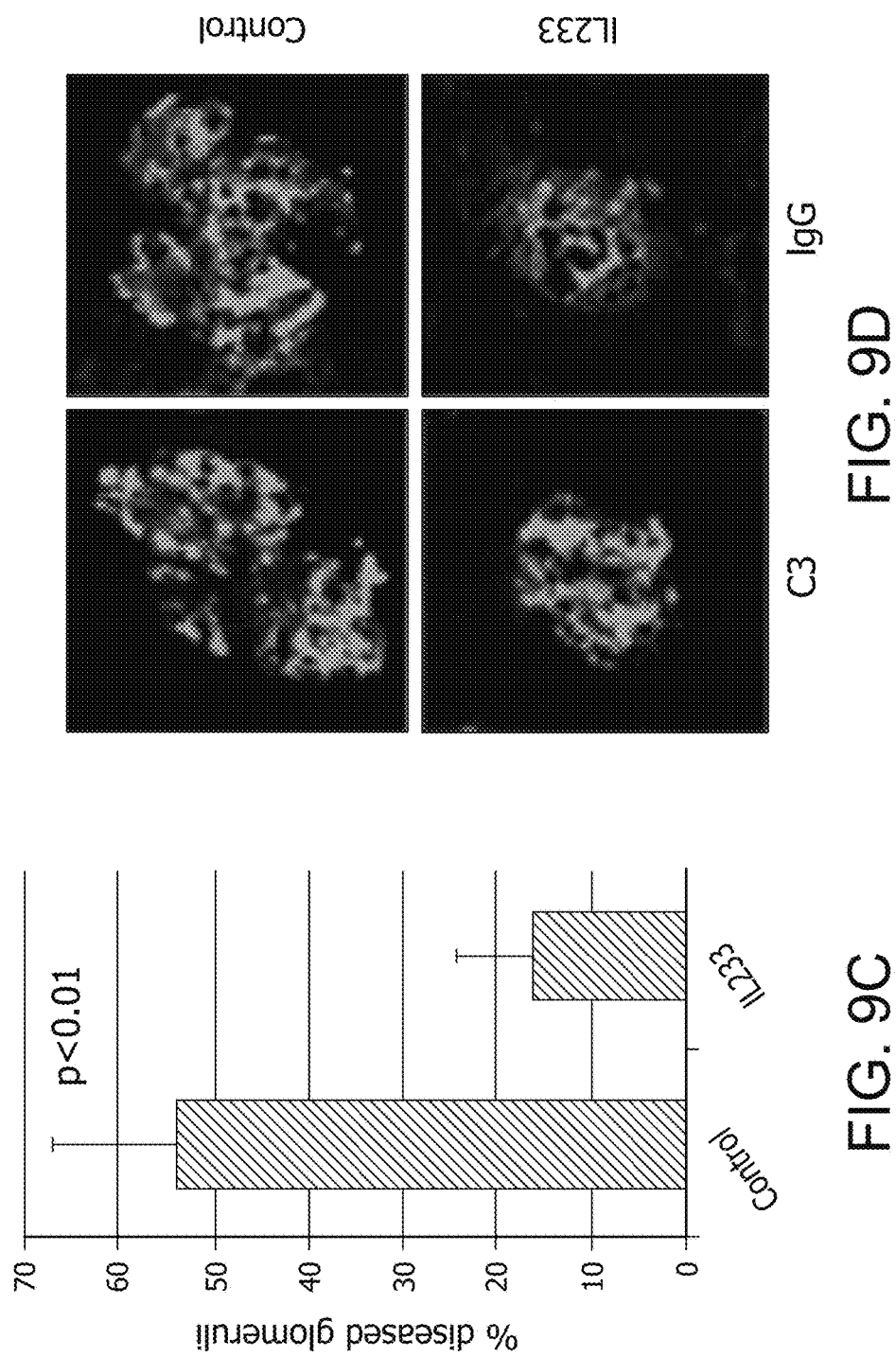
Figure 9E:
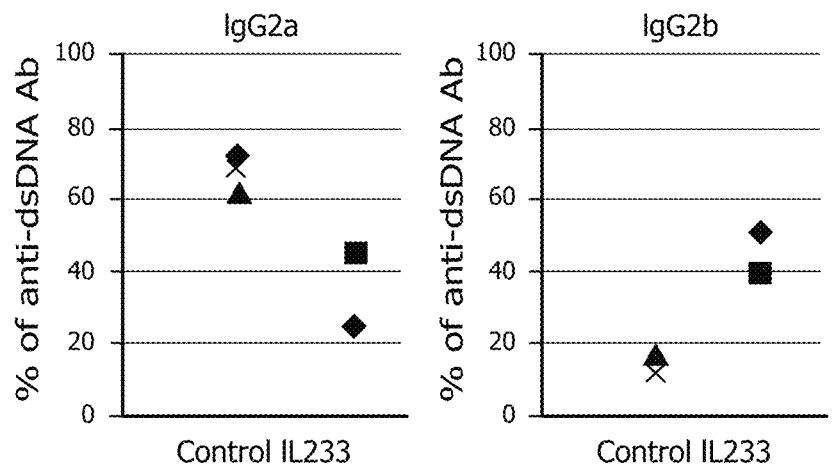
Figure 9F:
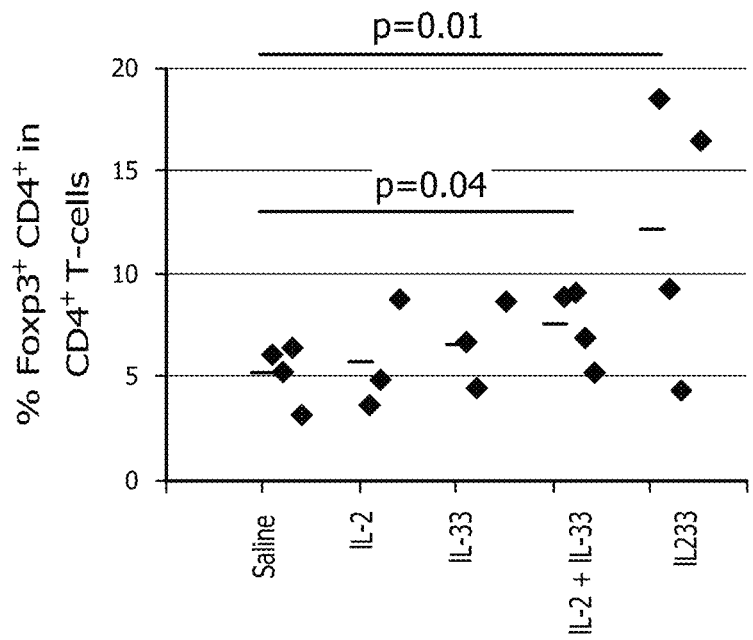
Figure 9G:
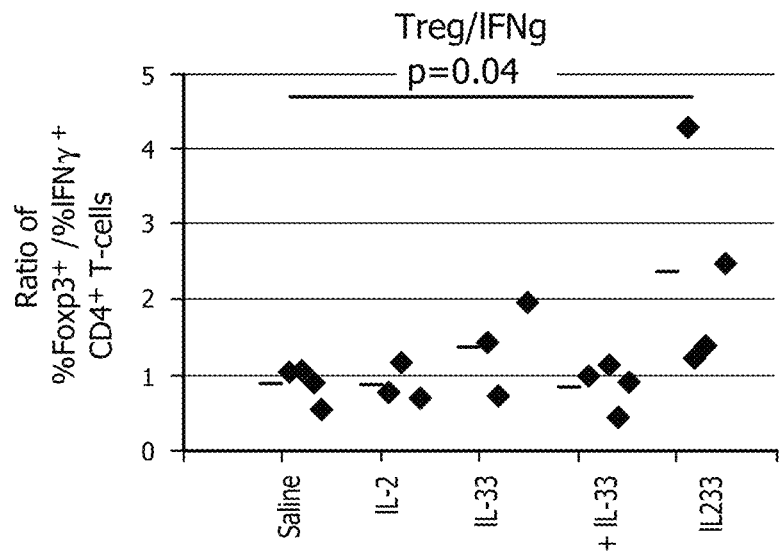
Figure 9H:
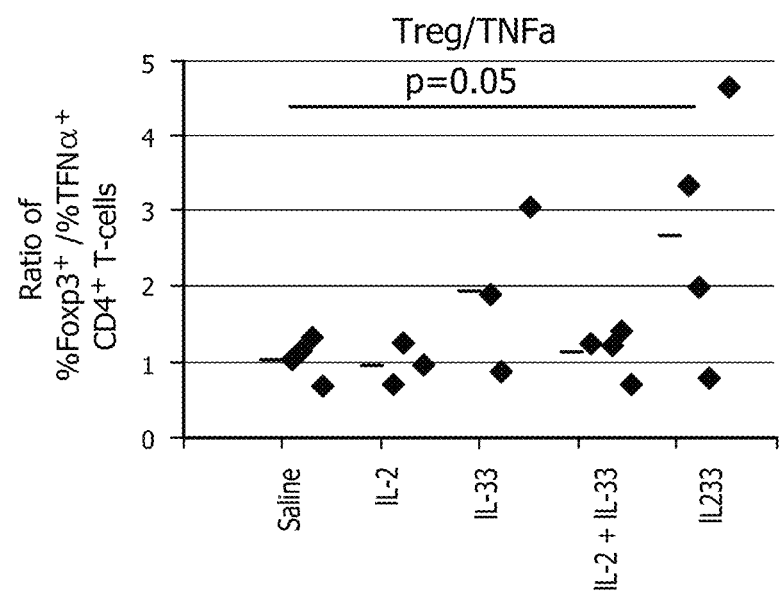
Figure 10A:
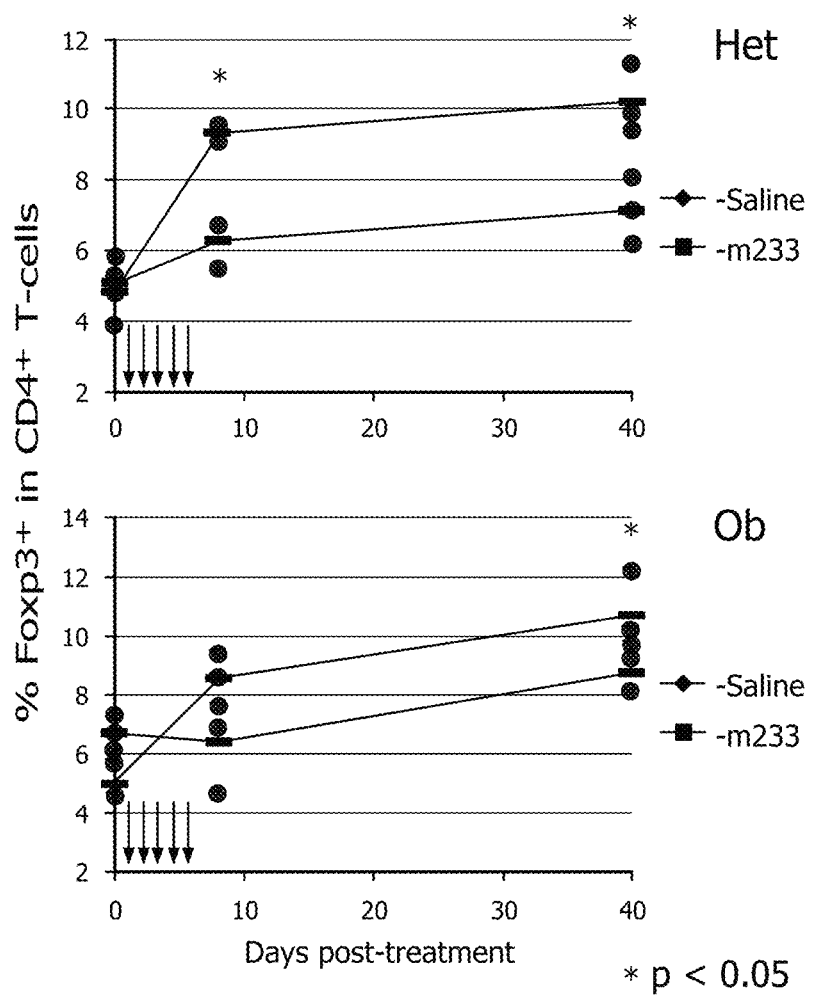
Figure 10B:
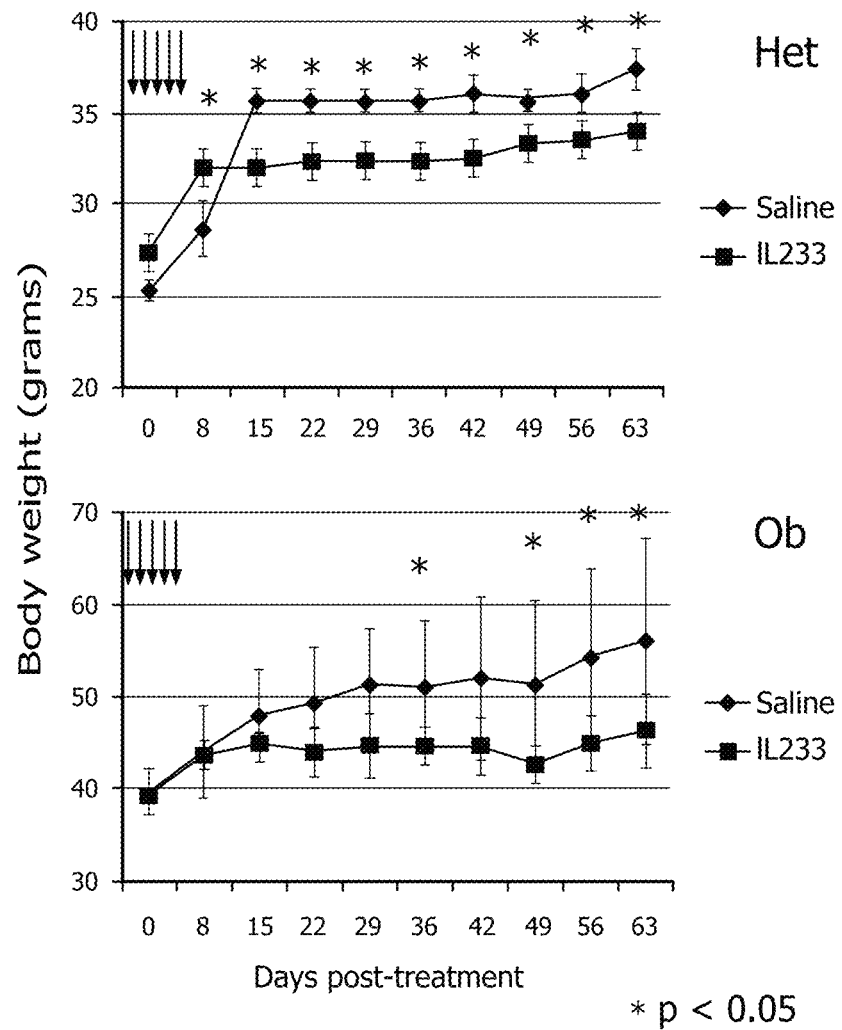
Figure 10C:
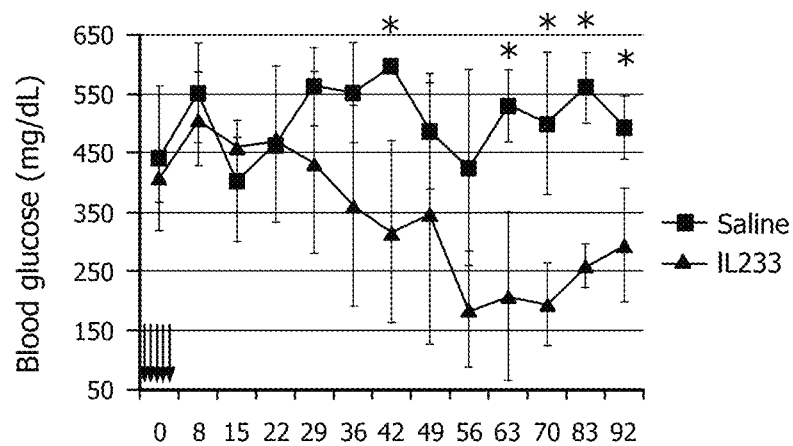
Figure 10D:
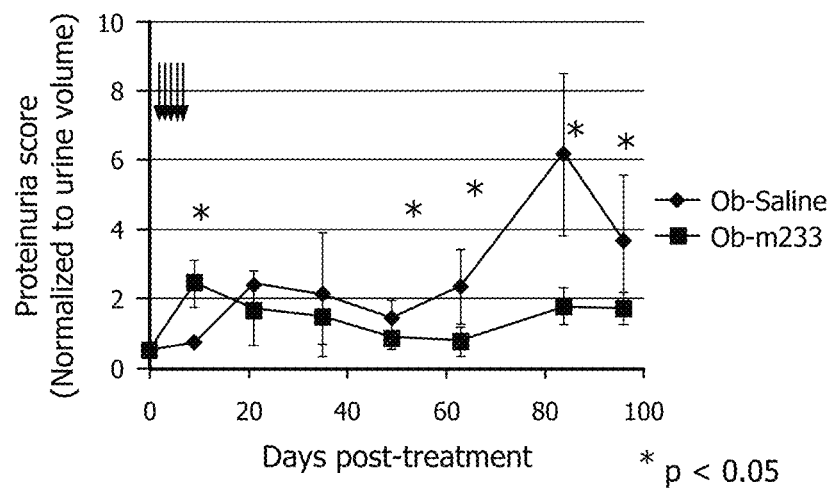
Figure 10E:
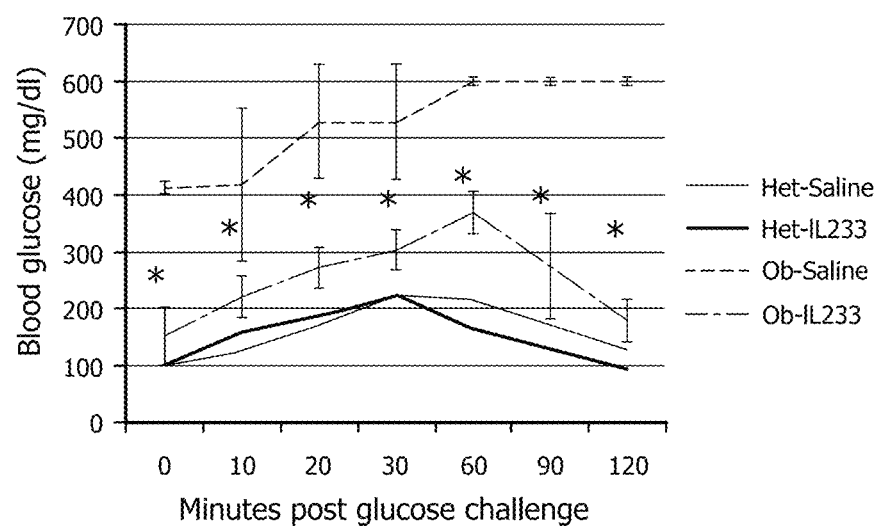
Figure 12A:
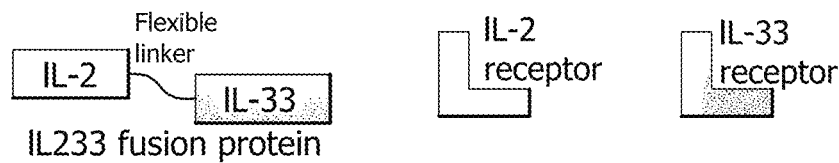
Figure 12B:
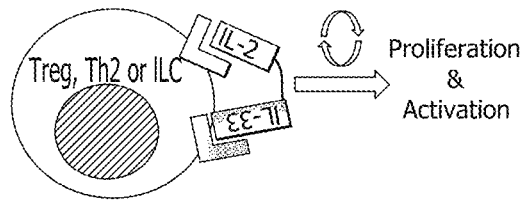
Figure 12C:
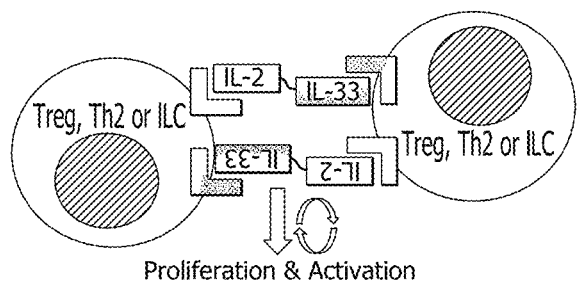
Figure 12D:
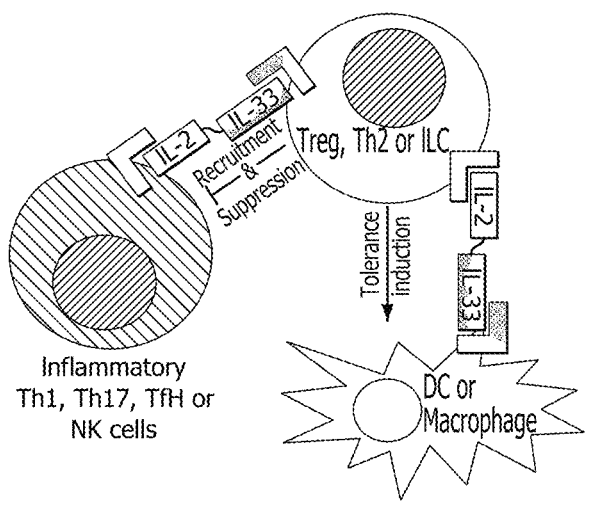

FIG. 8. Treatment with IL233 protects lupus prone NZM2328 mice from lupus glomerulonephritis (GN). Three-month-old NZM2328 female mice (5 mice per group) were injected with recombinant IL-2 or IL233 fusion protein (1 µg IL-2 equivalent of each) daily for 5 days (green arrows). The control mice received saline only. On day 12 all the mice with injected with Ad-IFNα (adenovirus expressing IFNα) to accelerate the lupus nephritis (red double-headed arrow). The mice were monitored periodically for kidney function (proteinuria with dip stick) and mortality. (A) The peripheral blood of mice was analyzed on d1 and d9 of the recombinant cytokine treatment. Treatment with both IL-2 and IL233 resulted in an increase in the Treg levels, as measured by flow cytometry. Treatment with IL233, but not IL-2 resulted in a decrease in the production of TNF-α (a pro-inflammatory cytokine known to contribute to lupus GN) as measured by intracellular staining of lymphocytes for TNF-α after a 5-hour ex-vivo stimulation with Phorbol myristate acetate and Ionomycin. Individual mice are shown. (B) Proteinuria was measure by dipstick and mice with a "+++" score on the dipstick were considered to have severe proteinuria (top). The data is presented as "percent proteinuria free". The control mice (Blue) developed severe proteinuria rapidly, while treatment with IL-2 (red) protected partially. The mice treated with IL233 (green) were completely protected against severe proteinuria at the termination of the experiment. IL233 treatment offered complete protection against mortality, which IL-2 treatment protected partially (bottom). Please note that the molecular mass of IL233 is greater than that of IL-2 or IL-33 and is approximately the sum of the molecular mass of IL-2 and IL-33. Therefore for equimolar comparisons two-fold higher quantity of IL233 is used, e.g. for each 1 µg of IL-2 and/or IL-33, 2 µg of IL233 is used.

FIG. 9. Treatment with IL233 as well as the IL-2 and IL-33 combination is more effective than either cytokine alone to protect lupus prone NZM2328 mice from GN. In another similar experiment, 3-month old NZM2328 mice were injected for five consecutive days (green arrow) with 1 μg equivalent daily of IL-2 or IL-33 or a mixture of IL-2 and IL-33 or IL233. Three days later mice were injected with Adenovirus expressing IFNα to accelerate lupus GN. A) Combined treatment with IL-2 and IL-33, especially as a IL233 cytokine protected NZM2328 mice from severe proteinuria (top) and mortality (bottom) in IFNα-induced accelerated GN (green arrows-cytokine treatment; red arrows IFNα; n=5). B) Representative H & E stained kidney sections show enlarged glomeruli (highlighted by black-dotted circle; higher magnification in the inset), mesangial expansion, glomerulosclerosis (inset) and leukocytic infiltration in the control mice, but not in the IL233-treatment group (quantified in C). D) IL233 treatment, although inhibited glomerular hypertrophy, did not significantly alter Complement C3 and total IgG immune complex deposition. E) IL233 treatment skewed the circulating anti-dsDNA antibodies from IgG2a to IgG2b, p<0.01; n=3. IL233 treatment increased Foxp3$^+$ Tregs as measured in the lymph node (LN) of mice (F) leading to lower ratios of Tregs to IFNγ$^+$ (G) & TNFα$^+$ (H) CD4 T-cells when analyzed 12-wks post initial treatment or when the control of IL-2 or IL-33 treated mice were moribund. Please note that the molecular mass of IL233 is greater than that of IL-2 or IL-33 and is approximately the sum of the molecular mass of IL-2 and IL-33. Therefore for equimolar comparisons two-fold higher quantity of IL233 is used, e.g. for each 1 μg of IL-2 and/or IL-33, 2 μg of IL233 is used. "▲"=individual mice; bar=mean.

FIG. 10. Treatment with IL233 inhibits progression of obesity, type-2 diabetes (T2D; also referred to as diabetes mellitus type 2), and diabetic nephropathy in mice genetically predisposed for obesity. Five to six weeks old BTBR.ob/ob (Ob-obese mice, due to mutation in Leptin gene) or BTBR.ob/+(Het, non-obese mice) were treated once with 5-daily doses of 50 μg/kg of IL233 or saline (green arrows). The mice were monitored for CD4$^+$Foxp3$^+$ Tregs (A), body weight (B), blood glucose (C), proteinuria (D). The glucose tolerance of the mice treated with IL233 also improved to near non-obese levels (E). As shown below, IL233 treatment increased the Treg levels and inhibited the weight gain, hyperglycemia, and proteinuria, and restored glucose tolerance.

FIG. 11. The nucleotide sequence (SEQ ID NO:1) of the synthetic gene (A) and the amino acid sequence (SEQ ID NO:2) (B) of the human recombinant IL233 fusion protein are depicted. The Blue color denotes the IL-2 coding sequence, the red color is the IL-33 encoding sequence, the black residues are the linker segments to provide flexibility to the fusion protein and the yellow highlighted part codes for the TEV protease cleave site. The major restriction sites are underlined in A. (C) mouse IL233 fusion gene nucleic acid sequence (SEQ ID NO:10). (D) mouse IL233 fusion protein sequence (SEQ ID NO:11).

FIG. 12. Schematic illustration of the different modes of action of the IL233 fusion protein. (A) Schematic representation of the IL233 fusion protein and its receptors. IL233 may bind to two receptors on the same cell (B) or on adjacent cells bearing the receptors for IL-2 and IL-33 (C). In a multimeric complex of cells, IL233 binding to Tregs, Th2, or ILC2 on one end and to antigen presenting cell (DC or macrophages) on the other end may induce tolerance, thus suppressing Th1, TH17, or TfH activation. The fusion protein can also induce recruitment of Treg, Th2 or ILC cells to the sites of inflammation to either suppress the pro-inflammatory Th1, Th17 or NK cells (D, left) or induce tolerance by imparting a Th2 skewing or altered maturation phenotype on the antigen presenting DC/macrophages (D, right).

Figure 13:
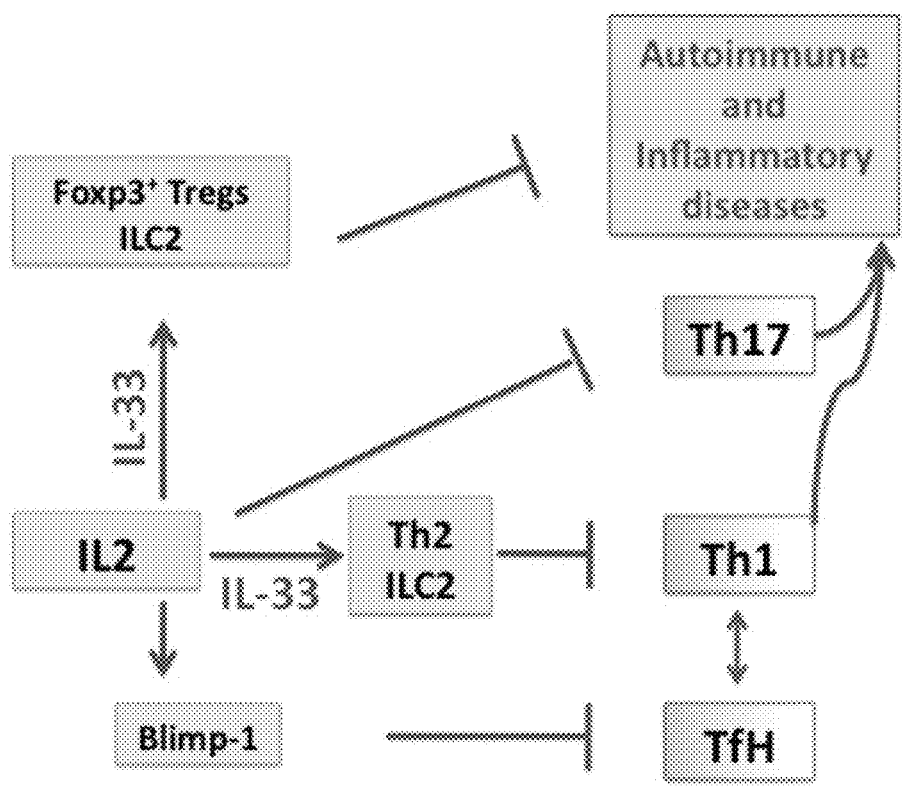

FIG. 13. Schematic illustration of a proposed model of using combinations of IL-2 and IL-33 or a fusion protein of IL-2 and IL-33. Without wishing to be bound by any particular theory, it was hypothesized herein that, owing to the expression of the receptors for IL-2 and IL-33 on the Tregs, Th2 cells and Innate Lymphoid cells type 2 (ILC2), combining the activities of IL-2 and IL-33 could invoke multiple mechanisms for suppression of autoimmune and inflammatory diseases, which include (a) activation and recruitment of Tregs/ILC2 for peripheral tolerance (b) skewing of the immune response towards Th2 for suppression of the pro-inflammatory Th1 and Th17 cells (c) inhibiting the T-follicular helper (TfH) cells, which induce high-affinity autoantibodies and (d) induce tolerogenic alternately activated macrophages. Owing to the high-level constitutive expression of the receptors for both IL-2 and IL-33, a treatment with combination of IL-2 and IL-33 will increase the targeting of Tregs, Th2 and ILC2.

DETAILED DESCRIPTION

Abbreviations and Acronyms

AAM—alternately activated macrophages
AGE—advanced glycation end-product
AIP—autoimmune pancreatitis
AM—acute kidney injury
AMDCC—Animal Models of Diabetic Complications Consortium
APC—antigen presenting cell
DM—diabetes mellitus (can be type 1 or 2)
DN—diabetic nephropathy
ESRD—end-stage renal disease
FALC—fat-associated lymphoid cell
GN—glomerulonephritis
GVHD—graft versus host disease
hIL233—the human fusion peptide of IL-2 and IL-33 (SEQ ID NO:2)
IL1RL1—IL-33 receptor (also known as ST2)
IL233—a fusion peptide of IL-2 and IL-33
IL-2/IL-33—a fusion peptide comprising active fragments of IL-2 and IL-33
IL-33—interleukin 33
ILC—innate lymphoid cells, also referred to as nuocytes
IL-2—interleukin 2
IRI—ischemic reperfusion injury
iTr—induced Treg
g/kg body wt.—grams per kilogram body weight
LB—Luria Bertani
lag/kg body wt.—micrograms per kilogram body weight
M1 macrophage—Th1 associated pro-inflammatory macrophage
M2 macrophage—Th2 associated anti-inflammatory macrophage
m2—murine IL-2 protein
m33—murine IL-33 protein
m233—murine IL233 fusion cytokine, also referred to as mIL233 mIL233—murine fusion protein of murine IL-2 and IL-33 (SEQ ID NO:11)
    MS—multiple sclerosis
    NLS—nuclear localization signal
    NOD—non-obese diabetic
    nTr—natural Treg
    r—recombinant
    RLN—renal lymph node
    RSD—related systemic disease
    T1D—type 1 diabetes mellitus
    T2D—type 2 diabetes mellitus
    TAC—transverse aortic constriction
    Tfh—T-follicular helper cell
    Th—T helper cell
    Th1—Thelper1 cell
    Th2—Thelper2 cell
    Th17—Thelper17 cell
    Tn—naive T cell
    Treg—T regulatory
    UAER—urinary albumin excretion rate Definitions In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As use herein, the terms "administration of" and or "administering" a compound should be understood to mean providing a compound of the invention or a prodrug of a compound of the invention to a subject in need of treatment.

The term "adult" as used herein, is meant to refer to any non-embryonic or non-juvenile subject. For example the term "adult adipose tissue stem cell," refers to an adipose stem cell, other than that obtained from an embryo or juvenile subject.

Cells or tissue are "affected" by an injury, disease or disorder if the cells or tissue have an altered phenotype relative to the same cells or tissue in a subject not afflicted with the injury, disease, condition, or disorder.

As used herein, an "agonist" is a composition of matter that, when administered to a mammal such as a human, enhances or extends a biological activity of interest. Such effect may be direct or indirect.

A disease, condition, or disorder is "alleviated" if the severity of a symptom of the disease or disorder, the frequency with which such a symptom is experienced by a patient, or both, are reduced.

As used herein, "alleviating an injury, disease or disorder symptom," means reducing the frequency or severity of the symptom.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity.

Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

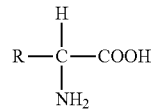

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

An "antagonist" is a composition of matter that when administered to a mammal such as a human, inhibits or impedes a biological activity attributable to the level or presence of an endogenous compound in the mammal Such effect may be direct or indirect.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

The term "associated with ischemia" as used herein means that an injury, disease, or disorder that is being treated or which is being prevented either develops as a result of ischemia or ischemia develops as a result of the injury disease or disorder, i.e., the two are closely linked.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a living organism, including skin, hair, tissue, blood, plasma, cells, sweat, and urine.

As used herein, the term "biologically active fragments" or "bioactive fragment" of the polypeptides encompasses natural or synthetic portions of the full-length protein that are capable of specific binding to their natural ligand or of performing the function of the protein.

A "biomarker" is a specific biochemical in the body which has a particular molecular feature that makes it useful for measuring the progress of disease or the effects of treatment, or for measuring a process of interest.

As used herein, the term "carrier molecule" refers to any molecule that is chemically conjugated to the antigen of interest that enables an immune response resulting in antibodies specific to the native antigen.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. As used herein, the terms "complementary" or "complementarity" are used in reference to polynucleotides (i.e., a sequence of nucleotides) related by the base-pairing rules. For example, for the sequence "A-G-T," is complementary to the sequence "T-C-A."

Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "complex", as used herein in reference to proteins, refers to binding or interaction of two or more proteins. Complex formation or interaction can include such things as binding, changes in tertiary structure, and modification of one protein by another, such as phosphorylation.

A "compound," as used herein, refers to any type of substance or agent that is commonly considered a drug, or a candidate for use as a drug, as well as combinations and mixtures of the above.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, chemokines, protein or peptide hormones, and transforming growth factors. A number of other cytokines are known to those of skill in the art. The sources, characteristics, targets and effector activities of these cytokines have been described.

The term "delivery vehicle" refers to any kind of device or material which can be used to deliver compounds in vivo or can be added to a composition comprising compounds administered to a plant or animal. This includes, but is not limited to, implantable devices, aggregates of cells, matrix materials, gels, nucleic acids, etc. As used herein, a "derivative" of a compound, when referring to a chemical compound, is one that may be produced from another compound of similar structure in one or more steps, as in replacement of H by an alkyl, acyl, or amino group.

A "derivative protein or peptide," as used herein, includes any protein or peptide, which in its entirety, or in part, comprises a substantially similar amino acid sequence to an IL-2 and IL-33 fusion peptide (IL233) and has IL233 biological activity as disclosed herein. Derivatives of IL233 may be characterized by single or multiple amino acid substitutions, deletions, additions, or replacements. These derivatives may include (a) derivatives in which one or more amino acid residues are substituted with conservative or non-conservative amino acids; (b) derivatives in which one or more amino acids are added to one or more of the components of the fusion peptide (c) derivatives in which one or more of the amino acids includes a substituent group; (d) derivatives in which one of the constituent groups or a portion thereof is fused to another peptide (e.g., serum albumin or protein transduction domain); (e) derivatives in which one or more nonstandard amino acid residues (i.e., those other than the 20 standard L-amino acids found in naturally occurring proteins) are incorporated or substituted into one of the IL-2 or IL-33 substituents; and (f) derivatives in which one or more nonamino acid linking groups are incorporated into or replace a portion of one of the portions of the fusion protein. A derivative protein may also be referred to as homologous when used in the context described herein. A derivative or homolog as described or claimed herein will have similar activity to IL-2, IL-33, and the fusion peptide IL233 as disclosed herein.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, the term "diagnosis" refers to detecting a disease or disorder or a risk or propensity for development of a disease or disorder, for the types of diseases or disorders encompassed by the invention. In any method of diagnosis there exist false positives and false negatives. Any one method of diagnosis does not provide 100% accuracy.

A "disease" is a state of health of an animal wherein the subject cannot maintain homeostasis, and wherein if the disease is not ameliorated then the subject's health continues to deteriorate. In contrast, a "disorder" in a subject is a state of health in which the animal is able to maintain homeostasis, but in which the subject's state of health is less favorable than it would be in the absence of the disorder. Left untreated, a disorder does not necessarily cause a further decrease in the subject's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains. As used herein, the term "effector domain" refers to a domain capable of directly interacting with an effector molecule, chemical, or structure in the cytoplasm which is capable of regulating a biochemical pathway.

The term "downstream" when used in reference to a direction along a nucleotide sequence means the 5' to 3' direction. Similarly, the term "upstream" means the 3' to 5' direction.

As used herein, an "effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "enhancer" is a DNA regulatory element that can increase the efficiency of transcription, regardless of the distance or orientation of the enhancer relative to the start site of transcription.

As used herein, an "essentially pure" preparation of a particular protein or peptide is a preparation wherein at least about 95%, and preferably at least about 99%, by weight, of the protein or peptide in the preparation is the particular protein or peptide.

As used in the specification and the appended claims, the terms "for example," "for instance," "such as," "including"

and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein.

As used herein the term "expression" when used in reference to a gene or protein, without further modification, is intended to encompass transcription of a gene and/or translation of the transcript into a protein.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 2-15 amino acids in length, at least about 15-25 amino acids, at least about 25-50 amino acids in length, at least about 50-75 amino acids in length, at least about 75-100 amino acids in length, and greater than 100 amino acids in length, depending on the particular protein or peptide being referred to.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" molecule is a molecule in a form in which it exhibits a property or activity by which it is characterized. A functional enzyme, for example, is one that exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity." The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, the term "induction of apoptosis" means a process by which a cell is affected in such a way that it begins the process of programmed cell death, which is characterized by the fragmentation of the cell into membrane-bound particles that are subsequently eliminated by the process of phagocytosis.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

The term "injected once with a 5-daily dose", as used herein, means that an induction therapy was initiated wherein mice were injected with 1 µg protein once a day for five consecutive days and then followed over time as indicated.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The term "ischemia" as used herein refers to a local anemia due to mechanical obstruction of the blood supply, which gives rise to inadequate circulation of the blood to an organ, tissue, or region of an organ or tissue.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

The term "material" refers to any compound, molecule, substance, or group or combination thereof that forms any type of structure or group of structures during or after electroprocessing. Materials include natural materials, synthetic materials, or combinations thereof. Naturally occurring organic materials include any substances naturally found in the body of plants or other organisms, regardless of whether those materials have or can be produced or altered synthetically. Synthetic materials include any materials prepared through any method of artificial synthesis, processing, or manufacture. Preferably, the materials are biologically compatible materials.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc., and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

The term "modulate", as used herein, refers to changing the level of an activity, function, or process. The term "modulate" encompasses both inhibiting and stimulating an activity, function, or process.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "Oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Operably linked" refers to a juxtaposition wherein the components are configured so as to perform their usual function. Thus, control sequences or promoters operably linked to a coding sequence are capable of effecting the expression of the coding sequence. By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of a compositions, drug, or compound to a subject.

"Permeation enhancement" and "permeation enhancers" as used herein relate to the process and added materials which bring about an increase in the permeability of skin to a poorly skin permeating pharmacologically active agent, i.e., so as to increase the rate at which the drug permeates through the skin and enters the bloodstream. "Permeation enhancer" is used interchangeably with "penetration enhancer".

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan. As used herein, "pharmaceutical compositions" include formulations for human and veterinary use.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

By "presensitization" is meant pre-administration of at least one innate immune system stimulator prior to challenge with a pathogenic agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "prevent," as used herein, means to stop something from happening, or taking advance measures against something possible or probable from happening. In the context of medicine, "prevention" generally refers to action taken to decrease the chance of getting a disease or condition.

A "prophylactic" treatment is a treatment administered to a subject who does not exhibit signs of a disease or injury or exhibits only early signs of the disease or injury for the purpose of decreasing the risk of developing pathology associated with the disease or injury.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates. The terms "protein pathway" and "protein regulatory pathway" are used interchangeably herein.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

The term "regulate" refers to either stimulating or inhibiting a function or activity of interest.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

As used herein, the term "secondary antibody" refers to an antibody that binds to the constant region of another antibody (the primary antibody).

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds.

The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison.

For example, a standard can be a known standard agent or compound which is administered or added to a control sample and used for comparing results when measuring said compound in a test sample. In one aspect, the standard compound is added or prepared at an amount or concentration that is equivalent to a normal value for that compound in a normal subject. Standard can also refer to an "internal standard," such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

As used herein, a "substantially homologous amino acid sequence" includes those amino acid sequences which have at least about 95% homology, preferably at least about 96% homology, more preferably at least about 97% homology, even more preferably at least about 98% homology, and most preferably at least about 99% homology to an amino acid sequence of a reference sequence Amino acid sequences similarity or identity can be computed using, for example, the BLASTP and TBLASTN programs which employ the BLAST (basic local alignment search tool) algorithm. The default setting used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially similar nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 96%, 97%, 98%, 99% or more. Substantial similarity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M $NaPO_4$, 1 mM EDTA at 50° C. with washing in 2× standard saline citrate (SSC), 0.1% SDS at 50° C.; preferably in 7% (SDS), 0.5 M $NaPO_4$, 1 mM EDTA at 50° C. with washing in 1×SSC, 0.1% SDS at 50° C.; preferably 7% SDS, 0.5 M $NaPO_4$, 1 mM EDTA at 50° C. with washing in 0.5×SSC, 0.1% SDS at 50° C.; and more preferably in 7% SDS, 0.5 M $NaPO_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

"Tissue" means (1) a group of similar cells united to perform a specific function; (2) a part of an organism consisting of an aggregate of cells having a similar structure and function; or (3) a grouping of cells that are similarly characterized by their structure and function, such as muscle or nerve tissue.

The term "transfection" is used interchangeably with the terms "gene transfer", "transformation," and "transduction", and means the intracellular introduction of a polynucleotide. "Transfection efficiency" refers to the relative amount of the transgene taken up by the cells subjected to transfection. In practice, transfection efficiency is estimated by the amount of the reporter gene product expressed following the transfection procedure.

The term "transgene" is used interchangeably with "inserted gene," or "expressed gene" and, where appropriate, "gene". "Transgene" refers to a polynucleotide that, when introduced into a cell, is capable of being transcribed under appropriate conditions so as to confer a beneficial property to the cell such as, for example, expression of a therapeutically useful protein. It is an exogenous nucleic acid sequence comprising a nucleic acid which encodes a promoter/regulatory sequence operably linked to nucleic acid which encodes an amino acid sequence, which exogenous nucleic acid is encoded by a transgenic mammal As used herein, a "transgenic cell" is any cell that comprises a nucleic acid sequence that has been introduced into the cell in a manner that allows expression of a gene encoded by the introduced nucleic acid sequence.

As used herein, the term "transgenic mammal" means a mammal, the germ cells of which comprise an exogenous nucleic acid.

The term to "treat," as used herein, means reducing the frequency with which symptoms are experienced by a patient or subject or administering an agent or compound to reduce the frequency with which symptoms are experienced.

As used herein, the term "treating" may include prophylaxis of the specific injury, disease, disorder, or condition, or alleviation of the symptoms associated with a specific injury, disease, disorder, or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease and should be interpreted based on the context of the use.

"Treating" is used interchangeably with "treatment" herein.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

The present application discloses the unexpected result of synergy between IL-2 and IL-33 as a combination therapy and an even better result/efficacy using a novel IL-2/IL-33 fusion protein. In some aspects, the results can be additive. In some aspects, the results are synergistic.

In one embodiment, the IL233 fusion protein can be used for treatment of inflammatory conditions via boosting the homeostasis and activity of Treg cells, which offer the major mechanism of peripheral immune tolerance.

In another embodiment, the IL233 fusion protein can be used to potentiate the Th2 response by increasing the production of the related cytokines (IL-4, IL-5, and IL-13) by the differentiated Th2 cells, the innate lymphoid cells, Nuocytes, natural helper cells or fat associated lymphoid cluster (FALC).

In yet another embodiment, the invention can be used for skewing of the immune response by inhibiting the pro-inflammatory Th1 response and boosting the anti-inflammatory Th2 immune response.

In a further embodiment, the invention can be used for altering the phenotype of innate immune cells, such as dendritic cells (DC) and macrophages to an altered maturation phenotype, such that these innate immune cells can skew the differentiation of immune response toward a Th2 response, while suppressing the Th1 differentiation. The IL233 treated DC and macrophages can also be employed for boosting the homeostasis of Treg cells.

In one embodiment, the compositions and methods of the invention are useful for regulating the above described mechanisms either individually or in cooperation for prevention or treatment of autoimmune disorders including Type-1 diabetes, Type-2 diabetes, multiple sclerosis, atherosclerosis, systemic lupus erythematosus (lupus), autoimmune pancreatitis, IgG4-related systemic disease spectrum diseases (IgG4-RSD), Sjogren's syndrome, inflammatory bowel disease (Crohn's disease, and ulcerative colitis), autoimmune thyroiditis, autoimmune encephalomyelitis, Alzheimer's disease and dementia, ankylosing spondylitis, chronic obstructive pulmonary disease, myasthenia gravis, obesity, osteoporosis, periodontal disease, psoriasis and uveitis.

In another embodiment, the IL233 fusion protein can be administered to boost immune tolerance during transplantation and to enhancing graft survival via boosting the homeostasis and recruitment of Treg and Th2 cells. In yet another embodiment, the compositions and methods of the invention can be employed for treatment of inflammatory conditions arising due to ischemia reperfusion injury of various organs including, kidneys, lung and heart.

In a further embodiment, the compositions and methods of the invention are useful for treating cardiovascular diseases by not only suppressing inflammation, but also by improving cardiovascular function. Treatment with IL-33 has been demonstrated to have cardio-protective properties in a model of pressure overload and improved survival following transverse aortic constriction in wild-type but not IL-33 receptor mice. IL-33 can also reduce cardiomyocyte apoptosis, decrease infarct and fibrosis, and improve ventricular function in vivo via suppression of caspase-3 activity and increased expression of the 'inhibitor of apoptosis' family of proteins.

In one embodiment, the compositions and methods of the invention are useful for suppressing inflammation in the central nervous system and they are useful for promoting the homeostasis of microglia cells. The methods include treatment of several neurological disorders linked with microglia-cell related defects such as Rhett syndrome.

In one embodiment, the compositions and methods of the invention are useful for reducing inflammation in adipose tissue by altering the phenotype of the adipose tissue resident macrophages to an altered maturation phenotype, which will suppress the Th1 and Th17 induced inflammation associated with obesity and Type-2 diabetes. The fusion protein or combinations of Il-2 and IL-33 will also be useful for suppression of adipogenesis, because IL-33 has been shown to suppress the expression of several genes related to adipogenesis and improve fasting glucose levels as well as resistance to insulin and glucose in mouse model of type-2 diabetes.

One of ordinary skill in the art will appreciate that the sequences of the components of the IL233 fusion protein can be modified independently of one another with conservative amino acid changes, including, insertions, deletions, and substitutions, and that the valency could be altered as well, as long as the resulting multimer/multimeric complex remains effective Amino acid changes (fragments and homologs) can be made independently in each IL-2 and IL-33 as well when they are being used in combination therapy.

In one aspect, a fusion protein construct of the invention or a IL-2 and IL-33 combination can be administered by a route selected from, including, but not limited to, intravenously, intrathecally, locally, intramuscularly, topically, orally, intra-arterially, parenterally, etc. Administration can be more than once. One of ordinary skill in the art can determine how often to administer the compound, the dose to be used, and what combination of other agents it can be administered with such as therapeutic agents and/or other drugs or compounds such as antimicrobial agents, anti-inflammatory agents, etc. One of ordinary skill in the art can also determine if all compounds should be administered simultaneously or not.

In one embodiment, a peptide construct dosage or protein dosage of about 0.1 µg/kg body weight to about 100 mg/kg can be administered to a subject in need thereof, including whole numbers between 0.1 and 100 and fractions thereof. In one aspect, a peptide construct dosage or protein dosage of about 0.1 µg/kg to about 75 µg/kg can be administered to a subject. In another aspect, a dosage of about 5.0 µg/kg to about 50 µg/kg can be administered to a subject. In yet another aspect, a dosage of about 10 µg/kg to about 25 µg/kg can be administered to a subject. In a further aspect, a dosage of about 15 µg/kg to about 20 µg/kg can be administered to a subject. In one aspect, a dose of about 1 µg/kg body weight to about 1000 µg/kg body weight, or about, 10 µg/kg body weight to about 500 µg/kg body weight, about 20 µg/kg body weight to about 100 µg/kg body weight, or about 30 µg/kg body weight to about 50 µg/kg body weight. In one aspect, doses that can be used include 5.0, 15, 50, and 150 µg/kg of body weight.

Numerical ranges recited herein by endpoints include all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about."

In one embodiment, a unit dose of fusion protein construct or proteins can be administered. Other therapeutic agents of the invention can also be administered as unit doses. Kits can be provided with unit doses in a container or syringe or amounts that one of ordinary skill in the art can administer based on a dose per weight, etc.

In one embodiment, a fusion protein construct or proteins of the invention are administered at least once a day, or at least once a week, or at least once a month. In one embodiment, a fusion peptide construct or proteins of the invention are administered at least twice a day, at least twice a week, or at least twice a month. In one aspect, doses are administered in a series of five doses over five days. One of ordinary skill in the art can determine how much to administer and how often to administer it.

The invention further includes isolated nucleic acids comprising sequences encoding proteins or peptides of the invention. The present invention further includes a fusion protein wherein the order of the peptides is reversed. In one aspect, the IL-33 is fused to the N-terminus of IL-2 with or without a linker sequence. In another aspect, the IL-2 is fused to the N-terminus of IL-33 with or without a linker sequence. One of ordinary skill in the art will appreciate that the linker length and sequence can be modified and that methods are provided for easily test the resulting activity of the fusion peptide.

Also included are peptides and polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the invention are not limited to products of any of the specific exemplary processes listed herein.

The invention includes the use of beta-alanine (also referred to as β-alanine, β-Ala, bA, and βA, having the structure:

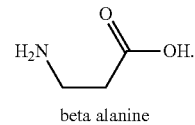

beta alanine

Sequences are provided herein which use the symbol "βA", but in the Sequence Listing submitted herewith "βA" is provided as "Xaa" and reference in the text of the Sequence Listing indicates that Xaa is beta alanine.

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxycarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group.

Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Amino Acid Substitutions

In certain embodiments, the disclosed methods and compositions may involve preparing peptides with one or more substituted amino acid residues.

In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art. For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group. For example, the hydropathic index of amino acids may be considered (Kyte & Doolittle, 1982, J. Mol. Biol., 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges)

between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for analogs of proteins. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on peptide function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, Guide to Protein Purification, Harcourt Brace Jovanovich, San Diego).

In another embodiment disclosed herein, peptide longevity is enhanced by the addition of adducts such as sucrose or polyethylene glycol, production of peptide-IgG chimeras, or the peptides can be cyclized via cysteine-cysteine linkages, which is a modification known to enhance the biological activities of a variety of peptides.

In one aspect a polyethylene glycol adduct is (2-aminoethyl)-O'—(N-diglycolyl-2-aminoethyl)-hexaethyleneglycol. In another aspect of the invention, a polyethylene glycol adduct is in the form of GK[(2-aminoethyl)-O'—(N-diglycolyl-2-aminoethyl)-hexaethyleneglycol]GG. The dipeptide GK increases peptide solubility. The dipeptide GG is present as a spacer between the solid support and peptide chain to improve the ease of peptide synthesis.

The present disclosure also contemplates any of the peptides derivatized with functional groups and/or linked to other molecules to facilitate their delivery to specific sites of action, to potentiate their activity, or complexed covalently or non-covalently to other pharmaceuticals, bioactive agents, or other molecules. Such derivatizations must be accomplished so as to not significantly interfere with the properties of the peptides. Carriers and derivatizations must also be designed or chosen so as not to exert toxic or undesirable activities on animals or humans treated with these formulations. Functional groups which may be covalently linked to the peptides may include, but not be limited to, amines, alcohols, or ethers. Functional groups to be covalently linked to the peptides to increase their in vivo half-lives may include, but not be limited to, polyethylene glycols, small carbohydrates such as sucrose, or peptides and proteins. The peptides may also be synthesized by recombinant DNA techniques with expression vectors for use in biological systems, such as bacteria, yeast, insect, or mammalian cells.

Generally, the amount of peptide administered depends upon the degree of immune response that is desired. Those skilled in the art may derive appropriate dosages and schedules of administration to suit the specific circumstances and needs of the patient. Typically, dosages of peptide are between about 0.001 mg/kg and about 100 mg/kg body weight. In some embodiments dosages are between about 0.01 mg/kg and about 60 mg/kg body weight. In other embodiments, dosages are between about 0.05 mg/kg and about 5 mg/kg body weight.

In general, the schedule or timing of administration of a peptide of the invention is according to the accepted practice for the procedure being performed.

When used in vivo, the peptides of the invention are preferably administered as a pharmaceutical composition. The invention thus provides pharmaceutical compositions comprising a peptide, or a pharmaceutically acceptable salt thereof, and a pharmaceutically acceptable carrier. The peptide of the invention may be present in a pharmaceutical composition in an amount from 0.001 to 99.9 wt %, and more preferably from about 0.1 to 99.0 wt %. To achieve good plasma concentrations, a peptide or a combination of peptides, may be administered, for example, by intravenous injection, as a solution comprising 0.1 to 1.0% of the active agent.

The compositions of the present invention may comprise at least one active peptide, one or more acceptable carriers, and optionally other peptides or therapeutic agents.

For in vivo applications, the peptides of the present invention may comprise a pharmaceutically acceptable salt. Suitable acids which are capable of forming such salts with the compounds of the present invention include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, anthranilic acid, cinnamic acid, naphthalene sulfonic acid, sulfanilic acid and the like.

Pharmaceutically acceptable carriers include physiologically tolerable or acceptable diluents, excipients, solvents or adjuvants. The compositions are preferably sterile and nonpyrogenic. Examples of suitable carriers include, but are not limited to, water, normal saline, dextrose, mannitol, lactose or other sugars, lecithin, albumin, sodium glutamate, cysteine hydrochloride, ethanol, polyols (propylene glycol, polyethylene glycol, glycerol, and the like), vegetable oils (such as olive oil), injectable organic esters such as ethyl oleate, ethoxylated isosteraryl alcohols, polyoxyethylene sorbitol and sorbitan esters, microcrystalline cellulose, aluminum methahydroxide, bentonite, kaolin, agar-agar and tragacanth, or mixtures of these substances, and the like.

The pharmaceutical compositions may also contain minor amounts of nontoxic auxiliary pharmaceutical substances or excipients and/or additives, such as wetting agents, emulsifying agents, pH buffering agents, antibacterial and antifungal agents (such as parabens, chlorobutanol, phenol, sorbic acid, and the like). Suitable additives include, but are not limited to, physiologically biocompatible buffers (e.g., tromethamine hydrochloride), additions (e.g., 0.01 to 10 mole percent) of chelants (such as, for example, DTPA or DTPA-bisamide) or calcium chelate complexes (as for example calcium DTPA or CaNaDTPA-bisamide), or, optionally, additions (e.g. 1 to 50 mole percent) of calcium or sodium salts (for example, calcium chloride, calcium ascorbate, calcium gluconate or calcium lactate). If desired, absorption enhancing or delaying agents (such as liposomes, aluminum monostearate, or gelatin) may be used. The compositions can be prepared in conventional forms, either as liquid solutions or suspensions, solid forms suitable for solution or suspension in liquid prior to injection, or as emulsions. Pharmaceutical compositions according to the present invention can be prepared in a manner fully within the skill of the art.

The peptides of the invention, pharmaceutically acceptable salts thereof, or pharmaceutical compositions comprising these compounds may be administered so that the compounds may have a physiological effect. Administration may occur enterally or parenterally; for example orally, rectally, intracisternally, intravaginally, intraperitoneally, locally (e.g., with powders, ointments or drops), or as a buccal or nasal spray or aerosol. Parenteral administration is preferred. Particularly preferred parenteral administration methods include intravascular administration (e.g. intravenous bolus injection, intravenous infusion, intra-arterial bolus injection, intra-arterial infusion and catheter instillation into the vasculature), peri- and intra-target tissue injection (e.g. peri-tumoral and intra-tumoral injection), subcutaneous injection or deposition including subcutaneous infusion (such as by osmotic pumps), intramuscular injection, and direct application to the target area, for example by a catheter or other placement device.

Where the administration of the peptide is by injection or direct application, the injection or direct application may be in a single dose or in multiple doses. Where the administration of the compound is by infusion, the infusion may be a single sustained dose over a prolonged period of time or multiple infusions.

A composition of the invention may comprise additional ingredients. As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The pharmaceutical composition may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the condition or disease being treated, the type and age of the animal, etc.

Typically, dosages of the compound of the invention which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. In one aspect, the dosage of the compound will vary from about 1 mg to about 10 g per kilogram of body weight of the animal. In another aspect, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type of cancer being diagnosed, the type and severity of the condition or disease being treated, the type and age of the animal, etc.

Suitable preparations include injectables, either as liquid solutions or suspensions, however, solid forms suitable for solution in, suspension in, liquid prior to injection, may also be prepared. The preparation may also be emulsified, or the polypeptides encapsulated in liposomes. The active ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants.

The invention also includes a kit comprising the composition of the invention and an instructional material which describes adventitially administering the composition to a cell or a tissue of a subject. In another embodiment, this kit comprises a (preferably sterile) solvent suitable for dissolving or suspending the composition of the invention prior to administering the compound to the subject.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of using the compositions for diagnostic or identification purposes or of alleviation the diseases or disorders in a cell or a tissue of a mammal. The instructional material of the kit of the invention may, for example, be affixed to a container which contains the multimeric peptide of the invention or be shipped together with a container which contains the peptide. Alternatively, the instructional material may be shipped separately from the container with the intention that the instructional material and the compound be used cooperatively by the recipient.

In other embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes or other agents may be used as adjunct therapies.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

The invention further provides a kit comprising one or more peptides or expression vectors of the invention, an applicator, an instructional material for the use thereof.

Other embodiments of the invention will be apparent to those skilled in the art based on the disclosure and embodiments of the invention described herein. It is intended that the specification and examples be considered as exemplary only, with a true scope and spirit of the invention being indicated by the following claims. While some representative experiments have been performed in test animals, similar results are expected in humans. The exact parameters to be used for injections in humans can be easily determined by a person skilled in the art.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

EXAMPLES

1. IL-2 regulates inflammation in the Pancreas of mice independent of Tregs.

Figure 1B:
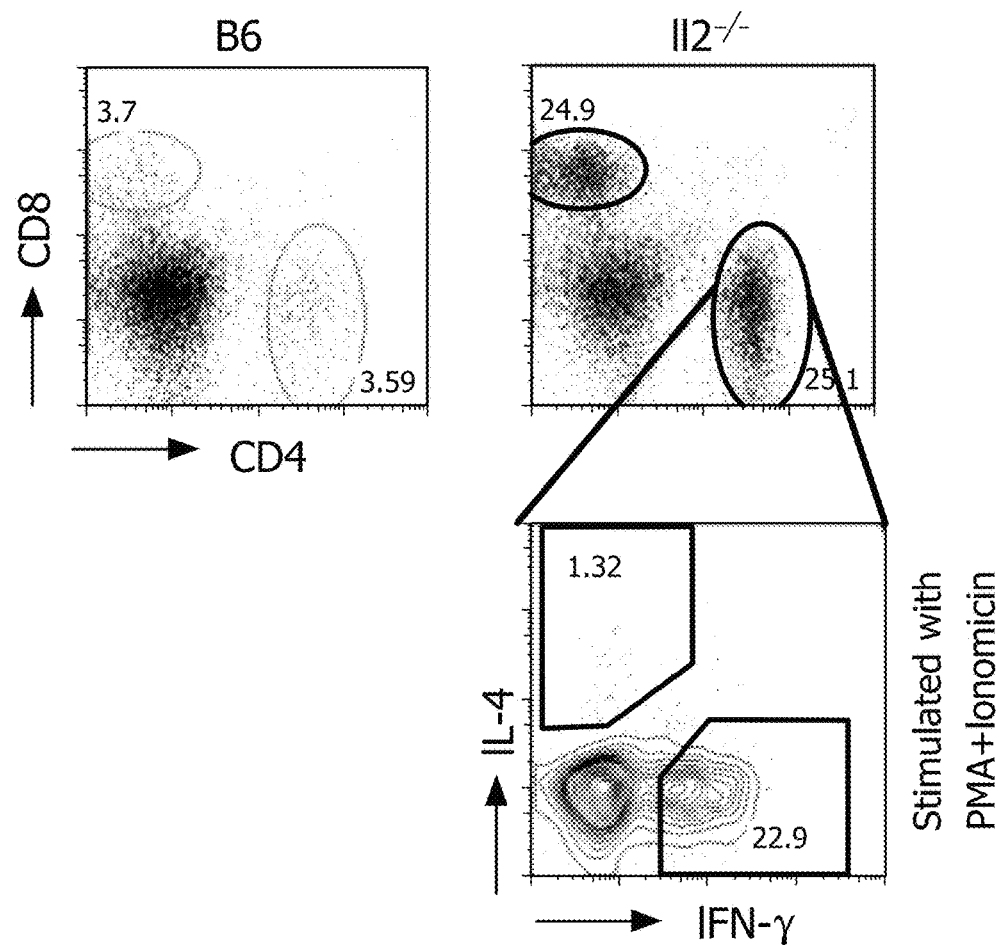
Figure 1C:
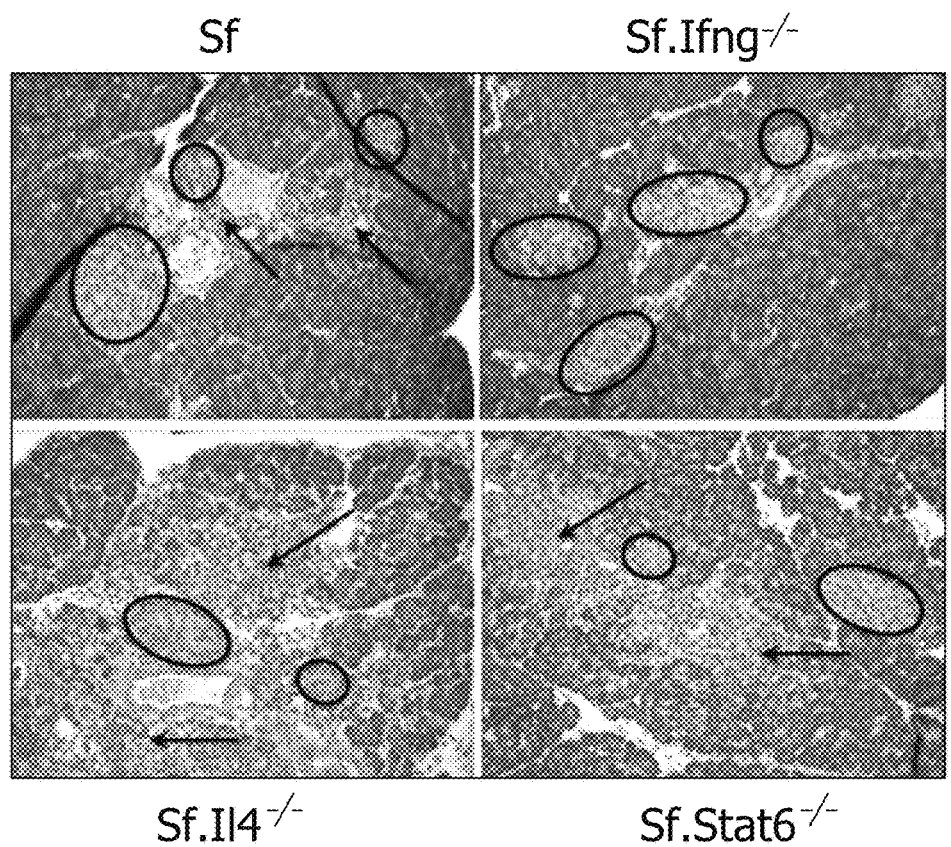

(A) The Foxp3 mutant scurfy (Sf) mice are completely deficient in Treg cells. Yet they are resistant to inflammation in pancreas despite inflammation in several other organs. An additional deficiency of IL-2 in Sf mice (Sf.Il2$^{-/-}$) results in inflammation in pancreas. The IL-2 deficient mice with a partial Treg deficiency (Il2$^{-/-}$) also develop sever inflammation in pancreas. Islets are marked with ellipses and inflammation is shown with arrows. (B) The pancreas infiltrating cells produce mostly IFNγ and little IL-4 as measured by intracellular staining and flow cytometry on ex vivo restimulation with PMA and Ionomicin. (C) Further, deletion of Th2 response genes IL-4 (Sf.Il4$^{-/-}$) or STAT6 (Sf.Stat6$^{-/-}$), also leads to severe pancreatitis in Treg-deficient mice. Deficiency of IFNγ (Sf.Ifng$^{-/-}$) results in protection against such inflammation. Islets are marked with ellipses and inflammation is shown with arrows. (See FIG. 1).

2. IL-2 is a Negative Regulator of T Follicular Helper (TfH) Differentiation.

Figures 2A, 2B:
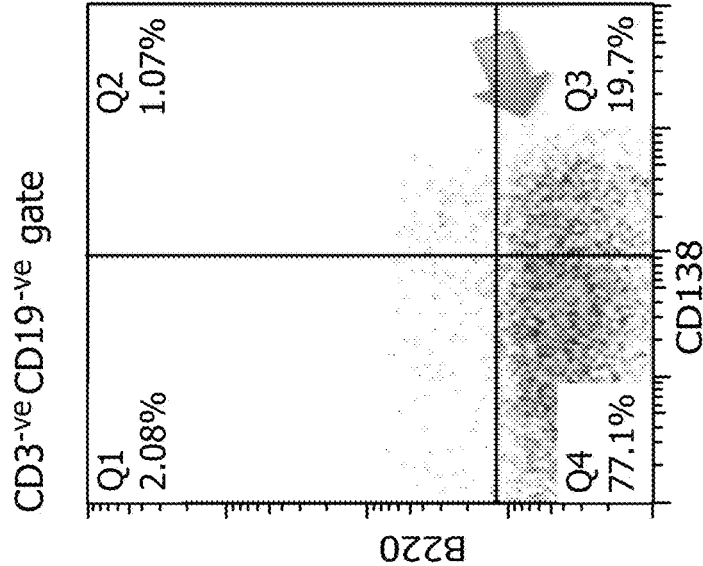
FIG. 2. IL-2 is a negative regulator of T follicular helper (TfH) differentiation. The TfH cells produce IL-21 and promote plasma cell differentiation and production of high affinity autoantibodies. (A) Deficiency of IL-2 induces the expression of genes related to TfH program on CD4$^+$ T cells. (B) This is accompanied with infiltration of plasma cells (arrow) in the pancreas as measured by flow cytometry on the cells isolated from the pancreas.

The TfH cells produce IL-21, promote plasma cell differentiation and production of high affinity autoantibodies. (A) Deficiency of IL-2 induces the expression of genes related to TfH program on CD4$^+$ T cells. (B) This is accompanied with infiltration of plasma cells (arrow) in the pancreas as measured by flow cytometry on the cells isolated form the pancreas. (See FIG. 2).

3. The natural Tregs (nTr) express IL-33 receptor (IL1RL1).

(A). IL1RL1 expression by real-time PCR was measured by real-time PCR on FACS sorted nTr cells. FACS sorted naïve cells (Tn) were differentiated in vitro into induced Tregs (iTr), effector cells (Teff), Th1 or Th2 cells and analyzed for IL1RL1 expression. FACS sorted naïve T-cells (Tn) were used as a control. (B) Expression of IL1RL1 as gated on Tregs and non-Tregs was analyzed by flow cytometry. (See FIG. 3).

4. Treatment with IL233 Increases Natural Tregs (Foxp3$^+$ Helios$^+$) in Mice.

Figure 4:
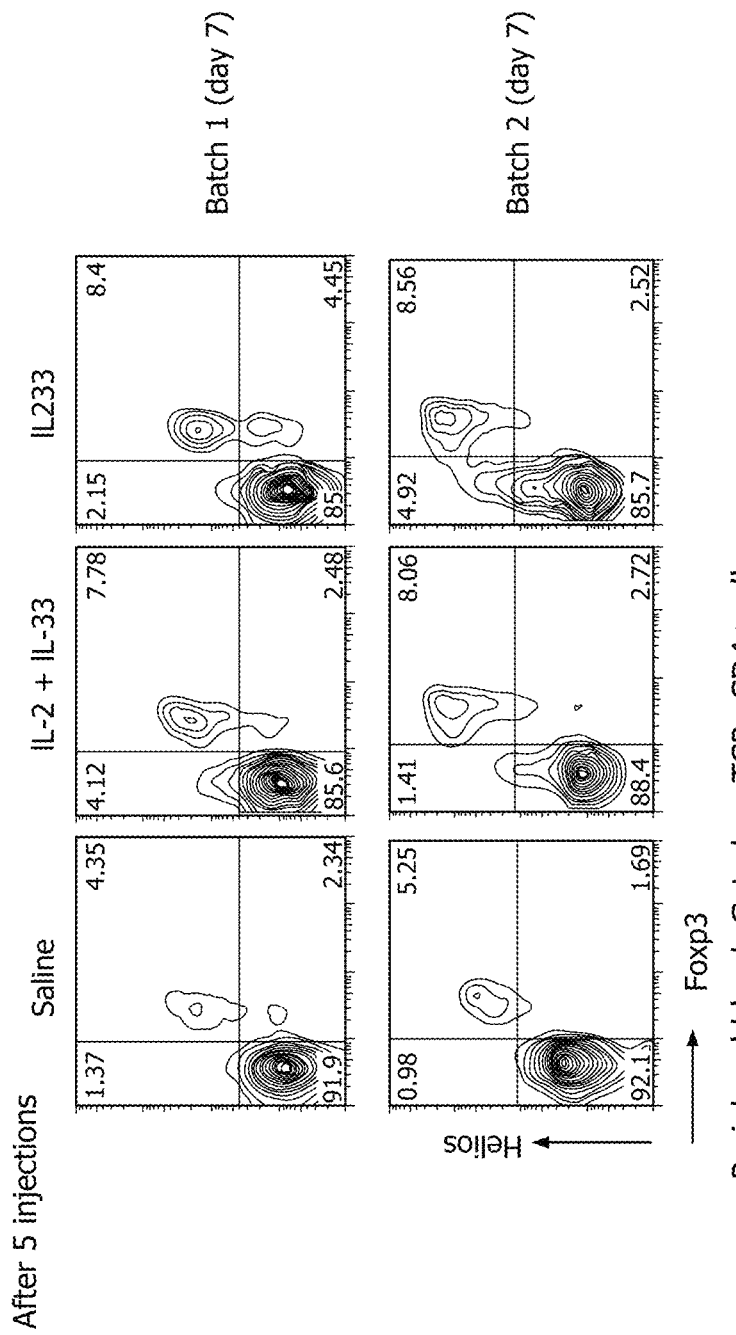
FIG. 4. Treatment with IL233 increases natural Tregs (Foxp3$^+$ Helios$^+$) in mice. Non-obese diabetic (NOD) mice were injected with 5 daily doses of 1 µg equivalent (50 µg/kg of body weight) of a combination of IL-2 and IL-33 or IL233, and CD4$^+$Foxp3$^+$Helios$^+$ cells were evaluated in the peripheral blood by flow cytometry. The control mice were injected with saline. Please note that the molecular mass of IL233 is greater than that of IL-2 or IL-33 and is approximately the sum of the molecular mass of IL-2 and IL-33. Therefore, for equimolar comparisons two-fold higher quantity of IL233 is used, e.g. for each 1 µg of IL-2 and/or IL-33, 2 µg of IL233 is used. Please note that the molecular mass of IL233 is greater than that of IL-2 or IL-33 and is approximately the sum of the molecular mass of IL-2 and IL-33. Therefore for equimolar comparisons two-fold higher quantity of IL233 is used, e.g., for each 1 µg of IL-2 and/or IL-33, 2 µg of IL233 is used.

Non-obese diabetic (NOD) mice were injected with five daily doses of 1.0 µg molar equivalent of a combination of IL-2 and IL-33 or IL233 and CD4$^+$Foxp3$^+$Helios$^+$ cells were evaluated in the peripheral blood by flow cytometry. The control mice were injected with saline. Mice were typically about 20 grams. (See FIG. 4).

5. Treatment of Mice with IL233 Protects Non-Obese Diabetic (NOD) Mice from Type-1 Diabetes Like Disease.

Figure 5A:
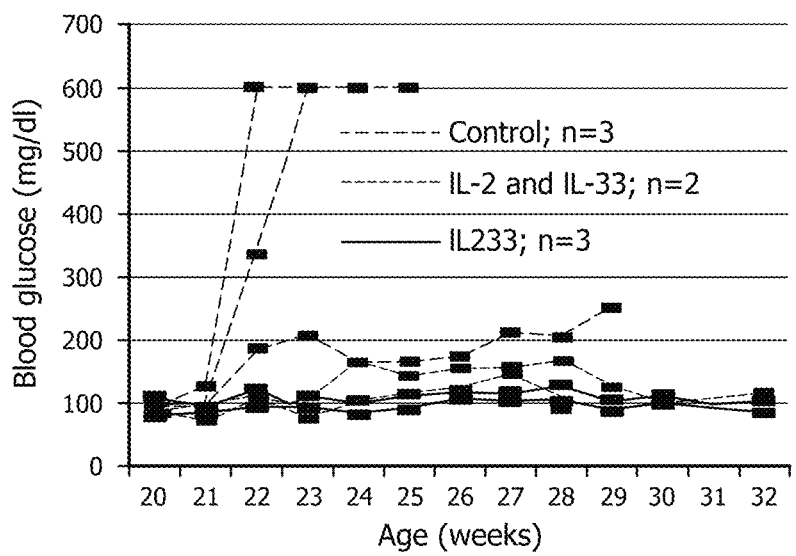
FIG. 5. Treatment of mice with IL233 protects non-obese diabetic (NOD) mice from type-1 diabetes like disease. (A) Female 20 weeks old NOD mice were treated once per day for 5 days with daily i.p. injections of a mixture of 1 µg (~50 µg/kg of body weight) each of IL-2 and IL-33 (orange) or IL233 (green; molar equivalent to 1 µg IL-2) before the onset of hyperglycemia. The treatment with the cytokines protected the mice for long-term against onset of type-1 diabetes like disease as compared to untreated controls (blue). (B) NOD females that were early diabetic (blood glucose 150±10 mg/dl) were treated once for 5 days with daily i.p. injections of 1 µg of recombinant IL-2 (red) or molar equivalent of IL233 (green). Treatment with IL233, but not IL-2 alone protected the mice from ongoing hyperglycemia as shown by the delay in the disease kinetics with ⅔ mice showing complete protection. Blue arrow indicates start of the treatment. (C) In another experiment, NOD mice with early diabetes (blood glucose of 150±10 mg/dL) were treated with one time with 5-daily injections of 0.3 µg/mouse (15 µg/kg of body weight) of IL-2 alone, IL-33 alone, combination of IL-2 and IL-33 or molar equivalent of IL233. The control mice were injected with saline only. The numbers in parenthesis on the right represent the number of mice in each group. Please note that the molecular mass of IL233 is greater than that of IL-2 or IL-33 and is approximately the sum of the molecular mass of IL-2 and IL-33. Therefore for equimolar comparisons two-fold higher quantity of IL233 is used, e.g., for each 1 µg of IL-2 and/or IL-33, 2 µg of IL233 is used.
Figure 5B:
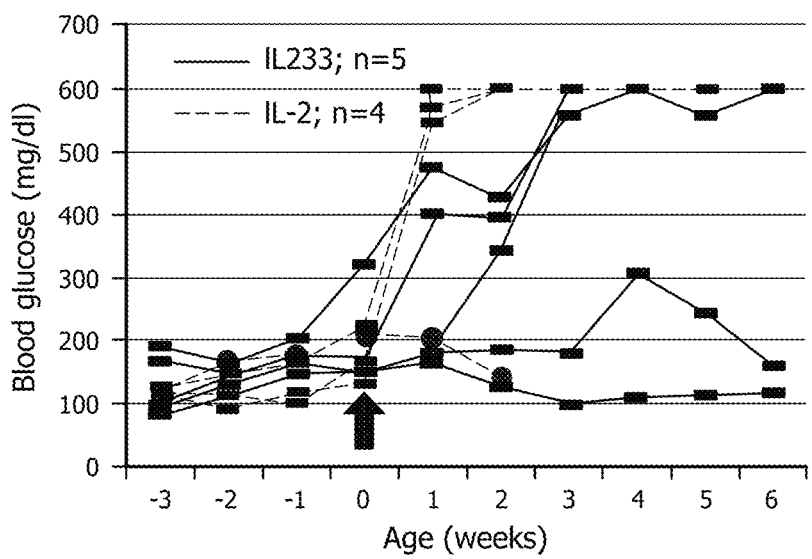
Figure 5C:
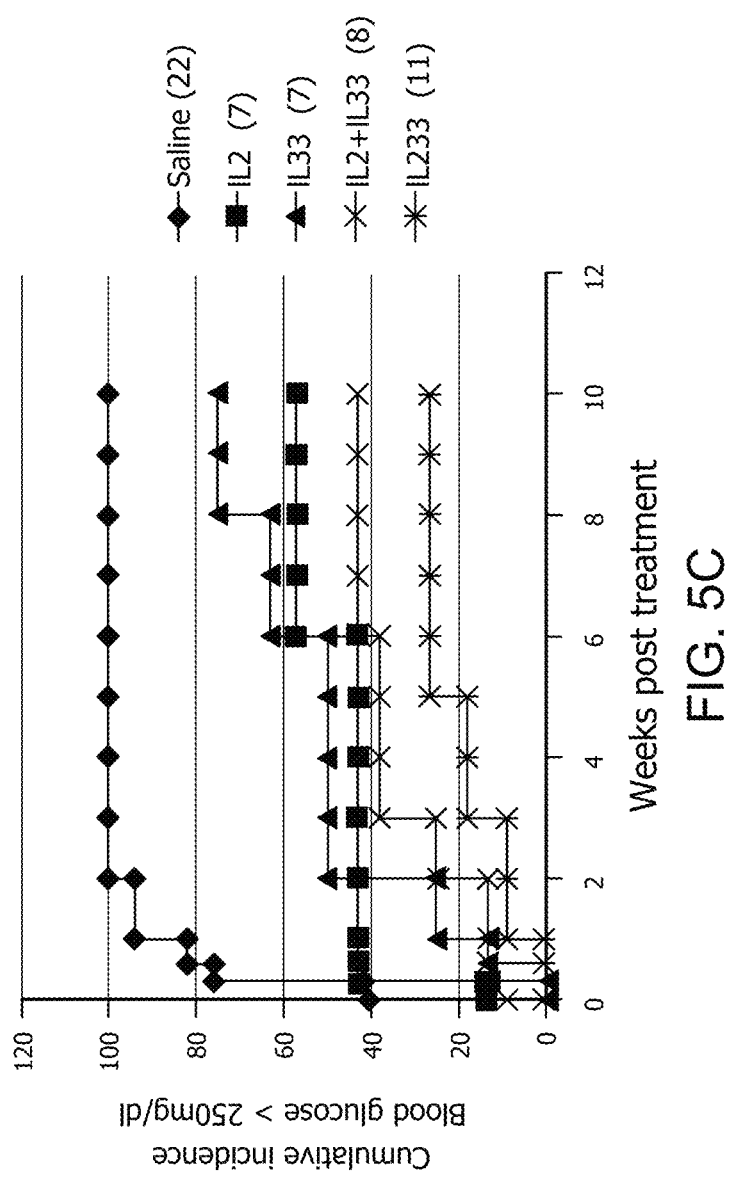

(A) Female 20 week old NOD mice were treated for five days with daily i.p. injections of a mixture of 1.0 µg each of IL-2 and IL-33 (orange) or IL233 (green; molar equivalent to 1.0 µg IL-2) before the onset of hyperglycemia. The treatment with the cytokines protected the mice for long-term against onset of type-1 diabetes like disease as compared to untreated controls (blue). (B) NOD females that were early diabetic were treated for 5 days with daily i.p. injections of 1µg IL-2 molar equivalent of recombinant IL-2 (red) or IL233 (green). Treatment with IL233, but not IL-2 alone, protected the mice from ongoing hyperglycemia as shown by the delay in the disease kinetics with ⅔ mice showing complete protection. Blue arrow indicates start of the treatment. (C) In another experiment mice with early diabetes (blood glucose of 150±10 mg/dL) were treated with one time with 5-daily injections of 0.3 µg/mouse molar equivalent of IL-2 alone, IL-33 alone, a combination of IL-2 and IL-33, or IL233. The control mice were injected with saline only. The numbers in parenthesis on the right represent the number of mice in each group. (See FIG. 5).

6. Treatment with IL233 Expands Treg Cells Especially in the Pancreatic Lymph Nodes.

Figure 6:
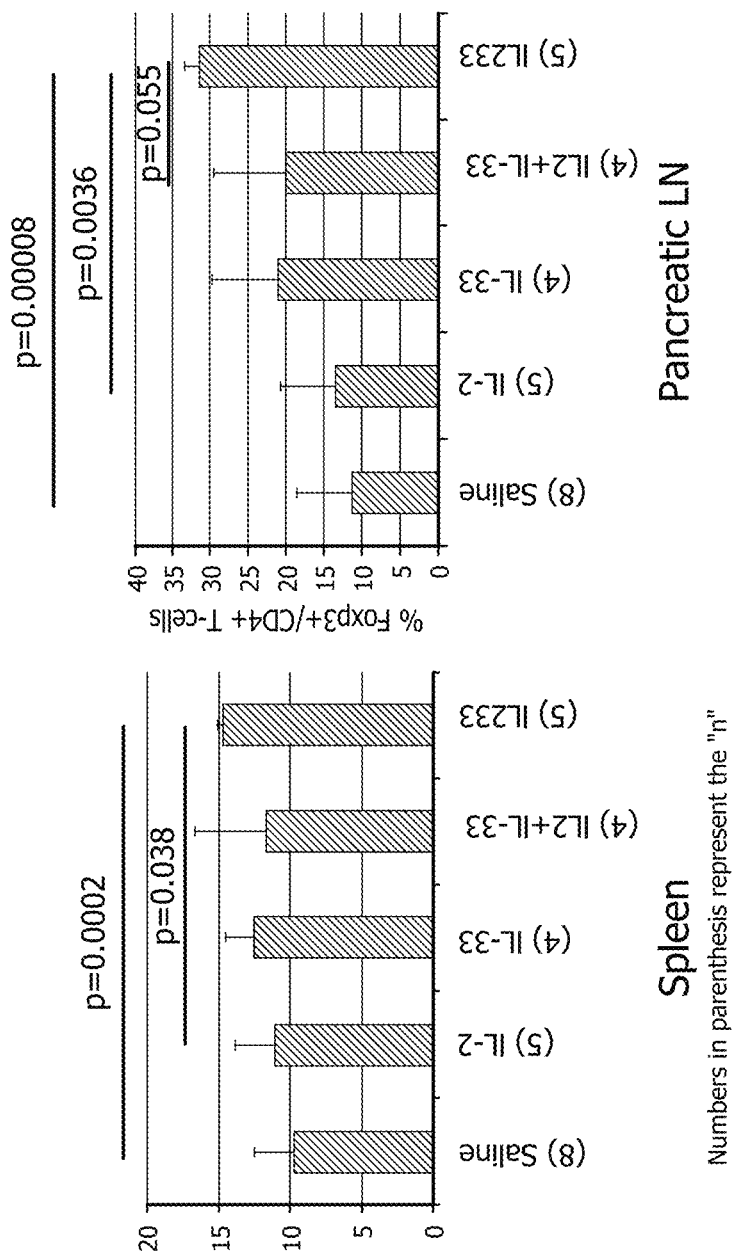
FIG. 6. Treatment with IL233 expands Treg cells especially in the pancreatic Lymph nodes of NOD mice.
Figure 7A:
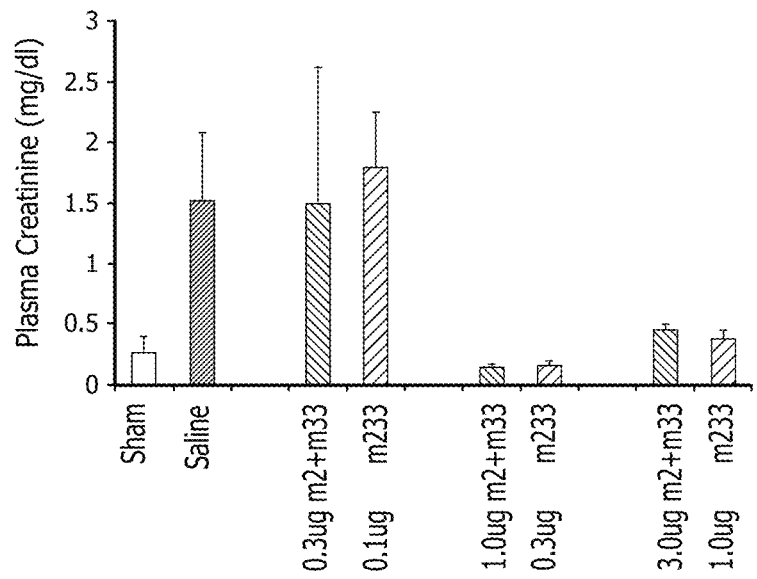
Figure 7B:
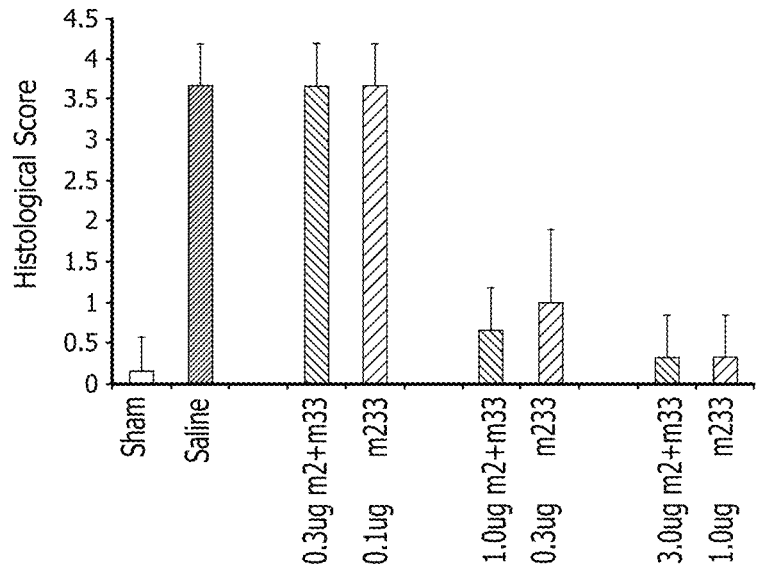
Figure 7C:
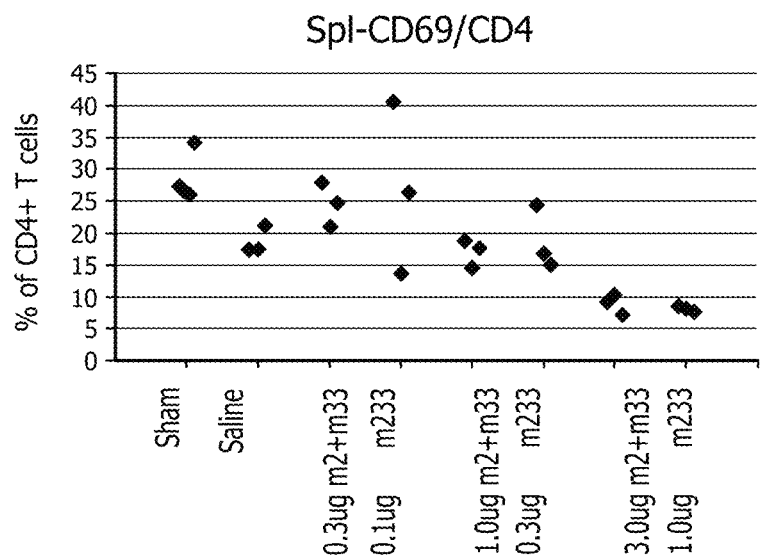
Figure 7D:
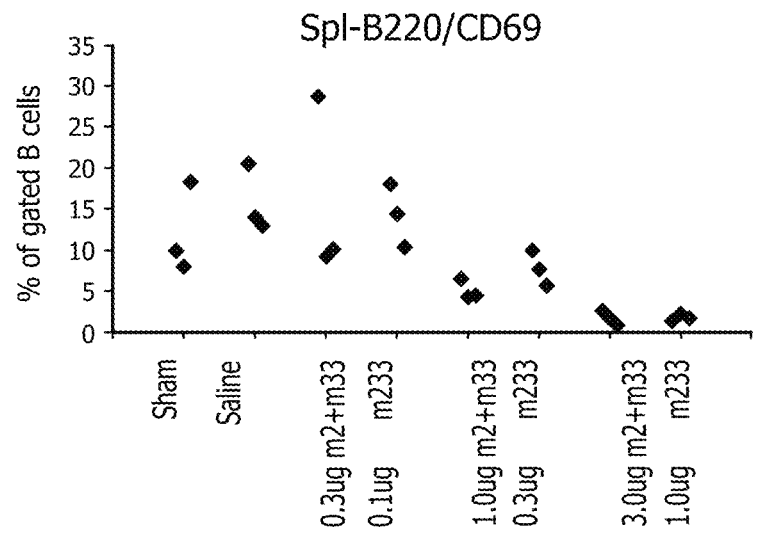
Figure 7E:
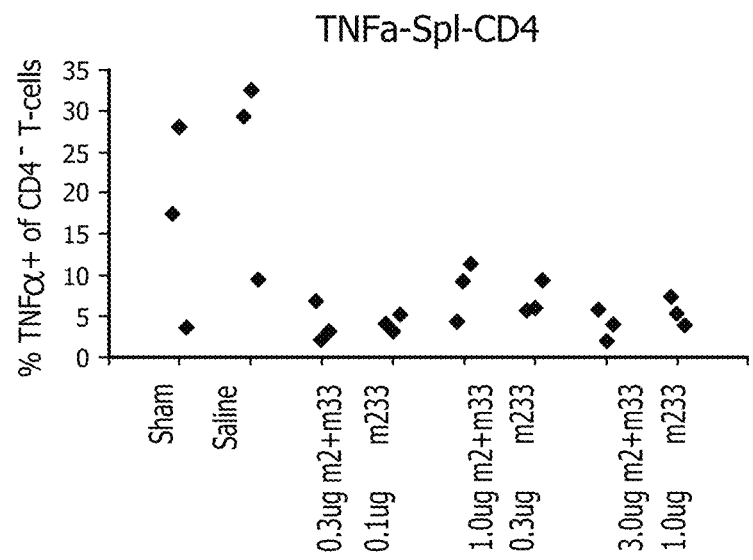
Figure 7F:
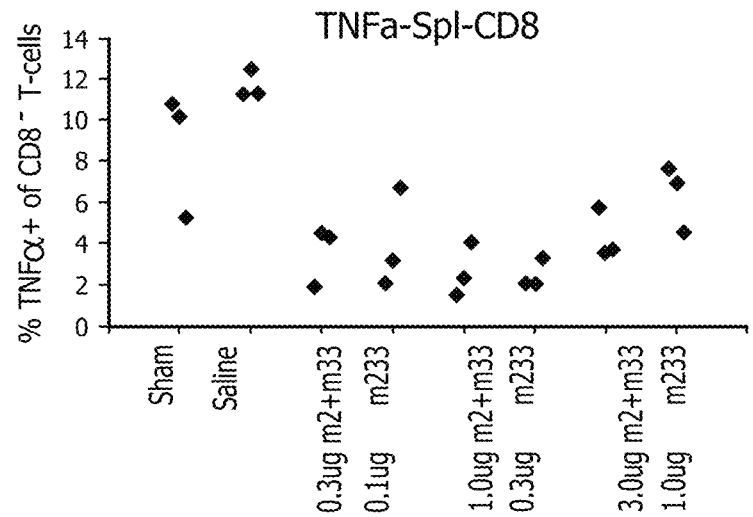

Non-obese diabetic mice with early diabetes (blood glucose 150±10 mg/dL) were injected once with a 5-daily dose of 1.0 µg equivalent IL-2 or IL-33 or combination of IL-2 and IL-33 or IL233 hybrid cytokine. The control mice were injected with saline. Six weeks post-treatment, the mice that recovered from hyperglycemia or the mice that were severely diabetic (blood glucose of 600 mg/dL for two consecutive days) were euthanized and the spleen and pancreatic lymph nodes were analyzed for the CD4+Foxp3+ Treg cells. (See FIG. 6).

7. Treatment with IL233 or Mixture of IL-2 and IL-33 Protects C57BL/6 Mice from Renal Ischemia Reperfusion Injury (IRI).

C57BL/6 mice were treated with 5 daily doses of the indicated amounts of a combination of murine IL-2 (m2) and IL-33 (m33) or with murine IL233 fusion cytokine (m233). On day 7, the renal pedicle was clamped for 26 minutes followed by 18 hours reperfusion. High plasma creatinine levels indicate loss of kidney function. Unexpectedly, the IL233 fusion was 3-fold more effective than the mixture of IL-2 and IL-33 in protecting mice against loss of renal function and inflammation as measure by Plasma creatinine levels (A) or Histological score. (B). The protection was accompanied with reduction of the activated CD4+ T cells (C), CD8+ T-cells (not shown) and activated B-cells (D) in the spleen. TNFα producing CD4 (E) and CD8 (F) T-cells and IFN-γ producing cells (not shown) were also reduced by the cytokine treatment as measured by flow cytometry of the cells isolated from the spleen. (See FIG. 7).

8. Treatment with IL233 Protects Lupus Prone NZM2328 Mice from Lupus Glomerulonephritis (GN).

Three-month-old NZM2328 female mice (5 mice per group) were injected with recombinant IL-2 or IL233 fusion protein (1 µg IL-2 molar equivalent of each) daily for 5 days (green arrows). The control mice received saline only. On day 12 all the mice with injected with Ad-IFNα (adenovirus expressing IFNα) to accelerate the lupus nephritis (red double-headed arrow). The mice were monitored periodically for kidney function (proteinuria with dip stick) and mortality. (A) The peripheral blood of mice was analyzed on d1 and d9 of the recombinant cytokine treatment. Treatment with both IL-2 and IL233 resulted in an increase in the Treg levels, as measured by flow cytometry. Treatment with IL233, but not IL-2 resulted in a decrease in the production of TNF-α (a pro-inflammatory cytokine known to contribute to lupus GN) as measured by intracellular staining of lymphocytes for TNF-α after a 5-hour ex-vivo stimulation with Phorbol myristate acetate and Ionomycin. Individual mice are shown. (B) Proteinuria was measured by dipstick and mice with a "+++" score on the dipstick were considered to have severe proteinuria (top). The data is presented as "percent proteinuria free". The control mice (Blue) developed severe proteinuria rapidly, while treatment with IL-2 (red) protected partially. The mice treated with IL233 (green) were completely protected against severe proteinuria at the termination of the experiment. IL233 treatment offered complete protection against mortality, which IL-2 treatment protected partially (bottom). (See FIG. 8).

9. Treatment with IL233 as Well as the IL-2 and IL-33 Combination is More Effective than Either Cytokine Alone to Protect Lupus Prone NZM2328 Mice from GN.

In a similar experiment, 3-month old NZM2328 mice were injected for 5 consecutive days (green arrow) with 1 µg molar equivalent daily of IL-2, IL-33, a mixture of IL-2 and IL-33, or IL233. Three days later mice were injected with Adenovirus expressing IFNα to accelerate lupus GN. A) Combined treatment with IL-2 and IL-33, especially as a IL233 cytokine protected NZM2328 mice from severe proteinuria (top) and mortality (bottom) in IFNα-induced accelerated GN (green arrows-cytokine treatment; red arrows IFNα; n=5). B) Representative H & E stained kidney sections show enlarged glomeruli (highlighted by black-dotted circle; higher magnification in the inset), mesangial expansion, glomerulosclerosis (inset) and leukocytic infiltration in the control mice, but not in the IL233-treatment group (quantified in C). D) IL233 treatment, although inhibited glomerular hypertrophy, did not significantly alter Complement C3 and total IgG immune complex deposition. E) IL233 treatment skewed the circulating anti-dsDNA antibodies from IgG2a to IgG2b, p<0.01; n=3. IL233 treatment increased Foxp3+ Tregs as measured in the lymph node (LN) of mice (F) leading to lower ratios of Tregs to IFNγ+(G) & TNFα+(H) CD4 T-cells when analyzed 12-wks post initial treatment or when the control of IL-2 or IL-33 treated mice were moribund. ♦=individual mice; bar=mean. (See FIG. 9).

10. Treatment with IL233 Inhibits Progression of Obesity, Type-2 Diabetes (T2D) and Diabetic Nephropathy in Mice Genetically Predisposed for Obesity.

Five to six weeks old BTBR.ob/ob (Ob-obese mice, due to mutation in Leptin gene) or BTBR.ob/+(Het, non-obese mice) were treated once with 5-daily doses of 50 µg/kg of IL233 or saline (green arrows). The mice were monitored for CD4+Foxp3+ Tregs (A), body weight (B), blood glucose (C), proteinuria (D). The glucose tolerance of the mice treated with IL233 also improved to near non-obese levels (E). As shown below IL233 treatment increased the Treg levels, inhibited weight gain, hyperglycemia, and proteinuria, and restored glucose tolerance. (See FIG. 10).

11. Preparation of Human and Murine IL233 Fusion Proteins

The nucleotide sequences of the nucleic acids encoding the fusion proteins and the amino acid sequences of the recombinant IL233 fusion proteins are depicted in FIG. 11. The Blue color denotes the IL-2 coding sequence, the red color is the IL-33 encoding sequence, the black residues are the linker segments added to provide flexibility to the fusion protein, and the yellow highlighted part codes for the TEV protease cleave site. The major restriction sites are underlined. (See FIG. 11). The sequences are also provided in the Sequence Listing and in the Summary of the Invention.

We synthesized nucleic acids comprising nucleic acid sequences encoding human and murine IL-2 (human amino acid residues 21-153; murine amino acid residues 21-169) and IL-33 (human amino acid residues 112-270; murine amino acid residues 109-266) that were optimized for *E. coli* codon bias. The cytokines were produced in *E. coli* and purified to near homogeneity.

Recombinant Human IL233 Hybrid Cytokine: (See FIGS. 11-13)

Novel hybrid cytokines were generated consisting of mature IL-2 (residues 21-153) and mature IL-33 (residues 112-270) proteins separated by a short linker (GGGGSGGGGSGGGGS) sequence (SEQ ID NO:5). The fusion protein is named IL233 (hIL233) and was produced in *E. coli*. The coding sequence for the IL233 fusion protein has been synthesized using optimized codon sequences for high-level expression. The sequence of the synthetic gene for the IL233 fusion protein is given in FIG. 11. The gene was synthesized using overlapping oligonucleotides and amplified using Polymerase Chain Reaction (PCR) with Deep Vent™ DNA polymerase (New England Biolabs). The coding sequence was cloned as an in-frame fusion with NusA coding sequence in the pET44a expression vector (Novagen Inc.), under the control of T7 promoter. This strategy results in a fusion protein consisting of (His)6-NusA-TEV linker-rhIL2(21-153)-linker-rhIL33 (112-270).

For generating the expression vector, the PCR product was digested with EcoRI and XhoI restriction enzymes (New England Biolabs). The pET44a vector was digested with EcoRI (New England Biolabs) and XhoI restriction enzymes. Both DNA fragments were purified on agarose gel and ligated to each other using T4 DNA ligase (Bioline Inc.) and used to transform E. coli DH5a competent cells. The positive clones were selected on Luria Bertani (LB) agar plates containing 100 µg/ml Ampicillin.

Recombinant Murine IL233 Hybrid (mIL233) Cytokine:

To establish the proof of concept we produced the murine version of the recombinant cytokines. The plasmid vector and techniques were the same as for human IL233, the only difference being the use of mouse IL-2 and IL-33 genes. The gene for mouse IL-2 coding sequence was amplified by reverse transcriptase PCR using C57BL/6 (B6) spleen mRNA as a template and the mouse IL-33 coding sequence was synthesized. The coding sequence for mouse IL-2 (mIL-2; residues 21-169) and IL-33 (mIL-33; residues 109-266) were linked with the coding sequence for a flexible linker as for human IL233, thus generating (His)6-NusA-TEV linker-rmIL2(21-169)-linker-rmIL-33 (109-266). The DNA and protein sequences for the murine version of IL233 (mIL233) are given below in FIGS. 11C and 11D respectively.

The expression vector for mouse or human IL233 was used to transform E. coli Rosetta-gami™ competent cells (Novagen Inc.). The expression of the protein was induced with 0.1 mM IPTG and the protein was partially purified using immobilized metal-affinity chromatography on NI-NTA-Agarose™ resin (Qiagen Inc.) using the manufacturer's protocol. The (His)6-NusA-linker was removed by digestion with TEV protease (Sigma Aldrich Inc.) and purified using ion exchange and size-exclusion chromatography. The final product was dialyzed against Phosphate buffered saline (PBS), quantified using Coomassie blue reagent and stored in aliquots at −80° C. The sequence of the final fusion protein is given in FIG. 11.

The potential mode of action of the fusion protein can be envisioned in FIG. 12. The IL233 fusion protein (FIG. 12A) can induce proliferation and activation cells bearing the receptors for IL-2 and IL-33 in an autologous (FIG. 12B) or fraternal manner (FIG. 12C). The fusion protein can also induce recruitment of Treg, Th2 or ILC cells to the sites of inflammation to either suppress the pro-inflammatory Th1, Th17 or NK cells (FIG. 11D left) or induce tolerance by imparting a Th2 skewing or altered maturation phenotype on the antigen presenting DC/macrophages (FIG. 11D right).

We demonstrated that a treatment of mice with a combination of low-dose IL-2 and IL-33 or with the mIL233 hybrid cytokine was effective in suppressing the onset of hyperglycemia in a mouse model of type-1 diabetes (T1D). We also showed that treatment of mice with the combination of low-dose IL-2 and IL-33 as well as IL233 also offered protection against acute kidney injury in a mouse model of ischemia reperfusion. The IL-2 and IL-33 combination therapy and more effectively as the IL233 cytokine were, protective in a mouse model of lupus glomerulonephritis as compared to either cytokine alone. It is also demonstrated that the IL233 cytokine protected against obesity, type-2 diabetes (T2D), and obesity-linked diabetic nephropathy using a mouse model.

12. Different Modes of Action of the IL233 Fusion Protein.

To provide an example of the modes and potential mechanisms of action of the fusion protein, a schematic representation of the IL233 fusion protein and its receptors and action is provided in FIG. 12. IL233 may bind to two receptors on the same cell (B) or on adjacent cells bearing the receptors for IL-2 and IL-33 (C). In a multimeric complex of cells, IL233 binding to Tregs, Th2, or ILC2 on one end and to antigen presenting cell (DC or macrophages) on the other hand may induce tolerance resulting in suppression of Th1, TH17, or TfH activation. (See FIG. 12).

13. Proposed Model of Using Combinations of IL-2 and IL-33 or a Fusion Protein of IL-2 and IL-33.

Without wishing to be bound by any particular theory, it was hypothesized herein that, owing to the constitutive expression of the receptors for IL-2 and IL-33 on the natural Tregs, Th2 cells and Innate Lymphoid cells type 2 (ILC2), combining the activities of IL-2 and IL-33 could invoke multiple mechanisms for suppression of autoimmune and inflammatory diseases. FIG. 13 provides a schematic representation of the model and actions, which include: (a) activation and recruitment of Tregs/ILC2 for peripheral tolerance; (b) skewing of the immune response towards Th2 for suppression of the pro-inflammatory Th1 and Th17 cells; (c) inhibiting the T-follicular helper (TfH) cells, which induce high-affinity autoantibodies; and (d) induce tolerogenic alternately activated macrophages. Owing to the high-level constitutive expression of the receptors for both IL-2 and IL-33, a treatment with combination of IL-2 and IL-33 will increase the targeting of nTregs, Th2 and ILC2. (See FIG. 13).

IL-33 and Treg Cells:

We have identified high-level expression of the IL-33 receptor IL1RL1 on Treg cells (data not shown). Our data show little or no IL1RL1 expression of naïve T-cells (Tn) or when the Tn are stimulated in the absence of antigen-presenting cells (APC) and under the conditions to induce Th1, Th2 or iTreg cells. However, IL1RL1 was constitutively expressed at high levels on the nTreg cells and the level was further increased upon stimulation in the presence of IL-2 (data not shown).

CONCLUSIONS

Without wishing to be bound by any particular theory, it is hypothesized that IL-2 in conjunction with IL-33 is important for the maintenance and function of Treg cells, where IL-33 provides the innate signal, while IL-2 provides the adaptive signal for the adequate maintenance of Treg homeostasis and function. Indeed, studies from other groups have recently demonstrated that IL-33 can boost the Treg-mediated allograft survival in rodent models and also protection against experimental colitis (10).

The application discloses a therapy utilizing a combination of cytokines, that simultaneously promote T-regulatory (Treg) cells and T-helper 2 (Th2 that produce IL-4, IL-5, and IL-13) and that suppress autoimmunity and inflammation by inhibiting the pro-inflammatory Th1 and Th17 cells which produce Interferon (IFN)-gamma and IL-17. The Treg, Th2, and recently discovered innate lymphoid cells (ILC2) highly express the receptors for IL-2 and IL-33. It is proposed herein that a combination therapy with IL-2 and IL-33 will simultaneously promote Treg and Th2 responses to offer long-term protection against autoimmunity and inflammation by suppressing the Th1 and Th17 responses as well as inhibiting activation of several other pro-inflammatory immune cells.

Figures 3A, 3B:
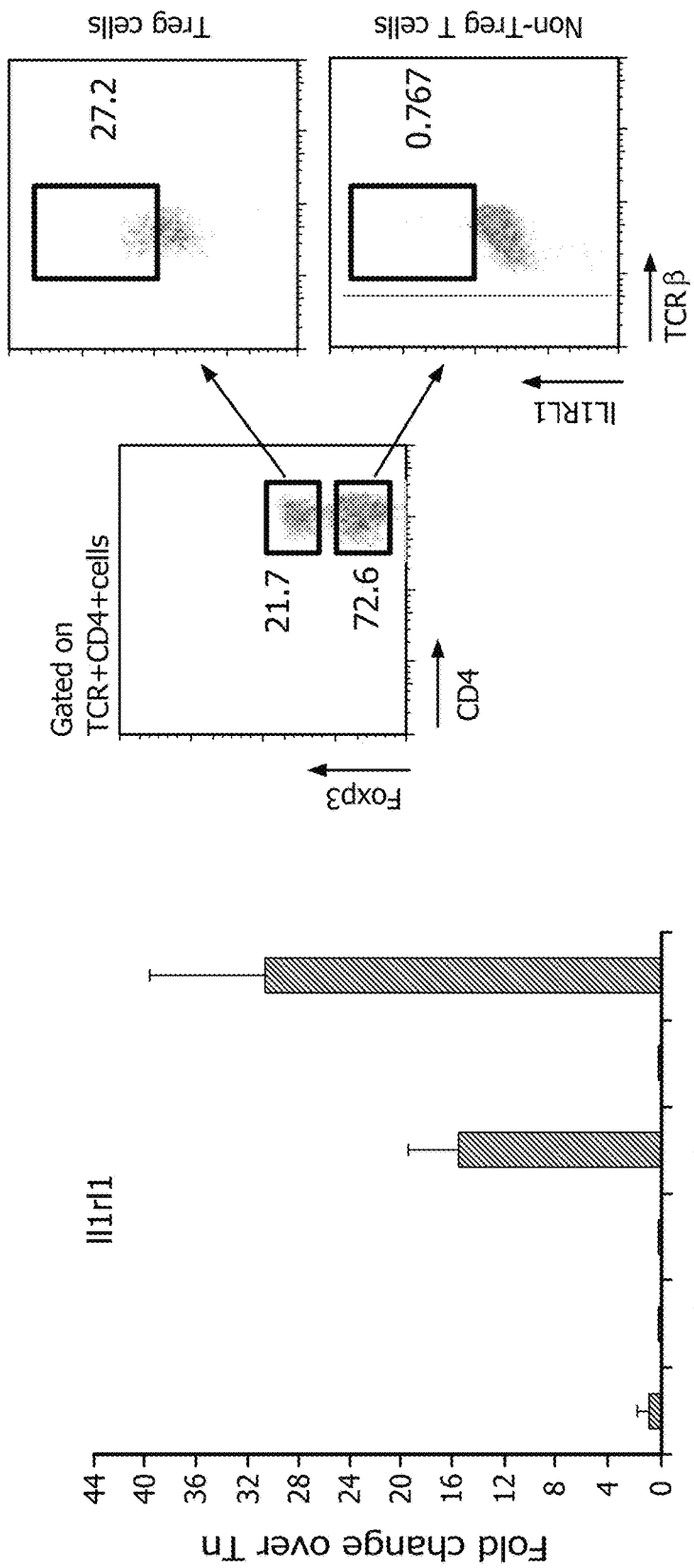
FIG. 3. The natural Tregs (nTr) express IL-33 receptor (IL1RL1). (A). IL1RL1 expression was measured by real-time PCR on FACS sorted natural Tregs (nTr) cells. FACS sorted naïve cells (Tn) were differentiated in vitro into induced Tregs (iTr), effector cells (Teff), Th1, or Th2 cells and analyzed for IL1RL1 expression. FACS sorted naïve T-cells (Tn) were used as a control. (B) Expression of IL1RL1 as gated on Tregs and non-Tregs was analyzed by flow cytometry.

Potential Uses of the Combination Therapy and the IL233 Hybrid Cytokine:

Without wishing to bound by any particular theory, it is hypothesized herein that that the synergy of IL-2 and IL-33 will induce multiple protective mechanisms, which may include, but not limited to expanding and activating Tregs, Th2 and ILC2 cells, skewing of immune response and induction of alternately activated macrophages to protect from autoimmune and inflammatory diseases by suppressing Th1, Th17 and TfH cell responses (FIG. 3). Some uses of the invention are listed below:

1. The IL233 fusion protein can be used for treatment of inflammatory conditions via boosting the homeostasis and activity of Treg cells, which offer the major mechanism of peripheral immune tolerance.

2. The IL233 fusion protein can be used to potentiate the Th2 response by increasing the production of the related cytokines (IL-4, IL-5, and IL-13) by the differentiated Th2 cells, the innate lymphoid cells, Nuocytes, natural helper cells or fat associated lymphoid cluster (FALC).

3. The invention can be used for skewing of the immune response by inhibiting the pro-inflammatory Th1 response and boosting the anti-inflammatory Th2 immune response.

4. The invention can be used for altering the phenotype of innate immune cells, such as dendritic cells (DC) and macrophages to an altered maturation phenotype, such that these innate immune cells can skew the differentiation of immune response towards a Th2 response, while suppressing the Th1 differentiation. The IL233 treated DC and macrophages can also be employed for boosting the homeostasis of Treg cells.

5. The function described above can either individually or in cooperation be used for suppression of initiation or cure of, for example, autoimmune disorders including Type-1 diabetes, Type-2 diabetes, multiple sclerosis, atherosclerosis, systemic lupus erythematosus (lupus), autoimmune pancreatitis, IgG4-related systemic disease spectrum diseases (IgG4-RSD), Sjogren's syndrome, inflammatory bowel disease (Crohn's disease, and ulcerative colitis), autoimmune thyroiditis, autoimmune encephalomyelitis, Alzheimer's disease & dementia, ankylosing spondylitis, chronic obstructive pulmonary disease, myasthenia gravis, obesity, osteoporosis, periodontal disease, psoriasis and uveitis.

6. The IL233 fusion protein can be employed for boosting immune tolerance during transplantation for enhancing graft survival via boosting the homeostasis and recruitment of Treg and Th2 cells.

7. The invention can be employed for treatment of inflammatory conditions arising due to ischemia reperfusion injury of various organs including, kidneys, lung and heart.

8. The IL233 treatment can be employed for protection in cardio-vascular diseases by not only suppressing inflammation, but also by improving cardio-vascular function. Treatment with IL-33 has been demonstrative to have cardio-protective properties in a model of pressure overload and improved survival following transverse aortic constriction in wild-type but not IL-33 receptor mice. IL-33 can also reduce cardiomyocyte apoptosis, decrease infarct and fibrosis, and improve ventricular function in vivo via suppression of caspase-3 activity and increased expression of the 'inhibitor of apoptosis' family of proteins.

9. The IL233 fusion protein can be used to not only suppress inflammation in the central nervous system, but will also be useful in promoting the homeostasis of microglia cells. This activity can be employed is treatment of several neurological disorders linked with microglia-cell related defects such as Rhett syndrome.

10. The IL233 fusion protein can be employed to reduce inflammation in the adipose tissue by altering the phenotype of the adipose tissue resident macrophages to an altered maturation phenotype, which will suppress the inflammation associated with obesity and Type-2 diabetes. The fusion protein will also be useful for suppression of adipogenesis, because IL-33 has been shown to suppress the expression of several genes related to adipogenesis and improve fasting glucose levels as well as resistance to insulin and glucose in mouse model of type-2 diabetes.

11. The IL233 fusion protein will also suppress the inflammatory co-morbidities associated with diabetes, such as diabetic nephropathy, retinopathy, and neuropathy.

The novelty of this invention, based on the unexpected identification of the common high-level expression of the receptors for IL-2 and IL-33 on the Treg cells, Th2 cells and the ILC, is the unexpected finding that the combination of IL-2 and IL-33 activities can be employed to boost Treg and Th2 responses to inhibit and resolve autoimmune and inflammatory diseases via suppression of the pro-inflammatory Th1, Th17 and TfH responses. Additionally, the present invention now provides the design of a fusion protein that has the activities of both these cytokines, which are important for immunological tolerance, in one molecule, to improve the specificity and avidity of both the activities for use as an anti-inflammatory agent. Further disclosed herein is the wide repertoire of the mode of action of the fusion protein, wherein it was found to be successful in exploiting multiple tolerogenic mechanisms, which include, but are not limited to, regulation of Tregs, Th2 cells, ILC, Dendritic cells, macrophages, neuronal cells (microglia and astrocytes) and adipocytes.

A common problem in treatment with soluble factors is the non-specificity of the therapeutic approach. Current technologies for the treatment of autoimmune and inflammatory conditions (including organ transplantation) employ strategies, which include either complete immune-suppression or blocking of one aspect of the immune response, which either lead to infections or are ineffective respectively. Here, we propose to enhance the body's in built protective mechanisms, which will work on several aspects of the innate and adaptive simultaneously for effective expression of immunological tolerance.

Use of IL-2 to expand regulatory T-cells either alone or as a complex with anti-IL-2 monoclonal antibody has been used in animal models. However, since the anti-IL-2 antibody is a large foreign molecule, it will induce immune response against itself and will soon be rendered ineffective. Furthermore, such techniques only target one cell type. The present invention targets multiple cell-types of immune system and employs multiple mechanisms of immunological tolerance.

Both IL-2 and IL-33 are pleiotropic cytokines and work on multiple cell-types. Although, the highest expression of IL-2 receptor is found on the Treg cells, IL-2 receptor is present on multiple cell types. The high-affinity IL-2 receptor CD25 is also expressed on activated $CD4^+$ and $CD8^+$ T-cells as well as B-cells. Nevertheless, the Treg cells have the highest constitutive expression of CD25 and consumption of IL-2 via its high-affinity receptor comprises one of the major mechanisms of suppression employed by the Tregs. The invention therefore provides compositions and methods to increase the specificity of the IL-2 and IL-33 activities as a covalently linked fusion protein, which selectively targets the cells that are enriched for the receptors for both. Such cells include Treg cells, Th2 cells and ILC/Nuocytes, which have important functions in regulation of inflammation. The invention will also induce the recruitment of Treg, Th2, and ILC to other cell types, which express only one of the two receptors for IL-2 and IL-33 (see FIGS. 11-13).

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Boyman O, Sprent J. 2012. The role of interleukin-2 during homeostasis and activation of the immune system. Nat Rev Immunol 12: 180-90
2. Wing J B, Sakaguchi S. 2012. Multiple treg suppressive modules and their adaptability. Front Immunol 3: 178
3. Josefowicz S Z, Lu L F, Rudensky A Y. 2012. Regulatory T cells: mechanisms of differentiation and function. Annu Rev Immunol 30: 531-64
4. Tang Q, Bluestone J A, Kang S M. 2012. CD4(+)Foxp3(+) regulatory T cell therapy in transplantation. J Mol Cell Biol 4: 11-21
5. Shevach E M. 2011. Biological functions of regulatory T cells. Adv Immunol 112: 137-76
6. Altin J A, Goodnow C C, Cook M C. 2012. IL-10+ CTLA-4+ Th2 inhibitory cells form in a Foxp3-independent, IL-2-dependent manner from Th2 effectors during chronic inflammation. J Immunol 188: 5478-88
7. Tran G T, Hodgkinson S J, Carter N M, Verma N D, Plain K M, Boyd R, Robinson C M, Nomura M, Killingsworth M, Hall B M. 2012. IL-5 promotes induction of antigen-specific CD4+CD25+ T regulatory cells that suppress autoimmunity Blood 119: 4441-50
8. Seki T, Kumagai T, Kwansa-Bentum B, Furushima-Shimogawara R, Anyan W K, Miyazawa Y, Iwakura Y, Ohta N. 2012. Interleukin-4 (IL-4) and IL-13 suppress excessive neutrophil infiltration and hepatocyte damage during acute murine schistosomiasis *japonica*. Infect Immun 80: 159-68
9. Oliphant C J, Barlow J L, McKenzie A N. 2011. Insights into the initiation of type 2 immune responses. Immunology 134: 378-85
10. Duan L, Chen J, Zhang H, Yang H, Zhu P, Xiong A, Xia Q, Zheng F, Tan Z, Gong F, Fang M. 2012. Interleukin-33 Ameliorates Experimental Colitis through Promoting Th2/Foxp3(+) Regulatory T-Cell Responses in Mice. Mol Med 18: 753-61
11. Brunner S M, Schiechl G, Falk W, Schlitt H J, Geissler E K, Fichtner-Feigl S. 2011. Interleukin-33 prolongs allograft survival during chronic cardiac rejection. Transpl Int 24: 1027-39
12. Ikutani M, Yanagibashi T, Ogasawara M, Tsuneyama K, Yamamoto S, Hattori Y, Kouro T, Itakura A, Nagai Y, Takaki S, Takatsu K. 2012. Identification of innate IL-5-producing cells and their role in lung eosinophil regulation and antitumor immunity. J Immunol 188: 703-13
13. Barlow J L, McKenzie A N. 2011. Nuocytes: expanding the innate cell repertoire in type-2 immunity. J Leukoc Biol 90: 867-74
14. Sharma R, Sung S S, Gaskin F, Fu S M, Ju S T. 2012. A novel function of IL-2: chemokine/chemoattractant/ retention receptor genes induction in Th subsets for skin and lung inflammation. J Autoimmun 38: 322-31
15. Sharma R, Fu S M, Ju S T. 2011. IL-2: a two-faced master regulator of autoimmunity J Autoimmun 36: 91-7
16. Sharma R, Sharma P R, Kim Y C, Leitinger N, Lee J K, Fu S M, Ju S T. 2011. IL-2-controlled expression of multiple T cell trafficking genes and Th2 cytokines in the regulatory T cell-deficient scurfy mice: implication to multiorgan inflammation and control of skin and lung inflammation. J Immunol 186: 1268-78
17. Sharma R, Sung S S, Abaya C E, Ju A C, Fu S M, Ju S T. 2009. IL-2 regulates CD103 expression on CD4+ T cells in Scurfy mice that display both CD103-dependent and independent inflammation. J Immunol 183: 1065-73
18. Zheng L, Sharma R, Gaskin F, Fu S M, Ju S T. 2007. A novel role of IL-2 in organ-specific autoimmune inflammation beyond regulatory T cell checkpoint: both IL-2 knockout and Fas mutation prolong lifespan of Scurfy mice but by different mechanisms. J Immunol 179: 8035-41
19. Cheng G, Yu A, Malek T R. 2011. T-cell tolerance and the multi-functional role of IL-2R signaling in T-regulatory cells. Immunol Rev 241: 63-76
20. Malek T R, Castro I. 2010. Interleukin-2 receptor signaling: at the interface between tolerance and immunity. Immunity 33: 153-65
21. Dooms H, Abbas A K. 2010. Revisiting the role of IL-2 in autoimmunity. Eur J Immunol 40: 1538-40
22. Malek T R. 2003. The main function of IL-2 is to promote the development of T regulatory cells. J Leukoc Biol 74: 961-5
23. Ruffner M A, Robbins P D. 2010. Dendritic cells transduced to express interleukin 4 reduce diabetes onset in both normoglycemic and prediabetic nonobese diabetic mice. PLoS One 5: e11848
24. Rabinovitch A, Suarez-Pinzon W L. 2007. Roles of cytokines in the pathogenesis and therapy of type 1 diabetes. Cell Biochem Biophys 48: 159-63
25. Gregory G D, Raju S S, Winandy S, Brown M A. 2006. Mast cell IL-4 expression is regulated by Ikaros and influences encephalitogenic Th1 responses in EAE. J Clin Invest 116: 1327-36
26. Xu L Y, Huang Y M, Yang J S, Van Der Meide P H, Link H, Xiao B G. 2000. Suppression of ongoing experimental allergic encephalomyelitis (EAE) in Lewis rats: synergistic effects of myelin basic protein (MBP) peptide 68-86 and IL-4. Clin Exp Immunol 120: 526-31
27. He X Y, Chen J, Verma N, Plain K, Tran G, Hall B M. 1998. Treatment with interleukin-4 prolongs allogeneic neonatal heart graft survival by inducing T helper 2 responses. Transplantation 65: 1145-52
28. Davidson C, Verma N D, Robinson C M, Plain K M, Tran G T, Hodgkinson S J, Hall B M. 2007. IL-13 prolongs allograft survival: association with inhibition of macrophage cytokine activation. Transpl Immunol 17: 178-86
29. Lu M, Dawicki W, Zhang X, Huang H, Nayyar A, Gordon J R. 2011. Therapeutic induction of tolerance by IL-10-differentiated dendritic cells in a mouse model of house dust mite-asthma. Allergy 66: 612-20
30. Verma N D, Plain K M, Nomura M, Tran G T, Robinson C, Boyd R, Hodgkinson S J, Hall B M. 2009. CD4+CD25+ T cells alloactivated ex vivo by IL-2 or IL-4 become potent alloantigen-specific inhibitors of rejection with different phenotypes, suggesting separate pathways of activation by Th1 and Th2 responses. Blood 113: 479-87

31. Turnquist H R, Zhao Z, Rosborough B R, Liu Q, Castellaneta A, Isse K, Wang Z, Lang M, Stolz D B, Zheng X X, Demetris A J, Liew F Y, Wood K J, Thomson A W. 2011. IL-33 expands suppressive CD11b+Gr-1(int) and regulatory T cells, including ST2L+Foxp3+ cells, and mediates regulatory T cell-dependent promotion of cardiac allograft survival. J Immunol 187: 4598-610

32. Nurieva R I, Podd A, Chen Y, Alekseev A M, Yu M, Qi X, Huang H, Wen R, Wang J, Li H S, Watowich S S, Qi H, Dong C, Wang D. 2012. STAT5 Protein Negatively Regulates T Follicular Helper (Tfh) Cell Generation and Function. J Biol Chem 287: 11234-9

33. Johnston R J, Choi Y S, Diamond J A, Yang J A, Crotty S. 2012. STAT5 is a potent negative regulator of TFH cell differentiation. J Exp Med 209: 243-50

34. Solomou E E, Juang Y T, Gourley M F, Kammer G M, Tsokos G C. 2001. Molecular basis of deficient IL-2 production in T cells from patients with systemic lupus erythematosus. J Immunol 166: 4216-22

35. Dendrou C A, Wicker L S. 2008. The IL-2/CD25 pathway determines susceptibility to T1D in humans and NOD mice. J Clin Immunol 28: 685-96

36. Fransson M, Burman J, Lindqvist C, Atterby C, Fagius J, Loskog A. 2010. T regulatory cells lacking CD25 are increased in MS during relapse. Autoimmunity 43: 590-7

37. Alcina A, Fedetz M, Ndagire D, Fernandez O, Leyva L, Guerrero M, Abad-Grau M M, Arnal C, Delgado C, Lucas M, Izquierdo G, Matesanz F. 2009. IL2RA/CD25 gene polymorphisms: uneven association with multiple sclerosis (MS) and type 1 diabetes (T1D). PLoS One 4: e4137

38. Gomez-Tourino I, Sanchez-Espinel C, Hernandez-Fernandez A, Gonzalez-Fernandez A, Pena-Gonzalez E, Rodriguez J, Garcia-Lopez J M, Varela-Calvino R. 2011. Galectin-1 synthesis in type 1 diabetes by different immune cell types: reduced synthesis by monocytes and Th1 cells. Cell Immunol 271: 319-28

39. Oling V, Geubtner K, Ilonen J, Reijonen H. 2010. A low antigen dose selectively promotes expansion of high-avidity autoreactive T cells with distinct phenotypic characteristics: a study of human autoreactive CD4+T cells specific for GAD65. Autoimmunity 43: 573-82

40. Ryden A, Stechova K, Durilova M, Faresjo M. 2009. Switch from a dominant Th1-associated immune profile during the pre-diabetic phase in favour of a temporary increase of a Th3-associated and inflammatory immune profile at the onset of type 1 diabetes. Diabetes Metab Res Rev 25: 335-43

41. Neill D R, Wong S H, Bellosi A, Flynn R J, Daly M, Langford T K, Bucks C, Kane C M, Fallon P G, Pannell R, John H E, McKenzie A N. 2010. Nuocytes represent a new innate effector leukocyte that mediates type-2 immunity. Nature 464: 1367-70

42. Spits H, Cupedo T. 2012. Innate lymphoid cells: emerging insights in development, lineage relationships, and function. Annu Rev Immunol 30: 647-75

43. Wilhelm C, Stockinger B. 2011. Innate lymphoid cells and type 2 (th2) mediated immune responses—pathogenic or beneficial? Front Immunol 2: 68

44. Mjosberg J M, Trifari S, Crellin N K, Peters C P, van Drunen C M, Piet B, Fokkens W J, Cupedo T, Spits H. 2011. Human IL-25- and IL-33-responsive type 2 innate lymphoid cells are defined by expression of CRTH2 and CD161. Nat Immunol 12: 1055-62

45. Yasuda K, Muto T, Kawagoe T, Matsumoto M, Sasaki Y, Matsushita K, Taki Y, Futatsugi-Yumikura S, Tsutsui H, Ishii K J, Yoshimoto T, Akira S, Nakanishi K. 2012. Contribution of IL-33-activated type II innate lymphoid cells to pulmonary eosinophilia in intestinal nematode-infected mice. Proc Natl Acad Sci USA 109: 3451-6

46. Bartemes K R, Iijima K, Kobayashi T, Kephart G M, McKenzie A N, Kita H. 2012. IL-33-responsive lineage-CD25+CD44(hi) lymphoid cells mediate innate type 2 immunity and allergic inflammation in the lungs. J Immunol 188: 1503-13

47. Liew F Y. 2012. IL-33: a Janus cytokine. Ann Rheum Dis 71 Suppl 2: i101-4

48. Palmer G, Gabay C. 2011. Interleukin-33 biology with potential insights into human diseases. Nat Rev Rheumatol 7: 321-9

49. Kunes P, Holubcova Z, Kolackova M, Krejsek J. 2010. Interleukin-33, a novel member of the IL-1/IL-18 cytokine family, in cardiology and cardiac surgery. Thorac Cardiovasc Surg 58: 443-9

50. Oboki K, Ohno T, Kajiwara N, Saito H, Nakae S. 2010. IL-33 and IL-33 receptors in host defense and diseases. Allergol Int 59: 143-60

51. Zhao W, Hu Z. 2010. The enigmatic processing and secretion of interleukin-33. Cell Mol Immunol 7: 260-2

52. Kakkar R, Lee R T. 2008. The IL-33/ST2 pathway: therapeutic target and novel biomarker. Nat Rev Drug Discov 7: 827-40

53. Arend W P, Palmer G, Gabay C. 2008. IL-1, IL-18, and IL-33 families of cytokines. Immunol Rev 223: 20-38

54. Perrigoue J G, Marshall F A, Artis D. 2008. On the hunt for helminths: innate immune cells in the recognition and response to helminth parasites. Cell Microbiol 10: 1757-64

55. Besnard A G, Togbe D, Guillou N, Erard F, Quesniaux V, Ryffel B. 2011. IL-33-activated dendritic cells are critical for allergic airway inflammation. Eur J Immunol 41: 1675-86

56. Turnquist H R, Thomson A W. 2009. IL-33 broadens its repertoire to affect DC. Eur J Immunol 39: 3292-5

57. Rank M A, Kobayashi T, Kozaki H, Bartemes K R, Squillace D L, Kita H. 2009. IL-33-activated dendritic cells induce an atypical TH2-type response. J Allergy Clin Immunol 123: 1047-54

58. Jiang H R, Milovanovic M, Allan D, Niedbala W, Besnard A G, Fukada S Y, Alves-Filho J C, Togbe D, Goodyear C S, Linington C, Xu D, Lukic M L, Liew F Y. 2012. IL-33 attenuates EAE by suppressing IL-17 and IFN-gamma production and inducing alternatively activated macrophages. Eur J Immunol 42: 1804-14

FY. 2011. IL-33 activates B1 cells and exacerbates contact sensitivity. J Immunol 186: 2584-91

60. Gronwall C, Vas J, Silverman G J. 2012. Protective Roles of Natural IgM Antibodies. Front Immunol 3: 66

61. Kaveri S V, Silverman G J, Bayry J. 2012. Natural IgM in immune equilibrium and harnessing their therapeutic potential. J Immunol 188: 939-45

62. Hoshino K, Kashiwamura S, Kuribayashi K, Kodama T, Tsujimura T, Nakanishi K, Matsuyama T, Takeda K, Akira S. 1999. The absence of interleukin 1 receptor-related T1/ST2 does not affect T helper cell type 2 development and its effector function. J Exp Med 190: 1541-8

63. Mangan N E, Dasvarma A, McKenzie A N, Fallon P G. 2007. T1/ST2 expression on Th2 cells negatively regulates allergic pulmonary inflammation. Eur J Immunol 37: 1302-12

64. McLaren J E, Michael D R, Salter R C, Ashlin T G, Calder C J, Miller A M, Liew F Y, Ramji D P. 2010. IL-33 reduces macrophage foam cell formation J Immunol 185: 1222-9

65. Miller A M, Xu D, Asquith D L, Denby L, Li Y, Sattar N, Baker A H, McInnes I B, Liew F Y. 2008. IL-33 reduces the development of atherosclerosis. J Exp Med 205: 339-46
66. Miller A M, Liew F Y. 2011. The IL-33/ST2 pathway—A new therapeutic target in cardiovascular disease. Pharmacol Ther 131: 179-86
67. Kasuya H, Onda H, Kawashima A, Sasahara A, Hori T. 2001. Identification of genes differentially expressed in canine vasospastic cerebral arteries after subarachnoid hemorrhage. Acta Neurochir Suppl 77: 13-6
68. Schmitz J, Owyang A, Oldham E, Song Y, Murphy E, McClanahan T K, Zurawski G, Moshrefi M, Qin J, Li X, Gorman D M, Bazan J F, Kastelein R A. 2005. IL-33, an interleukin-1-like cytokine that signals via the IL-1 receptor-related protein ST2 and induces T helper type 2-associated cytokines. Immunity 23: 479-90
69. Yasuoka S, Kawanokuchi J, Parajuli B, Jin S, Doi Y, Noda M, Sonobe Y, Takeuchi H, Mizuno T, Suzumura A. 2011. Production and functions of IL-33 in the central nervous system. Brain Res 1385: 8-17
70. Chapuis J, Hot D, Hansmannel F, Kerdraon O, Ferreira S, Hubans C, Maurage C A, Huot L, Bensemain F, Laumet G, Ayral A M, Fievet N, Hauw J J, DeKosky S T, Lemoine Y, Iwatsubo T, Wavrant-Devrieze F, Dartigues J F, Tzourio C, Buee L, Pasquier F, Berr C, Mann D, Lendon C, Alperovitch A, Kamboh M I, Amouyel P, Lambert J C. 2009. Transcriptomic and genetic studies identify IL-33 as a candidate gene for Alzheimer's disease. Mol Psychiatry 14: 1004-16
71. Miller A M, Asquith D L, Hueber A J, Anderson L A, Holmes W M, McKenzie A N, Xu D, Sattar N, McInnes I B, Liew F Y. 2010. Interleukin-33 induces protective effects in adipose tissue inflammation during obesity in mice. Circ Res 107: 650-8
72. Moro K, Yamada T, Tanabe M, Takeuchi T, Ikawa T, Kawamoto H, Furusawa J, Ohtani M, Fujii H, Koyasu S. 2010 Innate production of T(H)2 cytokines by adipose tissue-associated c-Kit(+)Sca-1(+) lymphoid cells. Nature 463: 540-4.
73. Khosroshahi & Stone, A clinical overview of IgG4-related systemic disease Curr. Opin. Rheumatol., 2011, 23(1):57-66.

What is claimed is:

1. A fusion protein comprising a biologically active domain of Interleukin-2 (IL-2) or a biologically active fragment thereof, wherein said domain binds with the IL-2 receptor, and a biologically active domain of Interleukin-33 (IL-33) or a biologically active fragment thereof, wherein said IL-33 domain binds with the IL-33 receptor, further wherein said IL-2 domain is linked to said IL-33 domain with a linker sequence.

2. The fusion protein of claim 1, wherein said protein comprises the amino acid sequence of SEQ ID NO:2 or SEQ ID NO: 11.

3. The fusion protein of claim 1, wherein said linker comprises the sequence of SEQ ID NO:5.

4. The fusion protein of claim 1, wherein said IL-2 comprises the sequence of SEQ ID NO:6 or SEQ ID NO:8 and said IL-33 comprises the sequence of SEQ ID NO:7 or SEQ ID NO:9, or biologically active fragments thereof.

5. The fusion protein of claim 4, wherein said fragment of IL-2 comprises the sequence of SEQ ID NO:3, and said fragment of IL-33 comprises the sequence of SEQ ID NO:4, or biologically active fragments thereof.

6. The fusion protein of claim 5, wherein said IL-2 comprises of at least 95% identity with SEQ ID NO:3 and said IL-33 comprises at least 95% identity with SEQ ID NO:4.

7. The fusion protein of claim 1, wherein said protein is a synthetic protein.

8. A pharmaceutical composition comprising the fusion peptide of claim 1, a pharmaceutically-acceptable carrier, and optionally an additional therapeutic agent.

* * * * *